United States Patent
Todd et al.

(10) Patent No.: US 9,702,016 B2
(45) Date of Patent: Jul. 11, 2017

(54) DIAGNOSTIC TEST FOR VIRUS

(75) Inventors: Danny Todd, Belfast (GB); Victoria Smyth, Belfast (GB); Brian Adair, Belfast (GB)

(73) Assignee: Agri-food and Biosciences Institute, Belfast (GB)

( * ) Notice: Subject to any disclaimer, the term of this patent is extended or adjusted under 35 U.S.C. 154(b) by 183 days.

(21) Appl. No.: 13/259,296

(22) PCT Filed: Mar. 31, 2010

(86) PCT No.: PCT/GB2010/050574
§ 371 (c)(1),
(2), (4) Date: Dec. 7, 2011

(87) PCT Pub. No.: WO2010/112935
PCT Pub. Date: Oct. 7, 2010

(65) Prior Publication Data
US 2012/0087932 A1    Apr. 12, 2012

(30) Foreign Application Priority Data
Apr. 1, 2009   (GB) .................................. 0905614.4

(51) Int. Cl.
*A61K 39/12* (2006.01)
*C07H 21/04* (2006.01)
*C12N 7/00* (2006.01)
*C12Q 1/70* (2006.01)
*A61P 31/12* (2006.01)

(52) U.S. Cl.
CPC ........ *C12Q 1/701* (2013.01); *A01K 2227/101* (2013.01); *A01K 2267/02* (2013.01)

(58) Field of Classification Search
CPC   C12Q 1/701; C12Q 1/6883; C12Q 2600/124; A01K 2227/101; A01K 2267/02
USPC ........................................................ 424/184
See application file for complete search history.

(56) References Cited

U.S. PATENT DOCUMENTS 6,696,562 B1 * 2/2004 Schultz-Cherry et al. 536/23.72

FOREIGN PATENT DOCUMENTS

| WO | WO-2007/130519 A2 | 11/2007 |
| WO | WO2007130519 | * 11/2007 |
| WO | WO-2007/145806 A2 | 12/2007 |
| WO | WO-2009/133054 A1 | 11/2009 |

OTHER PUBLICATIONS

Imada et al., Avian Nephritis virus (ANV) as a new member of the family Astroviridae and Construction of infectious ANV cDNA, 2000, Journal of Virology, 74(18):8487-8493.*

Fredman, J., "Are Oligonucleotide Primers and Probes Prima Facie Obvious Over Largrer Prior Art Nucleic Acids?", (vol. 19 Santa Clara Computer & High Tech. L.J. 285 (2003).*
Cavanagh, "Innovation and discovery: the application of nucleic acid-based technology to avian virus detection and characterization", Avian Pathology, 2001, 30:581-598.*
Knudsen, Henrik, "International Search Report" for PCT/GB2010/050574, as mailed Jul. 26, 2010, 5 pages.
Imada, T., et al., "Avian Nephritis Virus (ANV) as a New Member of the Family Astroviridae and Construction of Infectious ANV cDNA", Journal of Virology, vol. 74, No. 18, Sep. 2000, pp. 8487-8493.
Jonassen, C., et al., "Comparison of capsid sequences from human and animal astroviruses", Journal of General Virology, vol. 82, No. 5, May 2001, pp. 1061-1067.
Nadan, S., et al., "Molecular characterization of astroviruses by reverse transcriptase PCR and sequence analysis: Comparison of clinical and environmental isolates from South Africa", Applied and Environmental Microbiology, vol. 69, No. 2, Feb. 1, 2003, pp. 747-753.
Day, Jm et al, "A Multiplex RT-PCR Test for the Differential Identification of Turkey Astrovirus Type 1, Turkey Astrovirus Type 2, Chicken Astrovirus, Avian Nephritis Virus, and Avian Rotavirus", Avian Diseases 51:681-684, 2007.
Connor J.J. et al., "A survey of avian sera from Northern Ireland for antibody to avian nephritis virus", Avian Pathology, 16:1, 15-20, 1987.
Decaesstecker, M. et al., "Antigenic relationships between fowl enteroviruses", Avian Pathology, 18:4, 715-723, 1989.
Imada, T. et al., "Avian Nephritis Virus (ANV) as a New Member of the Family Astroviridae and Construction of Infectious ANV cDNA", Journal of Virology, p. 8487-8493, Sep. 2000.
Shirai, J. et al., "Avian Nephritis Virus Infection of Chicks: Virology, Pathology, and Serology", Avian Diseases 34:558-565, 1990.
Yamaguchi, S et al., "Characterization of a Picornavirus Isolated from Broiler Chicks", Avian Diseases vol. 23 No. 3, 571-581, Dec. 1978.
Todd, D. et al., "Identification of chicken enterovirus-like viruses, duck hepatitis virus type 2 and duck hepatitis virus type 3 as astroviruses", Avian Pathologhy 38:1, Feb. 21-29, 2009.
Takase, K. et al., "Isolation and characterisation of cytopathic avian enteroviruses from broiler chicks", Avian Pathology, 18:4, 631-642, 1989.
Frazier, Judith A. et al., "Isolation of non-cytopathic viruses implicated in the aetiology of nephritis and baby chick nephropathy and serologically related to avian nephritis virus", Avian Pathology, 19:1, 139-160, 1990.
Pantin-Jackwood, M.J. et al., "Molecular Characterization and Typing of Chicken and Turkey Astroviruses Circulating in the United States: Implications for Diagnostics", Avian Diseases 50:397-404, 2006.

(Continued)

*Primary Examiner* — Janet L Andres
*Assistant Examiner* — Barry A Chestnut
(74) *Attorney, Agent, or Firm* — Winstead PC

(57) ABSTRACT

Unique Avian Nephritis Virus (ANV) nucleic acid sequences have been determined. Primers and probes have been developed using the isolated nucleic acid sequences and a reverse transcription PCR has been developed to detect the presence of ANV in commercial flocks. Furthermore, use of the nucleic acid sequences and amino acids sequences encoded therefrom and antibodies to said amino acids is discussed.

2 Claims, 2 Drawing Sheets

(56) References Cited

OTHER PUBLICATIONS

Mandoki, M. et al., "Molecular Diagnosis of Avian Nephritis: Preliminary Report", Acta Veterinaria Hungarica 54(1), 51-60, 2006.

Shirai, J. et al., "Pathogenicity and Antigenicity of Avian Nephritis Isolates", Avian Diseases 35:49-54, 1991.

Imada, T. et al., "Pathogenicity for Baby Chicks of the G-4260 Strain of the Picornavirus "Avian Nephritis Virus"", Avian Diseases vol. 23 No. 3, 582-588, Dec. 15, 1978.

Decaesstecker, M. et al., "Pathogenicity of fowl enteroviruses", Avian Pathology, 18:4, 697-713, 1989.

Maeda, M. et al., "Pathological Changes in Chicks Inoculated with the Picornavirus "Avian Nephritis Virus"", Avian Diseases vol. 23 No. 3, 589-596, Dec. 15, 1978.

Decaesstecker, M. et al., "Significance of paroviruses, entero-like viruses and reoviruses in the aetiology of the chicken malabsorption syndrome", Avian Pathology, 15:4, 796-782, 1986.

Takase, K. et al., "Susceptibility of embryos and chicks, derived from immunized breeding hens, to avian nephritis virus", Avian Pathology, 23:1, 117-125, 1994.

* cited by examiner

Fig 1 Alignment of 5 representative ANV types to show variable regions
CLUSTAL 2.0.10 multiple sequence alignment

```
ANV-1       MAG-GATAPAGAKPKQPKQKQKKPSSQARKKPSQKQ-KAMKPVKQELRKVEKQVRVLKAR 58
ANV-2       MAG-GATAPAGAKPKQSKQKQKN-SSQRKSKITQKA-KQQKPPVKTVRRLERQVNALKKK 57
VF04-1/2    MPGPAGPANGGARPKTQMAKPKK----AKKPPSQKKPSQCKPLRREIKKVEKQVRVLKKR 56
VF07-13/7   MAGPAGSSNRGARPKTQMAKPKK-----AKKPPSQKK--PSQKPLREEVKKVERQVKVLKKR 55
VF08-3      MPGPAGPANGGARPKTQMAKPKK----AKKPPSQKK-PPQKPPRKEVKKVERQVKVLKKR 55
                     A

ANV-1       TNGPKVNDTMRTTVTVGTLVGQTQSGLNRQLRVSFNPLLMKSTEGGSTTPLSIRASMYEM 118
ANV-2       TNGPKMNDMMRTTVTIGVIQGQTQSGLSRQIRVPLNPLLMKSTEGLAATPLSIRSSCYEL 117
VF04-1/2    TNGPKQNDLFTTTVTLGTISGQSENGLTRQIRLPLNPLLIKSSDGGSTTPLSIRSSMYEM 116
VF07-13/7   TNGPKQNDLVFTTTVTLGTISGQNDNGLTRQIRVPFNPLLCKSSDGGSTTPLSIRSSMYQM 115
VF08-3      TNGPKQNDVFTTTVTLGTISGQNDNGLTRQIRVPFNPLLCKSSDGGSTTPLSIRSSMYQM 115
                                                                    B

ANV-1       WKPLSVETFATPLSGFSSVVGSVGFMVITLNGLEASADSIDTIKARRHVQMALGREYRLK 178
ANV-2       WKALHVELFATPLTGFSNVVGSVGFMALTLNGLEATADSIDSIKARKHYQMALGREARLK 177
VF04-1/2    WKVIRAELIATPLTGGANIVGSVGFMVLTLNELEATADSIDSIKARKHVQIPLGRLARLR 176
VF07-13/7   WKVLKAELRATPLTGGANVVGSVGFMVLTLNGLEATADSIDTIKARKHVQIPIGRSAVLR 175
VF08-3      WKVLKAELRATPLTGGANIVGSVGFMVLTLNGLEATADSIDTIKARKHVQIPIGRSAVLR 175
            B

ANV-1       LSARELAGPREGWWLVDTSEAPADAYGPAVDLMLAYATENILGTSSG---STTSYTGTLWQ 236
ANV-2       LTARELAGPREGWWLTDTSESPVDAYGPAIDLMIAYKTENILNTTGS---YIHLYWTTVAD 235
VF04-1/2    LTARECAGPREGWWLTDTSQSPADSYGPAVDLMIAYATTNILNTSGG---ASATFLGTLWQ 234
VF07-13/7   ILARDCAGPREGWWLTDTSSSPADAYGPAVDLMIAYKTSNILNVSST-TGPQPFTGTLWQ 234
VF08-3      ILARDCAGPREGWWLTDTSSSPADAYGPAVDLMVAYRTSNILNVSSASTQPQSFTGTLWQ 235
                                                              C

ANV-1       VEMRVTYAFSTYNPKPGLQTLVSQSITGG-QTVTIQPSPDDGSLIMTTNSQQVLALLTPR 295
ANV-2       RKRRVTYGFANYNPKPGLQTLVSQTLTNG-QTVTIQPSPNDGSLIMTTTSIQTRSILSPR 294
VF04-1/2    VEIRVTYAFSTYNPKPGLQTMVSQTLAGSNHQVTIQQSTTDGSLIMTINDANLLSILTPR 294
VF07-13/7   AELRVTYAFSTYDPKPGLQTLVSETLSGS-HQVTIQTSADDGSLIMTTTDTQLLSLLTPR 293
VF08-3      AELRVTYAFSTYDPKPGLQTLVSETLSGS-HQVTIQTSADDGSLIMTTTDTQLLSLLTPR 294
            C                                               D

ANV-1       VAGQRKGKSQTIWAIAGSAVDAAATVLGPWGYLLKGGFWLVRLIFGGSSARNTTTRQYQI 355
ANV-2       VGDPKKGKSQTIWAIAGSAVDAAATVLGPWGWLLKGGFWLVRQISGGSS--NAPGSSYQI 352
VF04-1/2    VAGQRSGKSQTVWAIACAAVEAAAPLLGPWGWLLKGGFWLVRKIFGASA--RDTTSQYQI 352
VF07-13/7   TGDQKKGKSPTVWAVAGAVVDAVAPVLGPWGWLLKGGFFLVRKIFGAST---RNAGASYQI 351
VF08-3      TGDQKKGKSPTVWAVAGAVVDAVAPVLGPWGWLLKGGFFLVRKIFGVSA--RNAGASYQI 352

ANV-1       YPSVESALTDQPIFGNSTGTQSVTVPICHITEVVNPNAESNNLPPPTTGAQPQP-QPPAP 414
ANV-2       YSSLESAMADQPIFGAQTGTQSITVPVVHISEVLNPNPMSNQYPTPSTGSAPAPPTPPTP 412
VF04-1/2    YPSIEAAMSDQPIFGQTGTSTCVTLPIVHISEVMNPNPENNDLTNPTARS--LPPVPPAP 410
VF07-13/7   YPSIEQAMSDQPIFGQQSGTTQVTLPLVHVSEVMNPNSESNDLN-PTARS-----LPPIP 405
VF08-3      YPSIEQAMSDQPIFGQQSGTTQVTLPLVHVSEVMNPNSESNDLT-PTSRA-----LPPAP 406
                                                                  E

ANV-1       -IEEILLPLAELTGQPGVPPLYTFDG--SSYTPPTNWLGSTILLTGIPAHKRVTGNLAKF 471
ANV-2       -IQDILLPLAELTGQDGVPANYTFNG--DSYTAQADWRGSTLVLTGIPKHKRVAGNLSNF 469
VF04-1/2    -SEDPILPLAELTGQDGVPANYTFNG--DSYTGQADWRGSTLVLTGIPKEKRVAGSLANF 467
VF07-13/7   PAQEKILPLTLLEGQSGVPALYTFNSGTGAYTPMTRWTGGTLLLTGVPEYELRSGSSQQF 465
VF08-3      -ESEFRLPLALLVGQAGVPAVYFYTG--DAYTPQPRWTGSTIFITGVPYHTRATGATQSF 463
            E                        F
```

```
ANV-1      GVTNLQ---MSKVAATALEIYDFTDFGVFFGTGSYLSEGGIHTGKTLIYSLMSGQTPNPW 528
ANV-2      GVVTNQ---MSKVTTTALEIYDFTDFGIVFGGGYQLQEGGIHTGKTLVHSLMTGAPIKPW 526
VF04-1/2   GVVTNQ---MSKVTTTALEIYDFTDFGIFFGGGYQLQEGGVHTGKTMVHSLMTGAPIKPW 524
VF07-13/7  GVRVQNSPGLSPAAATSIQIYDFTKFGIFFGAGEFLGQGGVHTAKTLLTAITASSNP-PW 524
VF08-3     GVRTNN---MSPSNCTTLDIYDFTDFGVFFGSNGYLSQGAIHTSKTMIYSLKINPNINPW 520
           **        G:     *::*****.**:. *   * :*:,:**,**::  ::     **
H
ANV-1      LAANQSGTTWYMPSWA---GFPQPGQGDYFLQMQDVTDTTTHTTSVNVYFLVAYRQSRRL 585
ANV-2      LYATQSSTTWYWPIWT---GFPKPGEGDYFLQMQDTTDRTTHTTCVGTYIVVAYHQSRRL 583
VF04-1/2   LYATQSSTTWYWPIWT---GFPQPGEGDYFLQMQDTTDRTTHTTCVSVYLLVAYRASRRL 581
VF07-13/7  LDCSR--YTWSWPDWLTSAGYPKPAQGDWLQMQKVGDTTSHTTPVGIYFLIAYEEMQQL 582
VF08-3     LAANQSSTTWSMPTWS---CYPAPCQCDYFLQMQDTTDTTTHTTSVCCYFLVMYCESRKL 577
           H*  ..:   **  *        *:*  *.:**:**.. * *:*** *. *::: *    ::*

ANV-1      IAFFNTGGT-ARPAPTSMLCLYNVDCGRAPQTPYPTFQSTLQSLNQIGVDAKS-DEDSDD 643
ANV-2      IAFFNNAGP-VRAAPTTMLCLYNVDAGRAPATPYNTFQLTLQSE---GTDPNSPSEDEDD 639
VF04-1/2   IAFYNNGGP-VRAAPTTMLCLYNVDAGRAPATPYNTFQLTLQSE---GADPNSPSEDEDD 637
VF07-13/7  VAFWHTGSG-AQAEPTSLLCLYNVDAGRAPVR-VPHFIITTTAR---NEVEVDGGD-DSDD 637
VF08-3     VAFFNTCTGTARPALSSMMCLYNVDACRAPVR-IQCFLLSPSQ---NFVETDNQDNDDDD 633
           :**::..   ..  :::::*******.****  *  : . . .: ...  . *.**

ANV-1      DISLAGSVIGDEFDSVDHLEREREDLMRRLRDLDLRRFQI 683  SEQ ID NO 36
ANV-2      DISLAGSCLQDEFDCVDQLEKEREDLMRRLRDLDLRRFQI 679  SEQ ID NO 37
VF04-1/2   DISLAGSCLQDEFDCVDQLEKEREDLMRRLRDLDLRRFQI 677  SEQ ID NO 38
VF07-13/7  DISLAGSCVGDEFEGVDQLEKERAELMSRLRDLDLRRFQI 677  SEQ ID NO 39
VF08-3     DISLAGSCLQDEFDCVDQLEKEREDLMRRLRDLDLRRFQI 673  SEQ ID NO 40
           ******  :  ***:  **:**:* :**  ************
```

Fig 1 (cont)

DIAGNOSTIC TEST FOR VIRUS

FIELD OF THE INVENTION

The present invention relates to nucleic acid and amino acid sequences of Avian Nephritis Virus (ANV) and the use of such sequences in diagnostic tests for ANV and/or as mediators of the immune response in animal, in particular avians, for example as a vaccine for ANV. In particular, the present invention relates to a PCR test and a quantitative PCR test for ANV and primers and probes for said tests.

BACKGROUND OF THE INVENTION

Avian Nephritis Virus (ANV) was isolated in the 1970s and ANV infections are known in chickens and turkeys. ANV exhibits different degrees of pathogenicity in chickens and turkeys and can present as sub-clinical infection, renal damage, growth retardation, or death of the bird.

ANV has been classified as an astrovirus based on its genome-sequence, with the genome of the G4260 isolate (ANV-1) having been cloned and sequenced (Imada T, Yamaguchi S, Mase M, Tsukamoto K, Kubo M, Morooka A. (Avian nephritis virus (ANV) as a new member of the family Astroviridae and construction of infectious ANV cDNA). J Virol. 2000 September; 74(18):8487-93.).

Previous work has identified at least two serotypes of ANV with representative isolates of serotype 1 (ANV-1) (G4260) (AB033998) and serotype 2 (ANV-2) (e.g. M8) (AB046864) exhibiting very low levels of cross-reactivity by indirect immunofluorescence (IIF) tests and serum neutralisation (SN) tests.

ANV is not easy to isolate and virus specific antisera may not cross-react with other antigenically different ANVs when used in immunostaining-based methods. Whilst there has been some use of RT-PCR tests in relation to the detection of ANV, this has been restricted due to limited knowledge in relation to the sequence variability between known ANV isolates and the sequence diversity that underpins the biological diversity of ANV. A lack of knowledge of ANV viruses has restricted the identification of suitable primers which can be used to detect and quantify the amounts of ANV in a sample, using RT-PCR. In view of this, the nature and extent of disease problems caused by antigentically different ANV types have not been defined due to the absence of convenient diagnostic tests for such antigentically difference ANV types.

SUMMARY OF THE INVENTION

The present inventors have determined the partial nucleic acid sequences of around 20 ANV genomes and used these to elucidate three representative nucleic acid sequences and corresponding protein sequences of capsid proteins of antigenically different ANV types.

Further, the inventors' determination of the 3'UTR (untranslated region) sequences from the determined ANV sequences for a number of antigentically different ANV types has enabled them to determine that the 3'UTR portion of the ANV genome is conserved and in particular has allowed for the selection of particularly advantageous portions of 3' UTR ANV nucleic acid sequence against which primers can be designed to allow conventional and quantitative RT-PCR to be performed. These primers enable RT-PCR and improved detection of ANV due to their enhanced specificity for ANV types other than ANV-1 and ANV-2. Additionally, the identification of the conserved nature of the 3'UTR of antigentically different ANV types has allowed nucleic acid probes to the 3'UTR to be provided for use in the invention.

Accordingly, a first aspect of the present invention provides a method for detecting avian nephritis virus in a sample to be tested comprising the steps:
 a. isolating total RNA from a sample to be tested,
 b. synthesising a first strand of DNA from said isolated RNA using a reverse primer which is complementary to a portion of the 3' untranslated region (UTR) of the virus,
 c. amplifying said first strand of DNA to form an amplified product and
 d. detecting the amplified product In embodiments of the invention, the amplified product comprises a nucleic acid sequence acggcgagtagcatcgagggtacaggaaagctgggaccattgcatagtcaactaatttggctgtgcta gggggaccaatggggtggtaggtcaatcaaaccgccactcacgcaacttggagcctgctaaaacct acgctcctgtgcgctaaagttggttctcccgaaagtgggcttttcatt (SEQ ID NO 7) or a nucleic acid sequence with at least 80%, at least 85%, at least 90%, at least 95%, or at least 99% sequence identity to SEQ ID NO 7.

In embodiments, a nucleic acid, for example a primer for use in the method is complementary to, (can selectively hybridise DNA, RNA and CDNA sequences comprising) a portion of the 3' UTR of the virus with the sequence acggcgagtagcatcgagggtacaggaaagctgggaccattgcatagt-caactaatttggctgtgcta gggggaccaatggggtggtaggtcaatcaaaccgc-cactcacgcaacttggagcctgctaaaacct acgctcctgtgcgctaaagttggt-tctcccgaaagtgggcttttcatt (SEQ ID NO 7), which can be used to amplify the first strand of DNA Suitably, in embodiments of the method, a reverse primer for use in the method can be complementary to a portion of the 3' UTR of the virus with the sequence acggcgagtagcatc-gagggtacaggaaagctgggaccattgcatagtcaactaatttggctgtgcta gggggaccaatggggtggtaggtcaatcaaaccgccactcacgcaacttggagc-ctgctaaaacct acgctcctgtgcgctaaagttggttctc-ccgaaagtgggcttttcatt (SEQ ID NO 7) or a nucleic acid sequence with at least 80%, at least 85%, at least 90%, at least 95%, or at least 99% sequence identity to SEQ ID NO 7.

In embodiments of the method, the step of amplifying said first strand of DNA can use a forward primer comprising the sequence ACGGCGAGTACCATCGAG (SEQ ID No 8) and a reverse primer comprising the sequence AATGAAAAGC-CCACTTTCGG (SEQ ID NO 34).

In alternative embodiments of the invention, the amplified product can comprise a nucleic acid sequence gtaaaccactggttggctgactacagcaactgactttcccgaggccacggcgagta (SEQ ID NO 10) or a nucleic acid sequence with at least 80%, at least 85%, at least 90%, at least 95%, or at least 99% sequence identity to SEQ ID NO 10.

In embodiments of the method, a nucleic acid, for example a primer which is complementary to a portion of the 3' UTR of the virus with the sequence gtaaaccactggttggct-gactacagcaactgactttcccgaggccacggcgagta (SEQ ID NO 10) can be used to amplify the first strand of DNA.

Suitably, in embodiments of the method a reverse primer for use in the method can be complementary to a portion of the 3'UTR of the virus comprising the nucleic acid sequence gtaaaccactggttggctgactacagcaactgactttcccgaggccacggcgagta (SEQ ID NO 10) or a nucleic acid sequence with at least 80%, at least 85%, at least 90%, at least 95%, or at least 99% sequence identity to SEQ ID NO 10.

In embodiments of the method, the step of amplifying said first strand of DNA can use a forward primer comprising the sequence GTAAACCACTGGYTGGCTGACT, (SEQ ID NO 11) where Y is C or T, and a reverse primer comprising the sequence TACTCGCCGTGGCCTCG (SEQ ID NO 35).

The present invention provides a method for detecting the presence of avian nephritis virus utilising nucleic acid amplification techniques, for example reverse transcriptase-PCR methods, utilising repeated cycles of denaturations, primer annealing and extension carried out with polymerase, for example Taq polymerase, to lead to exponential increases in derived nucleic acid. The skilled person could use any computer programs for example, Vector NTO, OLIGO, or Jelly fish (Biowire) to design specific probes or primers to the 3'UTR, in particular to SEQ ID NO 7 or 10.

In embodiments of the method, the step of detecting the amplified product can use a detectable probe comprising the sequence CAGCAAATGACTTTC (SEQ ID NO 13).

Any suitable method utilising sets of primers and/or probes that are useful for amplifying/detecting target sequences of ANV can be used. In embodiments, the ANV nucleic acid sequences are detected using fluorogenic a 5' nuclease assay, such as the TaqMan technique. Other nucleic acid based detection techniques such as, but not limited to reverse transcriptase-polymerase chain reaction (RT-PCR) and transcription-mediated amplification (TMA) can be used.

In embodiments, the sample can be from an avian. In embodiments, the method can comprise the step of extracting RNA from the sample. Total RNA can be obtained by methods or kits well established in the art, for example TRIzol® Total RNA Isolation Reagent (Life Technologies™, Rockville, Md.), or Rneasy (Qiagen). In particular embodiments the method comprises the steps of
  a) extracting RNA from the sample obtained from the asymptomatic subject;
  b) subjecting the extracted RNA to an amplification method, for example using at least one set of oligonucleotide primers comprising a forward and reverse primer capable of amplifying a 3'UTR ANV nucleic acid segment, designed to produce, if the extracted RNA includes ANV RNA, an amplified fragment of ANV cDNA;
  c) assaying for the presence of the amplified fragment of ANV cDNA; and
  d) if the amplified fragment of ANV cDNA is present, thereby identifying the asymptomatic subject as being at risk of developing ANV induced clinical effects.

Suitably, methods utilising a PCR approach and assaying for the presence of amplified fragments of ANV DNA may find application in detecting ANV in dead in shell embryos. These are embryos which do not hatch. It is suggested the ANV virus is present in low amounts in such embryos, and possibly other diagnostic tests based on detecting antigen would not be of sufficient sensitivity to determine such low levels.

Based on the sequences of the ANV genomes determined by the inventors, the inventors have determined capsid protein amino acid sequences of ANV which are representative of different antigenic ANV types studied. Three representative amino acid sequences SEQ ID NOs 4, 5 and 6 (encoded by SEQ ID NOs 1, 2 and 3 respectively) determined by the inventors have an amino acid sequence homology which has a divergence of greater than 20% when compared to the capsid protein amino acid sequences from ANV-1 and ANV-2 provided in the literature. In an aspect of the present invention, there is provided the use of the identified representative capsid protein amino acid sequences, optionally in combination with any or both of the two ANV capsid protein sequences already known (from ANV-1 and ANV-2), for improved detection and thus more robust tests for ANV.

Accordingly, a second aspect of the present invention provides (a) at least one nucleic acid sequence which encodes a capsid protein comprising a nucleic acid sequence which has at least 80%, at least 85%, preferably at least 90%, preferably at least 93%, more preferably at least 95%, more preferably at least 98%, even more preferably at least 99%, and most preferably 100% sequence identity to at least one of SEQ ID NO 1, SEQ ID NO 2, and SEQ ID NO 3, (b) a nucleic acid sequence that is capable of hybridising to any one of (a) under stringent conditions, or (c) a fragment of (a) or (b) wherein an amino acid sequence encoded by such a fragment is capable of generating an immune response in an animal.

In embodiments, there is provided a nucleic acid sequence comprising a) at least one of SEQ ID NO 1, 2 or 3, b) a nucleic acid sequence that is capable of hybridising to any one of SEQ ID NOs 1 to 3 under stringent conditions, or c) a fragment of (a) or (b) wherein an amino acid sequence encoded by such a fragment is capable of generating an immune response in an animal, and is not found in the nucleic acid sequence coding for the capsid protein of ANV-1 or ANV-2.

In embodiments there is provided a nucleic acid sequence comprising or consisting of at least one of SEQ ID NO 1, 2, or 3.

According to a third aspect of the present invention there is provided a) at least one amino acid sequence of a capsid protein comprising an amino acid sequence which has at least 80%, at least 85%, preferably at least 90%, preferably at least 93%, more preferably at least 95%, more preferably at least 98%, even more preferably at least 99%, and most preferably 100% sequence identity to at least one of SEQ ID NO 4, SEQ ID NO 5, and SEQ ID NO 6 or a fragment thereof.

In embodiments there is provided an amino acid sequence comprising at least one of SEQ ID NO 4, SEQ ID NO 5, and SEQ ID NO 6, or a fragment thereof wherein said fragment is capable of generating an immune response in an animal, and said fragment is not found in the amino acid sequence of the capsid protein of ANV-1 or ANV-2.

The invention also relates to the nucleic acid and amino acid sequences of capsid proteins of particular ANV types determined by the inventors, which allow for identification of particular antigenic ANV types. This is useful as ANV isolates from the same and different serotypes show different pathogenicity, as indicated by the degree of growth retardation and kidney pathology (nephritis and nephrosis) that is observed following experimental inoculation. Further, there is some evidence that particular isolates of ANV may exhibit tissue tropism differences.

Accordingly, a fourth aspect of the present invention, provides a nucleic acid sequence comprising at least one nucleic acid sequence selected from:

a) VF04-1/2:

(SEQ ID NO 1)

atgcctggccctgccggccctgccaatgggggcgctcgcccaaaactcaaatggccaaacccaag aaggctaaaaaacctccatctcagaaaaagccttctcagcaaaaaccactcagaagggaaataaa aaaggtggagaaacaggtgagagtgctcaagaaacgcactaatgggcccaagcagaatgatctctt cacaacaactgttacgcttgggacaatttctggacagagtgacaatggccttactaggcagataaggc tgccacttaatccgctacttctgaaatcatcagacggtggttctacaacaccactctctatacgcggttca atgtatgagatgtggaaagttattagagcggaactcatcgccactcctctaacaggtggtgctaatattgt gggctccgtcggcttcatggtactcacccttaatgagcttgaagcaactgcagactcaatcgactccatc aaagccagaaagcatgtccagataccacttggtaggcttgcaagactgaggctcaccgcgcgtgaat gcgcgggtccgcgtgaaggctggtggcttactgatacttcccagtcaccagctgactcgtatgggcca gcagtcgatcttatgattgcctatgcaaccacaaacctcctcaatacatctgggggagctagtgctacct ttcttggtactctctggcaagttgaaatcagagtcacctatgcttttagcacctacaatccaaaaccaggt ctgcaaacaatggtttcgcaaaccctggctggctcaaatcatcaagtcacaattcagcagtcgacaac tgatggctcccttataatgacaacaaatgatgccaacctcctttctatccttaccccgtgttgcggggc agaggtcaggaaagtctcagacggtctgggcgattgctggggctgcggttgaggccgctgctccactg cttgggccgtggggttggcttctaaaaggggttttttggcttgtgaggaaaatctttggtgcgtctgcacgt gacaccacttcacagtaccagatctatccctctattgaagccgcaatgtctgaccaacctattttttggtca aactggcacttccacaactgtcactctgcctattgtgcacatctcagaggtgatgaatcctaaccctgag aataatgacctgactaatccaaccgccaggtctctcccaccagtaccaccagcaccttcagaagacc ccatactcccgttggcggaacttactgggcaagatggggttccagcaaattacacctttaatggtgactc ctatacgggtcaagctgattggaggggctctacacttgttcttactggaataccaaaacataagcgagt agctggtagtctggccaattttggtgtggtaactaaccaaatgtcaaaggtcaccaccactgcccttgag atctatgacttcaccgattttgggatcttcttcggtggaggctatcaacttcaggaaggtggtgtacacact ggcaaaacaatggtacactcgcttatgacaggtgcccctataaaaccctggctttatgcaactcaatca tctacaacatggtattggccaacctggactggcttttccacagcccggagaaggcgactatttcctacag atgcaggacaccactgatagaactacacatacaacttgtgttagtgtatatctgcttgttgcctatcgagc gtcgcgtagacttatagccttctataacaacggcggtcctgtgcgggcggctcctacaaccatgctctgc ttatacaatgtagatgcaggccgggcaccagcaacaccttacaacaccttccaactcacacttcaaag tgaaggtgctgacccaaattctccatctgaagatgaagacgatgacatctcattggcgggttcatgtcttc aagatgagtttgattgtgtggatcaactcgaaaaagaaagagaagatcttatgaggaggttaagagat ctagacctccggcgctttcagatc, b) VF07-13/7:

(SEQ ID NO 2)

atggctggccctgcgggctcgtccaatcggggcgctcgcccaaaactcaaatggcaaaacctaaga aggctaagaaacctccatctcagaaaaagccttctcaaaaaccactcaggaaggaagtaaaaaag gtggaaagacaggtcaaggtgcttaagaaacgcaccaatggccctaagcaaaatgatgtgttcaca acaacagtcacccttggaaccatctcgggccaaaatgacaatggtctaaccaggcaaattcgggtgc ctttcaaccccctactttgtaagtcatctgatggtggctccaccacaccactatctataaggggttcaatgt atcaaatgtggaaggtgcttaaggcagagctacgtgcaacaccactaacaggggggcaaatgtag tcggttcagtcggctttatggttctcacccctaaatggtctcgaagccactgcagattccatcgacacaata aaagcaagaaagcacgtgcagattccgataggcagaagtgccgttcttcgcattcttgcacgcgattgt gcgggtcctcgcgagggttggtggctcactgatacttcaagctcaccagctgacgcttatgggcctgcg -continued gttgatcttatgattgcctataaaacatcaaacttgcttaatgtgtcaagtaccaccggtcctcaacccttta ccggtactctgtggcaggcggagctcaaagttacttatgcttttagtacctacgacccgaaacctgggct tcagacccttgtgtcggagacactctctggtagtcatcaagtcactattcaaacctcagcagacgacgg ctcacttataatgacaacaactgatacgcaactgctttcactccttacgccacgtacgggtgaccagaa gaagggaaatctccaactgtctgggcagtcgcaggcgccgttgttgatgctgtagcccctgtactagg acctggggctggctacttaagggtggcttcttcctcgttaggaagatctttggggcttctactcggaatgc gggagcgtcttatcagatctacccctcaattgagcaggctatgtctgatcaaccaatttttggtcagcaat ctggaacaacacaagtgacactcccgcttgttcatgtttccgaggttatgaaccccaactccgagagta acgacctaaatccaactgctaggtcacttccacctattccacctgctcaggagaaaattttaccacttact ctcctcgagggtcaatcaggtgtccctgcactctacacctttaactctgggactggagcttatacccccat gacgcgttggacaggtggtactctacttctcactggtgtaccagaatatgagctccgtagtggatcctca caacaatttgggggttcgagtacaaaactcaccaggcctatcaccagctgcggcaacatcaatacaaa tttatgattttacaaaatttggcatcttctttggtgctggtgagttccttgggcaaggggagtccatacagc aaagactctcctgacagcaatcactgcttctagcaaccctccctggcttgattgttccaggtacacatgg agctggcctgattggcttacctcggctggctatccaaaacctgcccagggtgattggtggctgcagatg caaaaagttggtgacactacatctcacacgaccccagttggcatctatttcttaatagcgtatgaggaga tgcaacaacttgtggcattctggcacacgggttctggagcccaagccgaacccacttctcttctgtgcct atacaatgttgatcagggcgtgcacctgtgagagtcccacacttcattattacaactactgcccgcaat gaagtggaggttgatgggggtgatgactcagacgacgacatctctcttgctgggtcttgtgttggcgacg agtttgagggtgtggatcaactcgaacgcgaaagggcagaactcatgagcaggttaagagacctag acctgcggcgctttcagatc, c) VF08-3a:

(SEQ ID NO 3)

atgcctggccctgccggccctgccaatggggcgctcgcccaaaactcaaatggcaaaacctaag aaggctaagaaacctccatctcagaaaaagcctcctcaaaaaccacccaggaaggaagtgaaga aggtggaaagacaggtaaaggtgcttaagaaacgcaccaatggccctaagcagaatgatgtgttca caacaacagtcactcttggaaccatctcgggccaaaatgacaatggtctaaccaggcaaatccgggt gcctttcaaccccttactatgtaagtcatctgacggtggttctaccacaccactgtcaataaggggttcaa tgtatcaaatgtggaaggtgcttaaggcagagctacgtgcaacacctctaacaggggggcaaatat agttggctcagtcggctttatggttctcaccctgaacgggctcgaagccactgcagactccatcgacac aataaaagcaagaaagcacgtgcagattccaattggcagaagtgccgttcttcgcatacttgcgcgtg attgtgctgggcctcgcgaaggctggtggctaactgatacgtcaagctcaccggctgacgcatatgga cccgcagtcgacccttatggttgcctacagaacatcaaacttgcttaatgtgtcgagtgccagtacccaac ctcaatcctttactggtactctgtggcaggcagagctcaaagttacatatgcttttagcacctatgacccg aaacctggtcttcaaactctcgtgtcagagacgctatctggtagccatcaagttactattcaaacttcagc agacgacggctcacttataatgacaacaaccgatacgcaactgctgtcactccttacgccacgtacgg gtgaccagaagaagggaaagtccccaactgtctgggcagtcgcaggcgccgttgttgacgctgtagc ccctgttctaggaccctggggctggctacttaagggtggcttcttcctcgttaggaagatctttggggtttct gcccggaatgcgggagcgtcctatcagatctacccctctattgagcaggctatgtctgatcaaccaatct ttggtcagcaatctggaacaacacaagtgacactcccgcttgtccatgtctccgaggttatgaacccca actccgagagtaacgacctaactccaacttcaagggctcttccacctgcacctgagtcagagcctgag -continued cttccactggctcttctagttggccaggctggtgtccctgcagtgtatgagtatactggggatgcctataca ccacaaccaagatggactggctcaactatcttccttactggtgttccctatcatactagggctacaggtgc tacacagtcttttggagtgagaactaacaatatgtcaccttcaaactgcaccacacttgatatctatgactt cacagattttggggtcttttttggtagtaatggctacctttcacaaggtgccatacatacttcaaaaacaat gatctactcactcaagacaaatccaaatatcaaccctggcttgctgcaaaccagtcttccaccacgtg gtccatgccaacgtggtctggctatcccgcaccaggccaaggagattacttcctgcaaatgcaagata ccaccgatacaaccacccatacgacttctgtgggttgttattttctggtgatgtatggtgaatcccggaaa cttgttgcattttttaatactggcactggcacagcaagacctgcactttcatctatgatgtgcctctataatgtt gatgcaggaagagcaccagtaaggatacagggctttcttctcagcccttcacaaaactttgttgaaact gataatcaggacaatgacgacgatgatgacatctctctcgccgggtcctgtctgcaagatgagtttgatt gtgtggatcaactcgaaaaagaaagagaagatcttatgaggaggcttagagatctagacctccggcg ctttcagatc, d) ELV276CI5:

(SEQ ID NO 14)

atggctggcggtgccaccgcacctgcgggcgctaagcccaagcagtccaaacaaaagcagaaaa attcttctcagcggaaatctaaaaccactcagaaggtgaaacaacaaaaacctccagtgaaaactgtt aggaggcttgagcaccaagtcaacgcactcaagaagaagacaaatggacccaaaatgaatgaca tgatgaaaactactgtcacaattgggtcatccaaggtcagactcaatcaggtctcagtcgccaactta gggtgccactaaacccctcttaatgaaatctacagaggggctagctgctaccccgctatccattaggt catcttgctatgagctctggaaagcactacatgttgagcttttgcaacaccactaactggtttctccaatgt ggtgggctcggtaggctttatggctctaacactcaatgggcttgaggcgaccgcagactccatcgactc aatcaaggcgaggaaacactaccaaatggcccttggtaggccagcgcggcttaaactcactgcccg tgaacttgcggggccgcgcgagggctggtggctcactgatacatctgaatcgcctgcagatgcgtatg gacctgctatagacctgatgattgcttataaaactgagaaccttcttaatacaacaggttcgacgacctc cacccacactggaccactgtggcagatagaagcgcgggcgacttatgggtttgccaactacaaccca aaaccaggacttcaaacgctcgtctctcaaacactgaccaacgggcaaacggtgacaatccaaccg tcaccaaatgatgggtctctcataatgacaacaaccagcctacaggtccgatcgctgctttcccctcgg gctggtgacccaaagaaggggaagtctcagacaatctgggccatagcaggttctgcagttgatgctg cggcaaccgtccttggtccctggggctggctactaaagggtggtttctggctagttagacaaatctttggt ggatcgtctaatgctgcaggcagcagctaccagatttattcctcccttgagtctgcaatggctgatcaac ccatctttggcgcccaaactggtacccagtctattactgtacctgtagtgcacatctctgaagtcctgaatc caaacccaatgtccaaccaagtacccacgcccagtgctggctcggcacctgcgccaccaacacccc caaccccattcaagacatcatacttccgctcgcggaactgacggggcaagatggggttccagcaaa ttacacctttaatggtgactcttatacgggtcaaggcgattggagggggttctacacttgttctcactggaat accaagacataagcgagtaaccggaaatctgtctaattttggtgtgacagttaatcaaatgtcaaaagt caccacaactgcacttgagatctatgacttcaccgattttggtgtctccttcggtggaggctaccaacttca ggaaggtggtgtacatactggcaaaacaatggttcactcgcttatgacaggtgccccaataaaaccct ggctttatgcaactcaatcatctacaacatggtactggcccacctggactggctttccacagcctggtcct ggcgactattttctacagatgcaggacaccactgacagaacaacacacacaacctgtgttagtgtctat ctgcttgtcgcctaccaagcgtcgcgcaggcttatagcgttctacaacaacggtggtactgcgcgggcg gcgcctacaaccatgctttgtctatacaatgtagatgcaggccgggcaccacaaacacccttataacac cttccaactcacacttcaaagtgaagttgctgacccaaattctccatctgaagatgaagatgatgacatc -continued tcgcttgcgggttcttgtcttcaagatgagtttgattgtgtggatcaactcgaaaaagaaagagaagacct tatgaggaggttaagagacctagacctccggcgctttcagatc, e) ELV276CI3:

(SEQ ID NO 15)

atggctggcggtgccaccgcacctgcgggcgctaagcccaagcagtccaaacaaaagcagaaaa ctccatctcagcggaaacttaaatccactcagaaggcgaaacaacaaaaacctccagtgaaaacg gttaggaggcttgagcgccaagtcaacgcactcaagaagaaaacaaatgggcccaaaatgaatga catgatgaagacaactgtcacaattggggtcatccaaggtcagacccaatcaggtctcagtcgccaa cttagggttccactaaatcccctcttaatgaaatctacagagggttagctgcgaccccgctgtccatta ggtcatcctgttatgagctttggaaagcactacatgttgacttttgcaacaccactgactggtttctccaa tgtggtgggctcggtaggctttatggctcttacactcaatggactggaggcaaccgcagactccatcga ctcgatcaaggcgaggaaacactaccaaatggcccttggaaggccggcgcggcttaaactcactgc ccgtgaactcgcggggccgcgtgagggctggtggcttactgatacatccgaatcgcctgcagatgcgt atggacctgccattgacctgatgattgcttacaaaactgagaaccttcttaatacaacaggttcgacgac ctccacttacactgggcccctgtggcagatagaagcgcgggtgacttatgggtttgccacctacaaccc aaagccaggacttcaaacgctcgtttctcaaacactgactaacgggcaaacggtgacaattcaaccg tcaccaactgatgggtctctcataatgacaacaaacagcctacagattcgcacattgctttcccctcggg ccggtgacccaaagaaggggaaatcccagacaatctgggccatagcaggttccgcagttgatgcag cggcaaccgttcttggcccctgggggttggctacttaagggtggattctggctagttagactgatctttggtg gatcgactaatgccacaactagcagctaccagatttattcctcccttgagtctgcaatggctgatcaacc catctatggtgctcaaactggtacccagtccattactgtacctgtggtgcacgtttctgaagttctgaatcc aaacccagtgtccaaccaagtacctacgcccagtactggttcggcacccgcgccacctacaccacc agcaccatctgaagaccccatactcccgctggcagaattaactggccagcctggggtccccacctctct acacctttgatggcagtacttacactccaccgactaactggttgggctccactctattactaactggtatac cagcacataaaagagttactggtaatttggctaactttggagtcaccaaccttcaaatgtcaaaagtca ctgccactgcaattgaggtctatgacttcacagactttggtgtgttctttggcactggcacttaccttggtga aggcggcattcacaccgggaagaccctagtgtattccctgatgtctggtcaaaccccgaacccctggc tcgctgcaaatcagtcagggacgacctggtacctcccgtcgtgggttggttttcctacaccaggtgcgg gtgactacttccttcaaatgcaggatgtaacagacacaacaactcacacaacatcagtgaatgtttatttt ctggtagcctaccgtgaatcccgtaggctaattgccttctttaacacaggaggcacagcacgtccagcg ccggcatcaatgatctgtatgtacaacgtcgattgtgggcgtgcacctcaaacaccgtaccccacatttc agtcgacattgcagccaaaagatgaggtggacaattctcaaaccctgacgatgatgatgacatctct ctcgcagggtcctttataggcgacgagtttgatagtgtggatcaactcgaacgcgaaagggaagatct aatgaggaggttaagagatctggacctccggcgctttcacatc, f) Belgian ELV1:

(SEQ ID NO 16)

atggctggcggtgccaccgcacctgcgggcgctaagcccaaacaacccaaacaaaagcagaaaa cttcctgtcagaggaaatccaaacctactcagaaggttaaacaacaaaaacctcctgtgaaaactgtt aggaggcttgagcgccaagtcaacgcactcaagaagaagacaaatgggcccaaaatgaatgaca taatgaaaactactgtcacacttggggtcatccaaggccagactcaatcaggtctaagtcgccaactta gggtgccactaaaccccctcttgatgaaatctacagaggggctagctgcgaccccgctgtccattaggt catcttgttatgagctatggaaagccctacatgtcgagcttttgcaacaccactgactggcttttccaatgt -continued ggtgggctcggtaggctttatggctcttacactcaatggacttgaggcgaccgcagattccatcgattca attaaggcgaggaaacattatcaaatggccctcggtaggccagcgcggcttaaacttactgcccgtga actcgcggggccgcgtgagggctggtggcttactgacacatctgaatcgcctgcagatgcctatggac ctgccatcgacctgatgattgcctacaaaactgagaaccttctcaatacatcaggttctacgacctccac ttacactggacccctgtggcagatagaagcgcgggtgacttatgggttcgccacttacaacccaaagc caggacttcaaacgctcgtgtctcaatcattgaccaacgggcaaacggtgacaatccaaccgtcacc aactgatgggtctcttataatgacaacaaacagcctacagattcaatcactgctctccctcgggttgat ggcccacagaagggggaagtcccagacaatctgggccatagcaggttctgcagttgatgctgcggca accgttcttggtccctggggctggctacttaaaggtggtttctggctagttagactgatctttggtggatcgt ctaatgctgcaggcagcagctaccagttatactcctcccttgagtctgcaatggctgatcaacccatctat ggtgctcaaactggtactcagtccatcactgtacctgtggtgcacatctctgaagtcctgaatccaaatcc aatgttcaaccaggtatctgtgcctaccactggttcggcacctgcgccaccaacaccaccagcaccat ctgaagacccatactcccgctggcagaattaactggccaacctggggtcccacctctctacacctttg atggcagtacctacactccaccgactaactggctgggctccactctattactaactggtataccagctca caaacgagtcactggtaattcggctaattttggagttaccaaccttcaaatgtcaaaagtaactgccact gcaattgaggtctatgacttcacagactttggtgttttcttcggcactggcacttatcttggtgaaggtggca ttcacactgggaagaccttagtgtactccctgatgtctggtcaaccccaaaaccctggcttgcagcaa accagtcagggacgacctggtacctcccttcgtgggttggttttcctacaccaggtgcgggtgactacttc cttcaaatgcaggatgtaacagacacgacaactcacacaacatcagtgaatgtctactttctggtggcc taccgtgaatcccgtaggctaattgccttctttaacacaggaggcacagcacgtccagcgccaacatc aatgatctgtatgtacaacgtcgattgtgggcgtgcacctcaaacaccgtaccccacatttcaatcgac actgcagtcaaaagatgaggtggacaattctcaaacccctgatgatgatgacatctctctcgcagggtc ctttataggcgacgagtttgatagcgtggatcaactcgaacgcgaaagggaagatctaatgaggagg ttaagagatctagacctccggcgctttcacgtc, g) VF05-1/5:

(SEQ ID NO 17)

atgcctggccctgccggccctgtcaatggggggcgctcgccccaaaactcaaatggccaaacccaag aaggctaaaaaatctccatctcagaaaaagccttctcagcaaaaaccactcagaagggaaataaa aaaggtggagaaacaggtgagagtgctcaagaaacgcactaatgggcccaagcagaatgatctctt cacaacaactgttacgcttgggacaatttctggacagagtgacaatggccttactaggcagataaggc tgccacttaatccgctacttctgaaatcatcagacggtggttctacaacaccactctctatacgcggttca atgtatgagatgtggaaagttatcagagcggaactcatcgccactcctctaacaggtggtgctaatattg tgggctccgtcggcttcatggtactcacccttaatgggcttgaagcaactgcagactcaatcgactccat caaagccagaaagcatgtccagataccacttggtaggcttgcaagactgaggctcaccgcgcgtga atgcgcgggtccgcgtgaaggctggtggcttactgatacttcccagtcaccagctgactcgtatgggcc agcagtcgatcttatgattgcctatgcaactacaaacctcctcaatacatcggaggagctagtgctacc tttctcggtactctctggcaagtcgaaattagagtcacctatgctttcagcacctataatcccaaaccagg tctgcaaacaatggtttcgcaaactctggctggatcaaatcatcaagtcacaattcggcaatcaacaac tgatggctcccttataatgacaacaaatgataccaacctcctttccatccttactccccgtgtcgcggggc aaaggtcaggaaagtcccagacggtttgggcgattgctggagctgcggttgaagccgccgctccact gcttgggccgtggggttggcttctaaaaggggggcttttggcttgtgagaaaaatctttggtgctagtgcac gtgacacgacctcacagtaccagatctatccttccattgaagccgcaatgtctgaccaaccaatctttgg -continued tcaaactggtacatctacaactgtcactctgcccattgtgcacatttcagaagtgatgaatcctaaccctg agaataatgacctatcaaatcctacatctaggtcatttccacctactccgcctaccccttctactgatccca ttcttcctctggcggagctaactggacaaccgggggttccacctctttacacctttgatggcagtacttaca ccccaccaactaattggctgggctctactactttgttaactggtattccagcacataaacgagtgactggt aacttgtctaactttggagtcaccaacctccaaatgtcaaaagttactgccactgcaattgagatttatga cttcacagactttggtgtcttttttggcactggtagttaccttggtgaaggtggcattcacactgggaagact ttaatccattccttgatgtctggtcaaaccccgaacccctggcttgctgcaaaccagtcagggacgacct ggtacctccctacttgggttggctttcctacaccaggtgcgggtgattacttccttcaaatgcaggatgtga cagacacgacaactcacactacatctgtgaatgtgtacttcctggtagcttaccaccagtctcgaaggct catagccttcttcaacactggaggcacagctcgtccagcaccaacatcaatgctttgtctctataatgttg actgtgggcgtgctccacaaacgccctaccctacttttcagtcaacactccaaagtctgactcaatctga ggtggatgcaaaaactgatcccgactccgacgatgacatttcacttgcggggtcggtcattggcgacg agtttgatagtgtggatcatctcgaacgcgaaagagaagatttaatgaggaggctcagagatctagac ctccggcgctttcagatc, h) VF08-3b:

(SEQ ID NO 18)
atgcctggccctgccggccctgccaatgggggcgttcgcccaaaactcaaatggcaaaacctaag aaggctaagaaacctccatctcagaaaaagccttctcaaaaaccactcaggaaggaagtgaagaa ggtgaaagacaggtaaaggtgctaaagaaacgcaccaatggccctaagcagaatgatgtgttcac aacaacagtcactcttggaaccatctcgggccaaaatgacaatggtctaaccaggcaaattcgggtg cctttcaacccccttactttgtaagtcatctgacggtggttctaccacaccactgtcaataagggggttcaatg tatcaaatgtggaaggtgcttaaggcagagctacgtgcaacaccactaacagggggggcaaatgtg gttggttcagtcggcttcatggttctcaccctgaatgggctcgaagccactgcagattccatcgacacaa taaaagcaagaaagcacgtgcagattccgataggcagaagtgccgttcttcgtattcttgcacgcgact gtgcggggcctcgcgagggttggtggcttactgatacttcaagttccagctgacgcacatgggcctg cggtcgatctcatgatcgcctataaaacatcaaacttgcttaatgtgtcaagtaccactggacctcagcc ttttactggtaccttatggcaggcggagctcaaagtcacttatgcttttagcacctatgacccgaaacctg gtcttcagactcttgtgtcagagacgtatctggtagccatcaagttactattcaaacctcagcagacga cggttcacttataatgacaacaactgatacgcaactgctttcactccttacgccacgtacgggtgaccag aagaaggggaaatctccaactgtctgggcagttgcaggcgccgttgttgatgctgtagctcctgtattag gaccctggggctggctacttaaaggcggcttcttccttgttaggaagatcttcggggcttctactcggaat gcgggagcgtcttatcagatttacccctcaattgagcaggctatgtctgatcaaccaatttttggtcagca atctggaacaacacaagtgacactcccgcttgttcatgtttccgaggttatgaaccccaactccgagag taatgacctaaatccaacatctaggtcacttccacctaccccgcctactccatctactgatcccattcttcc cttggcggagctaactggacaaccgggggttccacccctctacacctttgacggcagtagctataccc cctcaactaactggttgggctctacaattctactcacaggtataccagcacataagagagttacaggta atctctcaaactttggagtaaccaatctccagatgtccaaagttacagctactgcacttgagatctatgatt tcacagactttggagtcttctttggaacaggaagctatctcggagaaggtggaatccccctggaacaa ccctgatccactccctaatgtctggccaaacaccaactcctccgccagcagcaaatcaatctggcaca acttggtacctgccatcgtgggcaggttttccaccacctggccagggcgactactttctccaaacgcag gatgtcaccgacacaacaactcacacgaccctcggttaatgtctactttctcgtggcctaccgccagtctc -continued gaaggcttacagctttctttaatacaggaggcacagctcgtccagcaccaacttcaatgctatgcctcta taatgttgactgtgggcgtgcaccacaaacgccctaccctacctttcagtcaactctccaaagcctgaat caaattggggtggatgcaaaacctgactccgactccgacgatgacatctcactggcggggtcatgcat tggcgacgagtttgagagtgtggatcaactcgaacgcgagagagaagatttaatgaggaggctaag agatctagacctccggcgctttcagatc, i) VF08-18/14:

(SEQ ID NO 19)

atggctggccctgccggctcgtccaatggggcgctcgcccaaaactcaaatggcaaaatctaaga aggctaagaaacctccatctcagaaaaagccttctcaaaaaccactcaggaaggaagtaaaaaag gtggaaagacaggtcaaggtgcttaagaaacgcaccaatggccctaagcagaatgatgtgtttacaa caacagtcactcttggaaccatctcgggccaaaatgataatggtctaaccaggcaaattcgggtgcctt tcaaccccttactgtgtaagtcatctgatggtggttccaccacaccactatcaataagggggttcgatgtac caaatgtggaaagtgcttaaagcagagcttcgtgcaacacctctaacaggaggggcaaatatagtcg gctcggtcggctttatggtcctcaccctgaatgggcttgaagccactgcagattctattgacacaataaa agcaaggaagcacgtgcagattccgattggcagaagtgccgttctgcgtattcttgcgcgtgattgtgct gggcctcgcgagggctggtggctaactgatacgtcaagctcaccggctgacgcttatggacccgcag tcgacccttatggttgcctacagaacatcaaacttgcttaacgtgtctagtgccagtacacagcctcaatct ttcactggtactctgtggcaggcagaacttaaagttacttatgcttttagcacctatgacccaaaacctggt cttcagactctcgtgtcagagacgctctccggcagccatcaagtcaccattcaagcttcagcagatgat ggttcacttataatgacaacaactgatacgcaactgctatcactcctttacgccacgtacgggtgaccag aagaagggcaaatctccaactgtctgggcagtcgctggtgctgttgttgatgctgtagcccctgtattag gaccatggggctggcttctcaaggtggcttttccttgttaggaaaatctttgggtttcatctcgtaatgc gggggcgtcttatcagatctacccttcaattgagcaagctatgtctgaccaaccaatctttggtcagcaat ctggaacaggtacacagattacgctcccacttgttcatgtctctgaggttatgaaccccaactccgaga gtaatgacctgtctgctccaacatctagggcgcttccacctgcacctgaaccagagcctgagctcccac tggcccctattagttggccagtccaacgtccctgcagtctatgagtacactggggatgcttatacaccaca accaaggtggacaggctcgaccatttttcctcactggtattccctaccatactagggctacaggtgctaca cagtcttttggagtgagaactaacaatatgtcaccttcaaactgcacaacacttgacatctatgacttcac aaattttggagtcttctttggcagtaatggctacctctcacaaggagccatacacacttcaagaacaatg attcactcactcaagactaatccgaatataaaccccttggctagcagcaaatcaatcttcaaccacgtgg tctatgcctacgtggtctggctatcctacaccaggccaaggagattacttcctgcaaatgcaagatacc actgattcaactacccatacaacatctgtgggttgctattttctggtgatgtatggtgaatctcggaaactta ttgcctttttttaacactggcactggcacagcaagacctgcactttcatctatgatgtgcctctataatgttgat gcaggaagagcaccagtgaggattcagggctttcttctcagcccatcacaaaattttgttgaaactgac aatcaggacccagaagatgatgatgacatctccatcgccgggtcctgtctgcaagatgagtttgattgt gtgggtcaactcgaaaagaaagagaagatctaatgaggaggttaagagatctagacctccggcgc tttcagatc, j) VF08-18/5:

(SEQ ID NO 20)

atgcctggccctgccggccctgccaatggggcgctcgcccaaaactcaaatggtaaaacctaag aaggccaagaaacctccacctcagaaaaagccttctcaaaaaccactcaggaaggaagtgaaga aggtggaaagacaggtaaaggtgcttaagaaacgcaccaatggccctaagcagaatgatgtgttca caacaacagtcactcttggaaccatctcgggccaaaatgacaatggtctaaccaggcaaatccgggt -continued gcccttcaaccccttactttgtaaatcatctgacggtggttctaccacaccactgtcaattaggggttcaat
gtatcaaatgtggaaggtgcttaaggcagagctacgtgcgacaccactaacaggggggcaaatgt
agtcggttcagtcggctttatggttctcaccctgaacgggctcgaagccactgcagactccattgacaca
ataaaagcaaggaaacatgtgcagattgcacttggcaggagtgctgctcttcgcattcttgcccgtgact
gcgcgggacctcgcgagggctggtggcttactgatacttctagttccccggctgactcttatgggcctgc
ggttgatcttatgatcgcctataaaacatctaacttgctcaatgtgtcaactgctggtatacctcaatcattta
ctggcacgctttggcaagtggagctcaaagtcacctatgcgtttagcacttacgatccaaaacctggtct
gcaaactcttgtttcgcagactctggatgggtctcatcaagtcacactccaacaatcaacaactgatgg
ctccctcataatgacaactactgatgccacccttctttctatccttaccccccgcgttgggggccaaggt
cgggaaagtctcaaacggtctggtcgattgcaggagctgcggttgaggctgctgccccgctgcttggtc
cgtggggctggcttcttaagggggcttttggcttgtgagaaaattttggtgcttccgcgcgtgacacg
acctcacagtaccaaatttatccttccattgagtctgcaatgtctgaccaaccaattttttggccagactggt
atttcaactgtcactctgcccattgtgcacatttccgaagtgatgaatcctaatcctgagaacaatgacct
gtctaatccaacttctaggtcacttccacctactccacctacccccacctgctcaggagaaaattctacca
cttactctccttgagggtcaaccaggtgttcctgccttatatacatttaaccccagcacggaagcctatac
agcagcaactggctggacaggggggacgctacttcttaccggcgtaccagagtacgaacttcgcag
cggctcctcacaacaatttggggtccgagtgactacctcaccaggtcttccaccagctgcagcaacat
cgatacaaatttatgattttacaaaatttggtatcttctttggtgctggtgcttttcttgggcaaggaggagtcc
atacagcaaagactcttctaacagcaattacatcttctagcaaccccccctggcttgcttgccacagata
cacctggagctggcctgattggcttgttacggctggttatcctaaacctgtggagggtggctggtggctgc
agatgcaaaaaattggtgataccacatctcatacaactccagttggtatctacttcctggtggcatataa
ggagatgcaacaacttgtggcttttggcacacgggttccggagcccaagccgaacccacttctcttat
gtgcctttataatgttgatgcagggcgtgcacctgtgagagttccgcacttcattcttacaactactgcccg
caatgaagtggaggttgatgggggtgatgactcagacgacgacatctctcttgctgggtcttgtgttggc
gacgagtttgagggtgtggatcaactcgaacgcgaaagggcagaacttatgagcaggttaagagac
ctggacctgcggcgctttcagatc, k) VF08-29a:
(SEQ ID NO 21)
atggctggcggtgccaccgcacctgcgggcgctaagcccaagcaacccaagcaaaagcagcaga
aaccttgttctcagcggaaaagaaaattccgcaaaaacagaagtccatgaaaccagtaaaacag
gagttgaggaaagttgagaagcaagtcaaggtccttaaagctcggacaaatggacccaaagtaaat
gatacaatgaagactacagtcacagtgggtacccttgtgggacaaacacaaagtggactcaaccgc
caacttagggtctcattcaatcctcttctcatgaagtcaacagatggcggtaatactactccactttccattc
gtgcttcaatgtacgagatgtggaaaccactgagtgtagagatctatgccacgccacttagtggcttttc
aagcgtggtaggttcagttggctttatggttcttactctgaatggacttgaggcttccgcagactcaattga
cactataaaggccaggaaacacgtccaaatggcgcttggtaggccttataggcttaaactaagtgctc
gtgaacttgctggtccccgtgaaggctggtggctcgttgatacatctgagtcgcctgccgatgcatacgg
cccagctgttgatctcatgctggcttatgcaacggaaaatctactcgggacatcctctggctccacaactt
catatacaggcacactctggcaagttgagatgagagttagctatgctttctccacctataacccaaaac
ctgggctgcagactctcatttcccaatccatcacgggtggtcagactgtaaccgttcaaccgtctccgga
cgatggctctctcattatgactactaccagtcaacaagtccttgcacttctaacacccagggtagcgggc -continued caaaagaagggcaaatcccagacaatttgggcaattgctggttcagcaattgatgctgccgctacagt
gcttggaccctggggctaccttttaaaaggtggcttctggcttgttcgacttatatttggtggaacgtctgct
agaaacccaacaacacgccagtatcagatttacccgtcggtcgagtcagctcttaccgaccaacctat
ttttggcaatgctactggcacccagagtgttactgttccaatctgccatattacagaagttgtgaatccaaa
tgcgggaaagcaacaatttcactggtccaacaaccaagtgcaccagcaccaccggtgcccccaa
ctccaattcaagatgtcattctaccactcgcagaattgactgggcaagatggagtgccagcaaactac
accttcaatggtgattcttatacagctcagtccgattggagggggtctacgcttgttctcactggaattcca
agacataagcgagtggccgggaacctgtccaattttggtgtggtgactaaccagatgtcaaaagtcac
cacaaccgcacttgagatatatgacttcaccgacttcgggatcttcttcggtggaggctaccaactccag
gaaggtggaatacatactggtaaaacactggtacactcgctcatgacaggtgctccaataaaaccttg
gctctatgctacccaatcatcaacaacctggtactggcctgattggactggcttcccaaaacctgggga
aggagactattttctccaagtgcaagatacaaccgatagaacaacacatacaacgtgtgttggtatcta
catcgttgttgcttatcgccagtcacgaaggttaatagccttctttaataatgcaggtccagtccgggcgg
cgcccacaactatgctttgtctatacaatgtggatgcgggccgagcaccagcaacaccttataacacct
tccaactcacactccaaagtgaaaactctgacccaaattctccatctgatgatgaagatgatgacatct
caattgctggctcctgtctccaagacgagtttgactgtgtggatcaactcgaaaagaaagagaagat
cttatgaggaggttaagagatctagacctccggcgctttcagagc,
or 1) VF08-29b:

(SEQ ID NO 22)
atggctggcggtgccaccgcacttgcgggcgctaagcccaaacaacccaaacagaagcagcaga
aacctggctctcagcggaaaaagaaacctccgcaaaaacagaaatgtatgaagccagttaaacag
gagctgaggaaagtcgaaaaacaagtcaaagtcctaaaggctcggacaaatggacctaaagttaat
gacacaatgaagaccacagtcacagtgggcactctggtgggacaaacacaaagtggacttaaccg
ccaactcagggtttctttcaacccgcttcttatgaagtcaacagatggcggtaacactactccactttccat
ccgtgcctcaatgtacgagatgtggaaagcactgagtgtagaaatctatgccacgccacttagtggtttt
tcgagcgtggtaggctcagttggctttatggtcctgacactgaatgggcttgaggcttccgcggattcaat
cgacaccatcaaggcaagaagacatgtccaaatggcacttggtaggccctataggttgaaactaaac
gcccgtgaactcgctggtccccgcgagggctggtggctggttgacacatctgagacgcctgccgaag
catacggcccggcagttgatcttatgctggcctatgcgacagaaaatctacttgggacgtcttctggctct
acaacttcatacacaggtacactctggcaagttgaaatgagggttagttatgcttctccacctacaatcc
aaaacctgggctgcaaactctcatttctcaacccatcactggtggccaaactgtgaccattcaaccgtct
ccggacgatggctcactcataatgactaccactagtcaacaagtccttgcactcctaacacctagggta
gcggcaggtcaaaagaagggcaaatcccaaacaatttgggcaattgccggttcagcagttgacgcc
gctgccacagtgctcggaccctggggctacctcctgaaggggtggtttctggctcgttcgactcatttttggt
gggggatctgccagaaacacaacaaccaggcagttccagatctacccgtcggtcgagtcagcactt
gccgaccagcctatttatggcaattctactggaacccagagtgttaccgttccaatttgccacatcactga
agttgtgaatccgaacgcggaaagtaataacctcactctcccacaacctcagcacctgcaccacca
acaccaccatcaccatctgaagacccccatactaccgctggcagaattaactggcagcctggggtcc
cacctctttacacttttgatggcagtagctatactccagcgcccaactggctggggtcaacactattacta
actgggataccagcacataaacgagtgactggtaatttggccaacttttggagttaccaacctccaaatg
tcaaaagttactgccactgcagttgagatctatgatttcacagattttggtgtgttctttggcactggcagctt -continued
```
ccttggcgaaggtggcattcacacagggaagactctgatctattccctgatgtctggtcaagacccaaa accctggctggcggcaaaccagtcaggaacaacctggtaccttccttcttggggttggttttcccacacca ggtgcgggtgactacttcctgcaaatgcaggacacaacagacacgacaactcacacaacatcagtg aatgtctactttctggttgcctaccgtcaatcacgtaggctgatcgctttcttttaacacaggggggcacagc aagaccagcgccaacatcaatgctctgcatgtacaacgtcgactgtgggcgtgctcctgcaacaccttt atcccacataccagtcggctctgcaatcaaaagttgaggtggctaattctgaaaccccttgactccgacg acgacatctcactggcgggtcatgcattggcgacgagtttgaaagtgtggatcaactcgaacgcga aagagaagatctaatgaggaggctcagagatctcgacctccggcgctttcacatc
```
or a fragment of any one of SEQ ID NO 1, 2, 3, 14, 15, 16, 17, 18, 19, 20, 21, or 22.

In embodiments there is provided at least one nucleic acid sequence selected from a sequence consisting essentially of or consisting of any one of SEQ ID NOs 1, 2, 3, 14, 15, 16, 17, 18, 19, 20, 21, and 22 or fragment thereof.

Suitably, a fragment of SEQ ID NO 1, 2, 3, 14, 15, 16, 17, 19, 20, 21 and 22 may not be present in the nucleic acid sequences encoding the capsid protein or ANV-1 or ANV-2.

Advantageously, the specific nucleic acid sequences of the invention can be used to identify particular ANV types which are present in a sample, typically a biological sample, most particularly a blood sample derived from an avian.

As indicated, each of the indicated nucleic acid sequences encode a capsid protein of an ANV type wherein a type has a particular antigenic determinant.

Accordingly, a fifth aspect of the present invention provides an amino acid sequence comprising at least one amino acid sequence selected from:

a) VF04-1/2:

(SEQ ID NO 4)
MPGPAGPANGGARPKTQMAKPKKAKKPPSQKKPSQQKPLRREIKKVEK

QVRVLKKRTNGPKQNDLFTTTVTLGTISGQSDNGLTRQIRLPLNPLLLKS

SDGGSTTPLSIRGSMYEMWKVIRAELIATPLTGGANIVGSVGFMVLTLNE

LEATADSIDSIKARKHVQIPLGRLARLRLTARECAGPREGWWLTDTSQSP

ADSYGPAVDLMIAYATTNLLNTSGGASATFLGTLWQVEIRVTYAFSTYNP

KPGLQTMVSQTLAGSNHQVTIQQSTTDGSLIMTTNDANLLSILTPRVAGQ

RSGKSQTVWAIAGAAVEAAAPLLGPVGWLLKGGFWLVRKIFGASARDT

TSQYQIYPSIEAAMSDQPIFGQTGTSTTVTLPIVHISEVMNPNPENNDLTN

PTARSLPPVPPAPSEDPILPLAELTGQDGVPANYTFNGDSYTGQADWRG

STLVLTGIPKHKRVAGSLANFGVVTNQMSKVTTTALEIYDFTDFGIFFGG

GYQLQEGGVHTGKTMVHSLMTGAPIKPWLYATQSSTTWYWPTWTGFP

QPGEGDYFLQMQDTTDRTTHTTCVSVYLLVAYRASRRLIAFYNNGGPVR

AAPTTMLCLYNVDAGRAPATPYNTFQLTLQSEGADPNSPSEDEDDDISL

AGSCLQDEFDCVDQLEKEREDLMRRLRDLDLRRFQI, b) VF07-13/7:

(SEQ ID NO 5)
MAGPAGSSNRGARPKTQMAKPKKAKKPPSQKKPSQKPLRKEVKKVER

QVKVLKKRTNGPKQNDVFTTTVTLGTISGQNDNGLTRQIRVPFNPLLCKS

-continued

SDGGSTTPLSIRGSMYQMWKVLKAELRATPLTGGANVVGSVGFMVLTL

NGLEATADSIDTIKARKHVQIPIGRSAVLRILARDCAGPREGWWLTDTSS

SPADAYGPAVDLMIAYKTSNLLNVSSTTGPQPFTGTLWQAELKVTYAFS

TYDPKPGLQTLVSETLSGSHQVTIQTSADDGSLIMTTTDTQLLSLLTPRT

GDQKKGKSPTVWAVAGAVVDAVAPVLGPWGWLLKGGFFLVRKIFGAST

RNAGASYQIYPSIEQAMSDQPIFGQQSGTTQVTLPLVHVSEVMNPNSES

NDLNPTARSLPPIPPAQEKILPLTLLEGQSGVPALYTFNSGTGAYTPMTR

WTGGTLLLTGVPEYELRSGSSQQFGVRVQNSPGLSPAAATSIQIYDFTK

FGIFFGAGEFLGQGGVHTAKTLLTAITASSNPPWLDCSRYTWSWPDWLT

SAGYPKPAQGDWWLQMQKVGDTTSHTTPVGIYFLIAYEEMQQLVAFWH

TGSGAQAEPTSLLCLYNVDAGRAPVRVPHFIITTTARNEVEVDGGDDSD

DDISLAGSCVGDEFEGVDQLERERAELMSRLRDLDLRRFQI, c) VF08-3a:

(SEQ ID NO 6)
MPGPAGPANGGARPKTQMAKPKKAKKPPSQKKPPQKPPRKEVKKVER

QVKVLKKRTNGPKQNDVFTTTVTLGTISGQNDNGLTRQIRVPFNPLLCKS

SDGGSTTPLSIRGSMYQMWKVLKAELRATPLTGGANIVGSVGFMVLTLN

GLEATADSIDTIKARKHVQIPIGRSAVLRILARDCAGPREGWWLTDTSSS

PADAYGPAVDLMVAYRTSNLLNVSSASTQPQSFTGTLWQAELKVTYAFS

TYDPKPGLQTLVSETLSGSHQVTIQTSADDGSLIMTTTDTQLLSLLTPRT

G DQKKG KSPTVWAVAGAVVDAVAPVLG PWGWLLKGGFFLVRKIFGVSA

RNAGASYQIYPSIEQAMSDQPIFGQQSGTTQVTLPLVHVSEVMNPNSES

NDLTPTSRALPPAPESEPELPLALLVGQAGVPAVYEYTGDAYTPQPRWT

GSTIFLTGVPYHTRATGATQSFGVRTNNMSPSNCTTLDIYDFTDFGVFFG

SNGYLSQGAIHTSKTMIYSLKTNPNINPWLAANQSSTTWSMPTWSGYPA

PGQGDYFLQMQDTTDTTTHTTSVGCYFLVMYGESRKLVAFFNTGTGTA

RPALSSMMCLYNVDAGRAPVRIQGFLLSPSQNFVETDNQDNDDDDDISL

AGSCLQDEFDCVDQLEKEREDLMRRLRDLDLRRFQI, d) ELV276CI5:

(SEQ ID NO 23)
MAGGATAPAGAKPKQSKQKQKNSSQRKSKTTQKVKQQKPPVKTVRRL
EHQVNALKKKTNGPKMNDMMKTTVTIGVIQGQTQSGLSRQLRVPLNPLL
MKSTEGLAATPLSIRSSCYELWKALHVELFATPLTGFSNVVGSVGFMALT
LNGLEATADSIDSIKARKHYQMALGRPARLKLTARELAGPREGWWLTDT
SESPADAYGPAIDLMIAYKTENLLNTTGSTTSTHTGPLWQIEARATYGFA
NYNPKPGLQTLVSQTLTNGQTVTIQPSPNDGSLIMTTTSLQVRSLLSPRA
GDPKKGKSQTIWAIAGSAVDAAATVLGPWGWLLKGGFWLVRQIFGGSS
NAAGSSYQIYSSLESAMADQPIFGAQTGTQSITVPVVHISEVLNPNPMSN
QVPTPSAGSAPAPPTPPTPIQDIILPLAELTGQDGVPANYTFNGDSYTGQ
GDWRGSTLVLTGIPRHKRVTGNLSNFGVTVNQMSKVTTTALEIYDFTDF
GVSFGGGYQLQEGGVHTGKTMVHSLMTGAPIKPWLYATQSSTTVVYWP
TWTGFPQPGPGDYFLQMDTTDRTTHTTCVSVYLLVAYQASRRLIAFYN
NGGTARAAPTTMLCLYNVDAGRAPQTPYNTFQLTLQSEVADPNSPSED
EDDDISLAGSCLQDEFDCVDQLEKEREDLMRRLRDLDLRRFQI, e) ELV276CI3:

(SEQ ID NO 24)
MAGGATAPAGAKPKQSKQKQKTPSQRKLKSTQKAKQQKPPVKTVRRLE
RQVNALKKKTNGPKMNDMMKTTVTIGVIQGQTQSGLSRQLRVPLNPLLM
KSTEGLAATPSIRSSCYELWKALHVELFATPLTGFSNVVGSVGFMALTL
NGLEATADSIDSIKARKHYQMALGRPARLKLTARELAGPREGWWLTDTS
ESPADAYGPAIDLMIAYKTENLLNTTGSTTSTYTGPLWQIEARVTYGFAT
YNPKPGLQTLVSQTLTNGQTVTIQPSPTDGSLIMTTNSLQIRTLLSPRAG
DPKKGKSQTIWAIAGSAVDAAATVLGPWGWLLKGGFWLVRLIFGGSTNA
TTSSYQIYSSLESAMADQPIYGAQTGTQSITVPVVHVSEVLNPNPVSNQV
PTPSTGSAPAPPTPPAPSEDPILPLAELTGQPGVPPLYTFDGSTYTPPTN
WLGSTLLLTGIPAHKRVTGNLANFGVTNLQMSKVTATAIEVTDFTDFGVF
FGTGTYLGEGGIHTGKTLVYSLMSGQTPNPWLAANQSGTTWYLPSWVG
FPTPGAGDYFLQMDVTDTTTHTTSVNVYFLVAYRESRRLIAFFNTGGT
ARPAPASMICMYNVDCGRAPQTPYPTFQSTLQPKDEVDNSQTPDDDDD
ISLAGSFIDEFDSVDQLEREREDLMRRLRDLDLRRFHI, f) Belgian ELV1:

(SEQ ID NO 25)
MAGGATAPAGAKPKQPKQKQKTSCQRKSKPTQKVKQQKPPVKTVRRL
ERQVNALKKKTNGPKMNDIMKTTVTLGVIQGQTQSGLSRQLRVPLNPLL
MKSTEGLAATPLSIRSSCYELWKALHVELFATPLTGFSNVVGSVGFMALT
LNGLEATADSIDSIKARKHYQMALGRPARLKLTARELAGPREGWWLTDT
SESPADAYGPAIDLMIAYKTENLLNTSGSTTSTYTGPLWQIEARVTYGFA
TYNPKPGLQTLVSQSLTNGQTVTIQPSPTDGSLIMTTNSLQIQSLLSPRV
DGPQKGKSQTIWAIAGSAVDAAATVLGPWGWLLKGGFWLVRLIFGSS
NAAGSSYQLYSSLESAMADQPIYGAQTGTQSITVPVVHISEVLNPSPMFN
QVSVPTTGSAPAPPTPPAPSEDPILPLAELTGQPGVPPLYTFDGSTYTPP

TNWLGSTLLLTGIPAHKRVTGNSANFGVTNLQMSKVTATAIEVYDFTDFG
VFFGTGTYLGEGGIHTGKTLVYSLMSGQTPKPWLAANQSGTTVVYLPSW
VGFPTPGAGDYFLQMDVTDTTTHTTSVNVYFLVAYRESRRLIAFFNTG
GTARPAPTSMICMYNVDCGRAPQTPYPTFQSTLQSKDEVDNSQTPDDD
DISLAGSFIGDEFDSVDQLEREREDLMRRLRDLDLRRFHI, g) VF05-1/5:

(SEQ ID NO 26)
MPGPAGPVNGGARPKTQMAKPKKAKKSPSQKKPSQQKPLRREIKKVEK
QVRVLKKRTNGPKQNDLFTTTVTLGTISGQSDNGLTRQIRLPLNPLLLKS
SDGGSTTPLSIRGSMYEMWKVIRAELIATPLTGGANIVGSVGFMVLTLNG
LEATADSIDSIKARKHVQIPLGRLARLRLTARECAGPREGWWLTDTSQSP
ADSYGPAVDLMIAYATTNLLNTSGGASATFLGTLWQVEIRVTYAFSTYNP
KPGLQTMVSQTLAGSNHQVTIRQSTTDGSLIMTTNDTNLLSILTPRVAGQ
RSGKSQTVWAIAGAAVEAAAPLLGPWGWLLKGGFWLVRKIFGASARDT
TSQYQIYPSIEAAMSDQPIFGQTGTSTTVTLPIVHISEVMNPNPENNDLSN
PTSRSFPPTPPTPSTDPILPLAELTGQPGVPPLYTFDGSTYTPPTNWLGS
TTLLTGIPAHKRVTGNLSNFGVTNLQMSKVTATAIEIYDFTDFGVFFGTGS
YLGEGGIHTGKTLIHSLMSGQTPNPWLAANQSGTTWYLPTWVGFPTPG
AGDYFLQMDVTDTTTHTTSVNVYFLVAYHQSRRLIAFFNTGGTARPAP
TSMLCLYNVDCGRAPQTPYPTFQSTLQSLTQSEVDAKTDPDSDDDISLA
GSVIGDEFDSVDHLEREREDLMRRLRDLDLRRFQI, h) VF08-3b:

(SEQ ID NO 27)
MPGPAGPANGGVRPKTQMAKPKKAKKPPSQKKPSQKPLRKEVKKVER
QVKVLKKRTNGPKQNDVFTTTVTLGTISGQNDNGLTRQIRVPFNPLLCKS
SDGGSTTPLSIRGSMYQMWKVLKAELRATPLTGGANVVGSVGFMVLTL
NGLEATADSIDTIKARKHVQIPIGRSAVLRILARDCAGPREGWWLTDTSS
SPADAHGPAVDLMIAYKTSNLLNVSSTTGPQPFTGTLWQAELKVTYAFS
TYDPKPGLQTLVSETLSGSHQVTIQTSADDGSLIMTTTDTQLLSLLTPRT
GDQKKGKSPTVWAVAGAVVDAVAPVLGPWGWLLKGGFFLVRKIFGAST
RNAGASYQIYPSIEQAMSDQPIFGQQSGTTQVTLPLVHSEVMNPNSES
NDLNPTSRSLPPTPPTPSTDPILPLAELTGQPGVPPLYTFDGSSYTPSTN
WLGSTILLTGIPAHKRVTGNLSNFGVTNLQMSKVTATALEIYDFTDFGVFF
GTGSYLGEGGIHTGKTLIHSLMSGQTPNPWLAANQSGTTWYLPSWAGF
PQPGQGDYFLQMDVTDTTTHTTSVNVYFLVAYRQSRRLIAFFNTGGTA
RPAPTSMLCLYNVDCGRAPQTPYPTFQSTLQSLNQIGVDAKPDSDSDD
DISLAGSCIGDEFESVDQLEREREDLMRRLRDLDLRRFQI, i) VF08-18/14:

(SEQ ID NO 28)
MAGPAGSSNGGARPKTQMAKSKKAKKPPSQKKPSQKPLRKEVKKVER
QVKVLKKRTNGPKQNDVFTTTVTLGTISGQNDNGLTRQIRVPFNPLLCKS
SDGGSTTPLSIRGSMYQMWKVLKAELRATPLTGGANIVGSVGFMVLTLN
GLEATADSIDTIKARKGVPIPIGRSAVLRILARDCAGPREGWWLTDTSSS
PADAYGPAVDLMVAYRTSNLLNVSSASTQPQSFTGTLWQAELKVTYAFS

TYDPKPGLQTLVSETLSGSHQVTIQASADDGSLIMTTTDTQLLSLLTPRT

GDQKKGKSPTVWAVAGAVVDAVAPVLGPWGWLLKGGFFLVRKIFGVSS

RNAGASYQIYPSIEQAMSDQPIFGQQSGTGTQITLPLVHVSEVMNPNSE

SNDLSAPTSRALPPAPEPEPELPLALLVGQSNVPAVYEYTGDAYTPQPR

WTGSTIFLTGIPYHTRATGATQSFGVRTNNMSPSNCTTLDIYDFTNFGVF

FGSNGYLSQGAIHTSRTMIHSLKTNPNINPWLAANQSSTTWSMPTWSGY

PTPGQGDYFLQMQDTTDSTTHHTTSVGCYFLVMYGESRKLIAFFNTGTGT

ARPALSSMMCLYNVDAGRAPVRIQGFLLSPSQNFVETDNQDPEDDDDIS

IAGSCLQDEFDCVGQLEDEREDLMRRLRDLDLRRFQI, j) VF08-18/5:
(SEQ ID NO 29)
MPGPAGPANGGARPKTQMVKPKKAKKPPPQKKPSQKPLRKEVKKVER

QVKVLKKRTNGPKQNDVFTTTVTLGTISGQNDNGLTRQIRVPFNPLLCKS

SDGGSTTPLSIRGSMYQMWKVLKAELRATPLTGGANVVGSVGFMVLTL

NGLEATADSIDTIKARKHVQIALGRSAALRILARDCAGPREGWWLTDTSS

SPADSYGPAVDLMIAYKTSNLLNVSTAGIPQSFTGTLWQVELKVTYAFST

YDPKPGLQTLVSQTLDGSHQVTLQQSTTDGSLIMTTTDATLLSILTPRVG

GQRSGKSQTVWSIAGAAVEAAAPLLGPWGWLLKGGFWLVRKIFGASAR

DTTSQYQIYPSIESAMSDQPIFGQTGISTVTLPIVHISEVMNPNPENNDLS

NPTSRSLPPTPPTPPAQEKILPLTLLEGQPGVPALYTFNPSTEAYTAATG

WTGGTLLLTGVPEYELRSGSSQQFGVRVTTSPGLPPAAATSIQIYDFTKF

GIFFGAGAFLGQGGVHTAKTLLTAITSSSNPPWLACHRYTWSWPDWLVT

AGYPKPVEGGWWLQMQKIGDTTSHTTPVGIYFLVAYKEMQQLVAFWHT

GSGAQAEPTSLMCLYNVDAGRAPVRVPHFILTTTARNEVEVDGGDDSD

DDISLAGSCVGDEFEGVDQLERERAELMSRLRDLDLRRFQI, k) VF08-29a:
(SEQ ID NO 30)
MAGGATAPAGAKPKQPKQKQQKPCSQRKKKIPQKQKSMKPVKQELRK

VEKQVKVLKARTNGPKVNDTMKTTVTVGTLVGQTQSGLNRQLRVSFNP

LLMKSTDGGNTTPLSIRASMYEMWKPLSVEIYATPLSGFSSVVGSVGFM

VLTLNGLEASADSIDTIKARKHVQMALGRPYRLKLSARELAGPREGWWL

VDTSESPADAYGPAVDLMLAYATENLLGTSSGSTTSYTGTLWQVEMRV

SYAFSTYNPKPGLQTLISQSITGGQTVTVQPSPDDGSLIMTTTSQQVLAL

LTPRVAGQKKGKSQTIWAIAGSAIDAAATVLGPWGYLLKGGFWLVRLIFG

GTSARNPTTRQYQIYPSVESALTDQPIFGNATGTQSVTVPICHITEVVNP

NAGKQQFHWSNNQVHQHHRCPPTPIQDVILPLAELTGQDGVPANYTFN

GDSYTAQSDWRGSTLVLTGIPRHKRVAGNLSNFGVVTNQMSKVTTTAL

EIYDFTDFGIFFGGGYQLQEGGIHTGKTLVHSLMTGAPIKPWLYATQSST

TWYWPDWTGFPKPGEGDYFLQVQDTTDRTTHHTTCVGIYIVVAYRQSRR

LIAFFNNAGPVRAAPTTMLCLYNVDAGRAPATPYNTFQLTLQSENSDPN

SPSDDEDDDISIAGSCLQDEFDCVDQLEKEREDLMRRLRDLDLRRFQS, l) VF08-29b:
(SEQ ID NO 31)
MAGGATALAGAKPKQPKQKQQKPGSQRKKKPPQKQKCMKPVKQELRK

VEKQVKVLKARTNGPKVNDTMKTTVTVGTLVGQTQSGLNRQLRVSFNP

LLMKSTDGGNTTPLSIRASMYEMWKALSVEIYATPLSGFSSVVGSVGFM

VLTLNGLEASADSIDTIKARRHVQMALGRPYRLKLNARELAGPREGWWL

VDTSETPAEAYGPAVDLMLAYATENLLGTSSGSTTSYTGTLWQVEMRVS

YAFSTYNPKPGLQTLISQPITGGQTVTIQPSPDDGSLIMTTTSQQVLALLT

PRVAAGQKKGKSQTIWAIAGSAVDAAATVLGPWGYLLKGGFWLVRLIFG

GGSARNTTTRQFQIYPSVESALADQPIYGNSTGTQSVTVPICHITEVVNP

NAESNNLTLPTTSAPAPPTPPSPSEDPILPLAELTGQPGVPPLYTFDGSS

YTPAPNWLGSTLLLTGIPAHKRVTGNLANFGVTNLQMSKVTATAVEIYDF

TDFGVFFGTGSFLGEGGIHTGKTLIYSLMSGQDPKPWLAANQSGTTWYL

PSWVGFPTPGAGDYFLQMQDTTDTTTHHTTSVNVYFLVAYRQSRRLIAFF

NTGGTARPAPTSMLCMYNVDCGRAPATPYPTYQSALQSKVEVANSETL

DSDDDISLAGSCIGDEFESVDQLEREREDLMRRLRDLDLRRFHI,
or a fragment of any one of SEQ ID NO 4, 5, 6, 23, 24, 25, 26, 27, 28, 29, 30, and 31.

Suitably a fragment of SEQ ID NO 4, 5, 6, 23, 24, 25, 26, 27, 28, 29, 30 and 31 may not be present in the amino acid sequence of the capsid of ANV-1 or ANV-2

In embodiments there is provided at least one amino acid sequence selected from a sequence consisting essentially of or consisting of any one of SEQ ID NO 4, 5, 6, 23, 24, 25, 26, 27, 28, 29, 30, and 31 or a fragment thereof.

Knowledge of a specific amino acid sequence for a capsid protein of a particular ANV type allows for the identification of a particular ANV type in a particular biological sample.

As indicated above, the inventors have determined representative nucleic acid and amino acid sequences and nucleic acid and amino acid sequences of particular ANV types. These allow for testing of ANV in a sample or use of a nucleic acid sequence or an amino acid sequence of the invention to mediate an immune response in an avian, each of which forms a separate aspect of the invention.

Accordingly a sixth aspect of the invention provides the use of an amino acid sequence which comprises (a) at least 80%, at least 85%, preferably at least 90%, preferably at least 93%, more preferably at least 95%, more preferably at least 98%, even more preferably at least 99%, and most preferably 100% sequence identity to at least one of SEQ ID NO 4, SEQ ID NO 5, and SEQ ID NO 6, (b) at least one of SEQ ID NO 23, 24, 25, 26, 27, 28, 29, 30, and 31, (c) a fragment of a) or b), or (d) a nucleic acid sequence that encodes any of (a) or (b) or (c)

to detect the presence of ANV in a sample.

According to a seventh aspect of the invention, there is provided the use of an amino acid sequence which comprises (a) at least 80%, at least 85%, preferably at least 90%, preferably at least 93%, more preferably at least 95%, more preferably at least 98%, even more preferably at least 99%, and most preferably 100% sequence identity to at least one of: SEQ ID NO 4, SEQ ID NO 5, and SEQ ID NO 6,
(b) SEQ ID NO 23, 24, 25, 26, 27, 28, 29, 30, and 31
(c) or a fragment of a) or b), or
(d) a nucleic acid sequence that encodes for any of (a) or (b) or (c), to mediate an immune response in an animal, preferably an avian.

In embodiments there is provided the use of an amino acid sequence comprising at least one of SEQ ID NO 4, 5 or 6 or a fragment thereof, to detect the presence of ANV in a sample or to mediate an immune response in an animal, preferably an avian.

In particular embodiments, an amino acid sequence of the invention or an amino acid sequence encoded by a nucleic acid sequence of the invention is capable of generating an immunogenic response in a chicken. The immunogenic response may be against at least one antigenic site provided by an amino acid sequence of the invention or as encoded by a nucleic acid of the invention.

In embodiments, there is provided the use of a nucleic acid sequence of SEQ ID NO 1, SEQ ID NO 2 or SEQ ID NO 3 or a fragment thereof or a variant thereof or an amino acid sequence according to SEQ ID NO 4, SEQ ID NO 5 or SEQ ID NO 6 or a fragment or variant thereof as the immunogenic determinant in a vaccine composition for use in treating ANV in an animal, in particular an avian, more particularly a chicken or turkey.

Vaccination, the induction of adaptive immunity, of broiler chickens is advantageous as vaccination can be used to control clinical disease. In embodiments, vaccination can involve the vaccination of parent birds. In this case, the progeny chicks will receive maternally derived antibodies, which can confer protective immunity against challenge with pathogens exhibiting the same antigens against which the antibodies are directed. During the early growing period of the broiler chickens, chicks produced from vaccinated parents are likely to be less susceptible to adverse clinical effects caused by pathogens exhibiting the same antigens against which the antibodies are directed. Vertical transmission of the ANV pathogen from parent to chick is also less likely to occur where the chick has acquired protective immunity to challenge with the pathogen. This may be of particular advantage as possibly the early infection of broiler chicks with vertically transmitted virus (in the embryo) may predispose the progeny chicks to more severe pathogenic effects than infection when the chick is older.

Mediation of the immune system and/or vaccination of an animal may be achieved by any suitable means using the nucleic acid sequences or amino acid sequences of the invention.

According to a eighth aspect of the present invention there is provided a composition including at least one nucleic acid sequence of the invention, or at least one amino acid sequence of the invention for use in mediating or generating an immune response in an animal.

Suitably, a composition of the present invention may comprise immunogenic derivatives and/or at least part of a virus with a nucleic acid or amino acid sequence according to the invention, including, for example, antigenic subunits or vectors able to express at least one nucleic acid sequence comprising one of SEQ ID NOs 1 to 3. For example the composition or vaccine may be a DNA vaccine. The composition or vaccine may provide for encoding of a polypeptide of the invention, for example a capsid protein of ANV, for example SEQ ID NOs 4, 5, or 6 or the like.

According to a ninth aspect of the present invention a vaccine composition can be provided which comprises a composition of the eighth aspect of the invention. In embodiments, combinations of nucleic acid sequences capable of being expressed, for example vectors including nucleic acid sequences of the invention may be used, for example compositions including combinations of at least two of SEQ ID NOs 1, 2, 3. In embodiments compositions can include combinations of at least three of SEQ ID NOs 1, 2, 3. In further embodiments vectors comprising nucleic acids encoding amino acid sequences or the amino acid sequences of capsid proteins from ANV-1 and ANV-2 can be provided in combination with any two, or three vectors capable of expressing SEQ ID NOs 1, 2, or 3.

In embodiments, combinations of amino acids of the invention may be provided in such compositions. For example SEQ ID NO 4, 5, or 6 or combinations thereof, optionally along with at least one of a capsid protein from ANV-1 or ANV-2 may be provided.

Derivatives of amino acid sequences of the present invention may be used to mediate an immune response. For example, an amino acid sequence of the invention coupled to a second molecule, for example an adjuvant, a coupling partner, an effecter molecule, a label, a drug, a toxin and/or a carrier or transport molecule may be provided. Techniques for coupling the amino acid sequences, for example polypeptides, of the invention to both peptidyl and non-peptidyl coupling partners are well known in the art.

Suitably a composition of the invention may comprise a pharmaceutical carrier or diluent, for example physiological saline, propylene glycol and the like. Suitably the composition may comprise an adjuvant, for example, Freund's incomplete adjuvant. A composition or vaccine composition comprises an effective dosage of the antigen, for example amino acid sequence of the invention to induce immunity in the vaccinated avian or animal against challenge by a virulent virus. Immunity is defined herein as the induction of a statistically significant higher level of protection in a population after vaccination compared to an unvaccinated group.

Method of Vaccination

Methods of vaccinating avians, using a specific composition of the invention, such that an immunologically effective amount of the composition can be provided to an avian are known to those of skill in the art. A composition may be delivered orally, parenterally, or intravenously. The dosage of the composition provided will typically take into account the age and/or weight and/or physical condition of the avian. In embodiments, the composition can be provided in drinking water, spray or as an aerosol. This can allow for mass vaccination of poultry such as, but not limited to, chickens and turkeys. A composition may be prepared as a live vaccine, which can be administered via drinking water or by a spray. A composition may be prepared as an attenuated virus which may be produced by growing the virus in embryos or cell culture. Such an attenuated virus could also be given by drinking water or spray.

A composition may be prepared as a dead or inactivated virus including a nucleic acid or amino acid sequence of the invention which can be administered by inoculation. The adjuvant used with inactivated virus will likely be important in order to maximise the immune response elicited.

A composition or vaccine composition may be prepared as a recombinant subunit vaccine. This approach may be adopted, for example, if live vaccines are not efficacious and if inactivated vaccines are too expensive to produce. A recombinant subunit vaccine may be based on expression of a capsid protein, for example an amino acid sequence of the invention, in particular an amino acid sequence selected from SEQ ID NO 4, 5 or 6 in *E. coli*, yeast, plant or insect cells infected by a recombinant baculovirus.

In such an embodiment at least part of any ANV with a nucleic acid sequence or amino acid sequence according to the present invention may be used to prepare the composition. Suitably, an amino acid sequence of the invention may be produced by recombinant DNA expression methodologies or by culturing the virus.

In particular embodiments a composition or vaccine composition of the present invention may comprise both at least one nucleic acid sequence of the invention or at least one amino acid sequence of the invention for example a nucleic acid sequence selected from SEQ ID NO 1, 2 or 3 or combinations thereof, or an amino acid sequence selected from SEQ ID NO 4, 5 or 6 or combinations thereof and an antigenic determinant from another pathogenic agent such as another chicken virus, such that a vaccine composition which generates an immune response against more than one pathogen is provided.

In one embodiment, the composition can comprise a vaccine vector wherein the vaccine vector is an avian virus such as, but not limited to, fowlpox or herpes virus of turkeys. Such vaccine vectors can carry the immunogenically important genes of ANV, for example genes encoding a capsid protein, for example at least one of SEQ ID NO 1, 2 or 3 and the expression of these genes inside the vaccinated chickens will elicit an immune response. This technique has been previously used in generating an immune response against proteins from Newcastle disease virus and avian influenza virus.

Antibodies with binding specificity to an amino acid sequence of the invention may be prepared. These antibodies form a separate aspect of the invention.

Accordingly, a tenth aspect of the present invention provides a binding member which specifically binds to an amino acid sequence of the invention or a fragment thereof. The binding member may be selected from the group comprising: a protein, a peptide, a peptidomimetic, a nucleic acid, a carbohydrate, a lipid, an aptamer and a small molecule compound.

In certain embodiments, the binding member is an antibody or an antibody binding fragment which specifically binds to at least one amino acid sequence of the invention, in particular an amino acid sequence comprising any one of SEQ ID NO 4, 5, or 6 or a fragment or variant thereof.

An amino acid sequence encoded by a nucleic acid sequence comprising SEQ ID NO 1, SEQ ID NO 2 or SEQ ID NO 3 or a variant or fragment thereof or an amino acid sequence comprising SEQ ID NO 4, SEQ ID NO 5 or SEQ ID NO 6 or a variant or fragment thereof may be used as an antigen to generate an antibody with binding specificity to an amino acid sequence comprising SEQ ID NO 4, SEQ ID NO 5 or SEQ ID NO 6 or a variant or fragment thereof.

In certain embodiments the antibody is selected from the group consisting of an avian, chimeric, synthetic, or in-vitro antibody which has binding specificity to an amino acid sequence of the invention, or a binding fragment derived from any of the same. In certain embodiments the antibody is an antibody binding fragment selected from the group consisting of a Fab, scFv, Fv, or dAb fragment. In certain embodiments, the antibody molecule comprises two complete heavy chains and two complete light chains, or an antigen-binding fragment thereof.

Polyclonal antibody sera may be produced through the use of an immunising preparation wherein the immunising preparation comprises an amino acid sequence encoded by any one of nucleic acid sequences SEQ ID NOs 1, 2 or 3 or an amino acid sequence comprising SEQ ID NOs 4, 5 or 6 or variants or fragments thereof to raise an immune response.

Suitably the invention may provide polyclonal antibodies which have binding specificity to at least one amino acid sequence of the invention, in particular at least one of SEQ ID NO 4, 5 or 6.

As will be understood by those of skill in the art, polyclonal and/or monoclonal antibodies may be isolated or substantially purified from the mixture in which they are provided. Such antibodies may be humanised or codon optimised as would be appreciated by a person of skill in the art.

In embodiments, the invention can provide monoclonal antibodies which have binding specificity to at least one amino acid sequence encoded by a nucleic acid sequence of the invention, in particular any one of SEQ ID NOs 1 to 3 or a fragment or variant thereof, or at least on amino acid sequence of the invention, in particular an amino acid sequence comprising any one of SEQ ID NOs 4 to 6 or a fragment or variant thereof.

Monoclonal antibodies may be generated using a hybridoma technique, for example, immunisation of a mouse with an amino acid sequence of the invention may be used to generate mouse monoclonal antibodies In embodiments the immunising preparation can be any one of; virus-specified synthetic peptide comprising an amino acid sequence of the invention, in particular an amino acid sequence comprising SEQ ID NO 4, 5 or 6, polypeptides produced by expression vectors etc; DNA expression plasmids encoding and/or expressing a nucleic acid sequence of the invention, for example any one of SEQ ID NO 1 to 3, or a fragment or variant thereof. After repeated challenge of an animal using the immunising preparation, portions of blood serum from the challenged animal may be removed and antigenically purified. The semi-purified sera may additionally be purified using chromatography, for example, a saccharide gel column and suitable buffer to separate the components of the sera according to molecular weight.

Illustrative examples of the methods of immunisation to provide monoclonal antibodies are provided below. As will be appreciated by those of skill in the art, suitable methods may involve a combination of one or more of such methods.

1) ANV comprising an amino acid sequence of a capsid protein with at least 80%, at least 85%, preferably at least 90%, preferably at least 93%, more preferably at least 95%, more preferably at least 98%, even more preferably at least 99%, and most preferably 100% sequence identity to at least one of SEQ ID NO 4, SEQ ID NO 5 or SEQ ID NO 6 can be purified from cell culture-grown virus, embryo-grown virus or virus present in infected avian faeces, for example chicken faeces, and used for immunisation of a suitable animal, for example a mouse, rabbit or chicken.

2) An animal, for example a mouse, may be immunised with recombinant amino acid sequence comprising at least 80%, at least 85%, preferably at least 90%, preferably at least 93%, more preferably at least 95%, more preferably at least 98%, even more preferably at least 99%, and most preferably 100% sequence identity to at least one of SEQ ID NO 4, SEQ ID NO 5 or SEQ ID NO 6, (As will be appreciated by those of skill in the art, a recombinant ANV capsid protein may be produced by expression of an ANV nucleic acid sequence according to the invention, for example SEQ ID NO 1, SEQ ID NO 2 or SEQ ID NO 3 in *E. coli*, yeast, plant or insect cells infected with a recombinant baculovirus).

3) An animal, for example a mouse, may be immunised with a DNA expression plasmid capable of expressing an ANV nucleic acid sequence of the invention, for example, a nucleic acid sequence, with at least 80%, with at least 85%, preferably at least 90%, preferably at least 93%, more preferably at least 95%, more preferably at least 98%, even more preferably at least 99%, and most preferably 100% sequence identity to at least one of SEQ ID NO 1, SEQ ID NO 2 or SEQ ID NO 3.

4) An animal, for example a mouse, may be immunised with a synthetic peptide comprising an amino acid sequence of the invention, for example comprising an amino acid sequence with at least 80%, with at least 85%, at least 90%, at least 93%, at least 95%, at least 98% at least 99% or 100% sequence identity to one of SEQ ID NO 4, 5 or 6.

Hybridoma cells may be prepared from spleens removed from the immunised animals, for example mice, and cloned cell cultures may be screened for their abilities to secrete virus-specific antibodies using an indirect immunofluorescence test (IIF test). Antibodies produced in an animal treated with an amino acid sequence of the present invention, for example any one of SEQ ID NOs 4, 5 or 6, may be isolated and used in an assay and/or for assay purposes.

Suitably antibodies with binding specificity to an amino acid sequence of the invention in particular SEQ ID NO 4, 5 or 6 may be used for the preparation of a diagnostic assay. In embodiments of the invention such assays may be used to detect ANV in samples, for example tissues, faeces and serum from avians suspected of being infected with the ANV. Enzyme immunoassays such as immunofluorescence assays, enzyme linked immunosorbent assays (ELISA) and immunoblotting can be readily adopted to accomplish detect of the antigen.

According to an eleventh aspect of the present invention there is provided a diagnostic assay for the detection of ANV in a sample from an asymptomatic subject at risk of developing ANV, the method comprising the steps of:
(i) contacting physiological material with a probe wherein said probe is selected from:
    (a) a nucleic acid sequence that is capable of hybridising to any one of SEQ ID NOs 1 to 3 or a variant or fragment thereof under stringent conditions,
    (b) an amino acid sequence encoded by a nucleotide sequence of any one of SEQ ID NOs 1 to 3 or a variant or fragment thereof, or
    (c) a binding member, for example an antibody or binding fragment thereof, with binding specificity to an amino acid sequence of the invention, for example to (b),
    (d) a nucleic acid sequence that is capable of hybridising to a 3'UTR region of ANV, preferably under stringent or highly stringent conditions, and
(ii) detecting a successful binding event between the probe and physiological material of the sample.

In embodiments a nucleic acid sequence that is capable of hybridising to a 3' UTR region of ANV can be selected from

```
Forward primer sequence -
acggcgagtagcatcgag,           (SEQ ID NO 8)
and

Reverse Primer sequence -
ccgaaagtgggcttttcatt          (SEQ ID NO 9)
```

In alternative embodiments a nucleic acid sequence that is capable of hybridising to a 3' UTR region of ANV can be

```
Forward primer -
gtaaaccactggytggctgact,       (SEQ ID NO 11)
(where y is c or t),
and Reverse primer -
cgaggccacggcgagta.            (SEQ ID NO 12)
```

In alternative embodiments a nucleic acid sequence that is capable of hybridising to a 3' UTR region of ANV can be a nucleic acid sequence comprising

```
                                     SEQ ID NO 32
aatgaaaagcccactttcgggagaaccaactttagcgcacaggagcgta ggttttagcaggctccaagttgcgtgagtggcggtttgattgacctacc accccattggtcccctagcacagccaaattagttgactatgcaatggt cccagctttcctgtaccctcgatgctactcgccgt (SEQ ID NO 32) (shown in 5' to 3' orientation)
or
                                     SEQ ID NO 33
tactcgccgtggcctcgggaaagtcagttgctgtagtcagccaaccagt ggtttac (SEQ ID NO 33) (shown in 5' to 3' orientation),
``` or a nucleic acid with at least 90%, at least 95%, at least 97%, at least 99% sequence identity to SEQ ID NO 23 or 33 wherein said nucleic acid can bind under stringent conditions to SEQ ID NO 7 or 10,
    or a fragment of SEQ ID NO 32 or 33 wherein said fragment can bind under stringent conditions to the selected target sequence SEQ ID NOs 7 or 10.

Suitably said probes may bind under highly stringent wash conditions. In embodiments SEQ ID NO 32 or 33 or a derivative nucleic acid or fragments thereof can be immobilised.

Nucleic acid probes can be suitably labelled, for example with a fluorescent reporter molecule. In embodiments, a probe can be labelled with a fluorescent reporter molecule and a quencher to form a Taqman-type probe. Taqman probes have a fluorescent reporter molecule at one end and a quencher molecule (capable of quenching the fluorescence of the reporter) at the other end. Suitably, during PCR, the probe may bind to the gene of interest and become cleaved by the polymerase, such that the reporter and quencher becomes physically separated and fluorescence increases. Alternatively, the probe may be designed to fold on to themselves to bring the reporter and quencher close together to minimise fluorescence when the probe binds to the nucleic acid of interest the probe becomes linear and the reporter and quencher separate increasing fluorescence.

In embodiments physiological material of a sample can include nucleic acid (RNA) or extracts from blood, embryo, tissue, and intestinal contents.

In embodiments the method can include the step of isolating a nucleic acid from a sample of physiological material suspected of containing ANV.

Use of Nucleic Acid Sequences to Detect ANV

The inventors have determined that the primer binding regions (shown in underlining) in the sequence of the 3'UTR of the G4260 strain of the serotype 1 ANV are found in all ANV sequence variants they have studied.

(SEQ ID NO 7)
<u>acggcgagtagcatcgaggg</u>tacaggaaagctgggaccattgcatagtc aactaatttggctgtgctaggggggaccaatggggtggtaggtcaatcaa accgccactcacgcaacttggagcctgctaaaacctacgctcctgtgcg ctaaagttggttctc<u>ccgaaagtgggcttttcatt</u>.

This 182 bp nucleotide selected target sequence is provided in the 3' untranslated region (UTR) downstream of the open reading frame (ORF2) for the capsid protein.

Alternatively a selected target sequence for primer binding comprises a sequence within the 3' untranslated region (UTR) of ANV-1 (G4260 strain) (SEQ ID NO 10)

(SEQ ID NO 10)
<u>gtaaaccactggttggctgact</u>acagcaactgactttc<u>ccgaggccacg</u>

<u>gcgagta</u>

In embodiments a forward primer (SEQ ID NO 11), a reverse primer (SEQ ID NO 12) and an internal probe (SEQ ID NO 13) with binding specificity to SEQ ID NO 10 which may be used in real-time Taqman RT-PCR test are provided.

```
Forward primer -
gtaaaccactggytggctgact,      (SEQ ID NO 11)
(where y is c or t)

Reverse primer -
cgaggccacggcgagta            (SEQ ID NO 12)

Internal probe -
cagcaactgactttc              (SEQ ID NO 13)
```

The oligonucleotide primer sets are considered to be specific aspects of the invention. In embodiments, more than one primer set can be used in the assay method. Suitably the present invention provides a kit comprising primer sets which are complementary to or can bind under stringent conditions to SEQ ID NO 10 or SEQ ID NO 7. In embodiments primers can comprise nucleic acids which are complementary to SEQ ID NO 11 and 12 may be provided. In preferred embodiments the kit further comprises nucleic acid sequences which comprise SEQ ID NO 13 or are complementary to SEQ ID NO 13.

The invention further relates to an immobilised nucleic acid which can hybridise, under stringent conditions or highly stringent conditions to one of SEQ ID NO 7 or SEQ ID NO 10 or a fragment thereof. In embodiments, the nucleic acid probe can form of a stable duplex with SEQ ID NO 7 or SEQ ID NO 10 or a fragment thereof under stringent conditions, or highly stringent conditions. Generally a nucleic acid can hybridise to SEQ ID NO 7 or SEQ ID NO 10 when it is complementary to SEQ ID NO 7 or SEQ ID NO 10 or wherein said sequence has 90% or greater homology to such a complementary sequence.

In embodiments, an immobilised nucleic acid which can hybridise to SEQ ID NO 7 can be SEQ ID NO 32 or a fragment thereof.

In embodiments relating to a fragment of SEQ ID NO 32, the fragment is of a length which allows binding specificity to SEQ ID NO 7 under stringent, preferably highly stringent conditions.

In embodiments an immobilised nucleic acid which can hybridise to SEQ ID NO 10, under stringent or highly stringent conditions can be SEQ ID NO 33 or a fragment thereof.

In embodiments relating to a fragment of SEQ ID NO 33, the fragment is of a length which allows binding specificity to SEQ ID NO 10, under stringent or highly stringent conditions.

As indicated above, SEQ ID NO 7 is the sequence of the 182 bp amplicon that would be generated with the G4260 strain of ANV-1 using primers disclosed herein. SEQ ID NO 32 could be advantageously used to detect ANV-1 and sequence variants like ANV-1.

In particular embodiments, suitable primer sites or internal probes can be selected which bind to a selected 3'UTR target sequence with suitable hybridisation properties, to allow RT-PCR or real time RT-PCR to be used, for example to quantify the amount of virus RNA present. Suitable PCR cycle conditions, which includes the denaturing, annealing and extension temperatures and durations, would be known to those of skill in the art.

Suitably, the quantity of virus RNA present may be used to determine the level of virus load. It is possible that viral infections with no clinical signs may be characterised by low virus load, whereas clinically severe virus infections may be characterised by high viral loads. The ability to quantify the amount of virus RNA present is thus advantageous.

Use of Antibodies to Detect ANV in a Sample

In embodiments of the assay, an antigen, for example an amino acid sequence encoded by SEQ ID NO 1, SEQ ID NO 2 or SEQ ID NO 3 or a variant or fragment thereof or an amino acid sequence according to the invention for example comprising SEQ ID NO 4, SEQ ID NO 5 or SEQ ID NO 6 or a variant or fragment thereof can be used to detect antibodies in a sample which have binding specificity to ANV.

In embodiments, an amino acid sequence encoded by SEQ ID NO 1, SEQ ID 2, SEQ ID NO 3, SEQ ID NO 14, SEQ ID NO 15, SEQ ID NO 16, SEQ ID NO 17, SEQ ID NO 18, SEQ ID NO 19, SEQ ID NO 20, SEQ ID NO 21, or SEQ ID NO 22 or an amino acid sequence comprising SEQ ID NO 4, SEQ ID NO 5, SEQ ID NO 6, SEQ ID NO 23, SEQ ID NO 24, SEQ ID NO 25, SEQ ID NO 26, SEQ ID NO 27, SEQ ID NO 28, SEQ ID NO 29, SEQ ID NO 30, or SEQ ID NO 31 can be used to detect antibodies in a sample which have binding specificity to particular ANV types.

In one embodiment the diagnostic assay can comprise the steps:

(i) providing an immobilised amino acid sequence according to the present invention or an amino acid sequence encoded by a nucleic acid sequence encoded by the present invention, (ii) contacting physiological material, for example blood/serum, which may contain antibodies with binding specificity to ANV to said immobilised amino acid sequence, and (iii) detecting the binding of antibodies with binding specificity to ANV to said immobilised amino acid sequence.

The diagnostic assay may further comprise the step of providing an antigen of ANV-1 or ANV 2 or a binding member with binding specificity to ANV-1 or ANV-2 and detecting the presence of antibodies in the sample with binding specificity to ANV-1 or ANV-2 or detecting the presence of antigens of ANV-1 or ANV-2 in the sample respectively.

The assay method may comprise providing at least two immobilised amino acid sequences of the present invention, for example two amino acid sequences selected from SEQ ID NO 4, 5 and 6. In preferred embodiments the assay method comprises providing at least one, preferably 2 or 3 immobilised amino acid sequence selected from SEQ ID NO 4, 5 and 6 and at least one or preferably both amino acid sequence of a capsid protein of ANV-1 and ANV-2.

In another embodiment, a diagnostic assay method can comprise the steps;
(i) providing an immobilised binding member, for example an antibody, of the invention, for example with binding specificity to an amino acid sequence according to the present invention or an amino acid sequence encoded by a nucleic acid sequence of the present invention,
(ii) contacting physiological material, for example faeces containing ANV, to said immobilised antibody, and
(iii) detecting the presence of ANV present in the physiological material bound to the immobilised binding member.

Suitably, an immobilised binding member may be at least one binding member with binding specificity to at least one amino acid sequence encoded by SEQ ID NO 1, SEQ ID 2, SEQ ID NO 3, SEQ ID NO 14, SEQ ID NO 15, SEQ ID NO 16, SEQ ID NO 17, SEQ ID NO 18, SEQ ID NO 19, SEQ ID NO 20, SEQ ID NO 21, or SEQ ID NO 22 or an amino acid sequence comprising SEQ ID NO 4, SEQ ID NO 5, SEQ ID NO 6, SEQ ID NO 23, SEQ ID NO 24, SEQ ID NO 25, SEQ ID NO 26, SEQ ID NO 27, SEQ ID NO 28, SEQ ID NO 29, SEQ ID NO 30, or SEQ ID NO 31

Alternatively, the assay method can comprise providing at least one, at least two or three immobilised binding member(s), for example an antibody, with binding specificity to an amino acid sequence of the invention for example with binding specificity to at least one of SEQ ID NO 4, 5 or 6.

In embodiments, the assay method can comprise providing at least one or two immobilised binding members with binding specificity to an amino acid sequence selected from SEQ ID NO 4, 5 or 6 and at least one further binding member with binding specificity to a capsid protein selected from ANV-1 or ANV-2.

In particular preferred embodiments the method comprises providing immobilised binding members with respective binding specificity to each of the amino acid sequences comprising SEQ ID NO 4, 5 and 6 and capsid proteins of ANV-1 and ANV-2.

By contacting is meant to bring into close proximity thereby permitting the binding member or probe and protein or nucleic acid to interact. By detecting is meant determining if, for example, a specific nucleic acid, protein or binding member is present in a sample by determining if a binding event has occurred in the sample.

The captured virus may be detected through the use of a binding member, for example an antibody, with binding specificity to the virus, the binding member being provided in conjugated form as would be known to those of skill in the art.

In embodiments, the step of detecting can use at least one probe wherein the probe comprises a detectable label. Suitably the detectable label may be selected from, for example, a fluorescent marker, a radioisotope marker or the like.

Any suitable sample may be used in an assay of the present invention, for example, a sample from an avian, for example a chicken, may be used. Suitably, a tissue where the virus replicates may be used in such an assay. The sample may be blood or faeces. Preferably a sample for diagnosis may be selected from faeces, gut contents, a faecal swab, kidney and chicken embryo material.

Suitably, for example, when the sample is faeces and/or gut contents, crude virus suspensions may be prepared as 10% homogenates in phosphate buffered saline (PBS). These may be clarified using 3000 g for 30 minutes and an aliquot (eg 200 microlitre) of clarified extract can be extracted. With swabs, suspensions in 1-2 ml PBS may be made and clarified as above prior to extraction/analyses. With kidney, 10% tissue homogenates may be prepared in PBS, and be used clarified as above or remain unclarified prior to extraction/analyses. Homogenates (10% in PBS) can also be prepared from early dead whole embryos (days 1-5 post incubation) or tissues including kidney, liver and intestines recovered from late-dead embryos, and be clarified as above or remain unclarified prior to extraction/analyses.

In embodiments, physiological material can include genetic material from an avian, for example RNA from an avian, for example a chicken. In particular embodiments, genetic material may be taken from feathers, eggs including dead in shell embryos, blood, faeces, intestines, and intestinal contents, tissue including kidney or the like from an avian.

A number of commercial kits are available to extract RNA from tissue samples. These are well known to those skilled in the art.

According to a twelfth aspect of the present invention there is provided a diagnostic kit for use in the diagnosis of ANV, which includes a probe wherein said probe is at least one of
(a) a nucleic acid sequence that is capable of hybridising to any one of SEQ ID NOs 1 to 3 or a variant or fragment thereof under stringent conditions,
(b) an amino acid sequence encoded by a nucleic acid sequence wherein the nucleic acid sequence has at least 80%, at least 85%, preferably at least 90%, preferably at least 93%, more preferably at least 95%, more preferably at least 98%, even more preferably at least 99% and most preferably 100% sequence identity to a nucleic acid sequence comprising any one of SEQ ID NOs 1 to 3
(c) a binding member with binding specificity to an amino acid sequence of (b),
(d) an oligonucleotide sequence with binding specificity to a selected 3' UTR target sequence of ANV.

In embodiments an oligonucleotide sequence can be

```
Forward sequence -
acggcgagtagcatcgag,        (SEQ ID NO 8)

Reverse sequence -
aatgaaaagcccactttcgg       (SEQ ID NO 9)
```

In alternative embodiments, an oligonucleotide sequence can be

```
Forward sequence -
gtaaaccactggytggctgact,    (SEQ ID NO 11)

Reverse sequence -
cgaggccacggcgagta.         (SEQ ID NO 12)
```

In alternative embodiments an oligonucleotide sequence can comprise SEQ ID NO 32 or 33 or an oligonucleotide with at least 90%, at least 95%, 97%, or 99% sequence identity thereto or a fragment of SEQ ID NO 32 or SEQ ID NO 33 wherein said fragment can bind under stringent, or highly stringent conditions to the selected target sequence SEQ ID NOs 7 or 10.

Alternatively, a probe may comprise SEQ ID NO 7 or SEQ ID NO 10 or a fragment thereof which can hybridise to a cDNA transcript of the RNA virus under stringent or highly stringent conditions.

In embodiments, the oligonucleotide can be selected from any of SEQ ID NOs 8, 9, 11, 12, or 13 or an oligonucleotide with at least 90% sequence identity to the corresponding oligonucleotide sequences which can bind under stringent conditions to a selected target sequence selected from SEQ ID NO 7 or SEQ ID NO 10.

In embodiments of the kit, SEQ ID NO 32 or 33 or a fragment thereof are provided immobilised to a substrate. In embodiments an immobilised nucleic acid comprising or consisting of SEQ ID NO 32 or 33 or fragments thereof can be provided for use in microarray based diagnostic kits.

Diagnostic kits may use cDNA prepared from RNA extracted from a diagnostic sample. In embodiments hybridisation of the cDNA to an immobilised probe sequence can be detected using a fluorescent marker. A positive signal of binding of the cDNA to the immobilised sequence indicates that ANV is present in the diagnostic sample.

In embodiments, cDNA may be generated from the 3' UTR RNA of the virus and said cDNA immobilised and probes used to bind to said cDNA.

In embodiments of the diagnostic kit, a probe, for example an oligonucleotide or nucleic acid sequence of the invention, can be associated with a marker, for example a fluorescent marker, a radioisotope marker or the like.

Suitably, in embodiments of the kit a probe can be an amino acid sequence selected from SEQ ID NO 4, 5, 6, 23, 24, 25, 26, 27, 28, 29, 30, or 31 or a binding member with binding specificity to any of said amino acids.

In particular embodiments the diagnostic kit can include components required for an immunohistochemical test, a cryostat section fluorescent antibody test, a tissue impression smear fluorescent antibody test, an in situ hybridization test or the like. In embodiments, the kit can optionally comprise other components useful for amplifying and detecting nucleic acid targets, for example, enzymes (DNA polymerase, RNA polymerases, reverse transcriptases, RNases etc), buffers, control templates, and the like.

A diagnostic test for detection of antibodies to multiple ANV types may utilise antigens from all five representative ANVs (capsid proteins from ANV-1, ANV-2 and amino acid sequences comprising SEQ ID NOs 4, 5 and 6). Alternatively, detection of ANVs in tissues by cryosection fluorescent antibody test or in faeces by antigen capture ELISA may utilise an antiserum with a very broad range of specificity, for example this antiserum could be raised against antigens from ANV-1, ANV-2, and amino acid sequences comprising SEQ ID NO 4, 5 and 6. In embodiments of a diagnostic test aimed at detecting a specific antigenic ANV type then a specific antigen or binding member with binding specificity to a specific antigen of an ANV type, for example an amino acid sequence of the invention, can be used.

Knowledge of variable regions and conserved regions in different ANV types is useful, as knowledge of variable regions in the amino acid capsid sequences may be used to generate specific antibodies (monoclonal or polyclonal) which are able to differentiate ANV antigenic types. The ability to differentiate ANV types by antibody staining (for example in tissues with fluorescent antibody reagents) may be useful in diagnosis and in epidemiology investigations, where the spread of a particular ANV type may be followed even if other ANV types were present.

Suitably, knowledge of conserved regions may allow the generation of binding members, for example antibodies, that would have binding specificity to all identified ANV types.

According to a thirteenth aspect of the present invention there is provided a gene construct including at least one nucleic acid sequence of the invention and a control sequence, for example a promoter.

According to a fourteenth aspect of the present invention there is provided a vector including an isolated nucleic acid sequence of the invention and a promoter which is operably linked to said nucleic acid sequence. Suitable vectors include viruses (eg. Vaccinia virus, adenovirus, baculovirus etc), yeast vectors, phage, chromosomes, artificial chromosomes, plasmids or cosmid DNA.

According to a fifteenth aspect of the invention there is provided a method of producing a polypeptide encoded by a nucleic acid sequence of the invention, or fragment thereof, including the steps of:

(a) contacting a bacterial cell and/or an insect cell via a baculovirus and/or a yeast cell and/or a plant cell with a vector according to the fourteenth aspect of the invention, and (b) cultivating said bacterial cell and/or an insect cell and/or a yeast cell and/or a plant cell under conditions suitable for the production of polypeptide or fragment thereof.

In embodiments, the bacterial cell can be *Escherichia coli*.

In embodiments, the polypeptide can be encoded by a nucleic acid sequence of any one of SEQ ID NOs 1 to 3 or a fragment or variant thereof. Suitably the polypeptide may be encoded by a nucleic acid sequence of at least one of SEQ ID NOs 1 to 3. The invention further provides an amino acid sequence, for example a polypeptide produced substantially from the above method. As will be understood by those of skill in the art such an amino acid may be isolated or substantially purified from the mixture in which it is expressed.

A nucleic acid sequence, amino acid sequence or antibody of the invention may be used to generate an immune response in an avian. Such generation of an immune response may be used to treat an avian.

In various further aspects, the present invention extends to the use of a peptide comprising at least one of the amino acid sequences of the invention, for example comprising SEQ ID NO 4, SEQ ID NO 5 SEQ ID NO 6, or a variant or fragment thereof in a method for generating a binding member which specifically binds to an ANV capsid protein for use in the treatment of disease in avians.

Work with human astroviruses has shown that the astrovirus capsid proteins are proteolytically processed into 2 or 3 component proteins, with a protein approximating to an N-terminal part of the protein forming the inside of the capsid protein and a component protein derived from the C-terminal part forming the outside of the capsid protein and hence close to the surface of the virion.

Without wishing to be bound by theory, the inventors consider that the ANV capsid proteins can be considered to include an N-terminal part and a C-terminal part wherein the approximate N-terminal part of the ANV capsid is considered to be residues 1-346 of the ANV-1 capsid protein and comparable regions in the capsid proteins of other ANVs up to and including the tryptophan residue at residue position 344 in the ANV-1 sequence and the approximate C-terminal part of the ANV capsid is considered to comprise the remaining residues; in the case of ANV-1 the C-terminal part comprises residues 345 to 683. Comparison of N- and C-terminal parts of the capsid protein of the ANVs considered by the inventors indicated that these can display very different identities from one another. In particular embodiments an ANV capsid protein of the invention or a nucleic acid encoding such an ANV capsid protein can have an amino acid sequence identity of 90% or more to the C-terminal part or the N-terminal part of ANV 1, but less than 85% sequence identity to the whole amino acid sequence.

The inventors have determined that the capsid protein sequences of the 3 novel representative ANV sequences (SEQ ID NOs 4, 5 and 6) share different amino acid identities within the N- and C-terminal parts when compared one with another. Thus, the N-terminal parts of VF07-13/7 (SEQ ID NO 5) and VF08-3a (SEQ ID NO 6) were 98% identical, whereas their C-terminal parts shared 60% identity. Similarly the VF07-13/7 (SEQ ID NO 5) and VF08-3a (SEQ ID NO 6) ANV types showed 78 and 79% amino acid identity with the VF04-1/2 (SEQ ID NO 4) ANV in their N-terminal parts, but 52 and 63% in their C-terminal parts. Conversely ANV-2 and VF04-1/2 (SEQ ID NO 4) shared relatively low (62%) amino acid identity in their N-terminal parts and substantially higher (83%) in their C-terminal parts.

TABLE 1

Pairwise amino acid comparisons of N and C terminal parts of capsid proteins

| | ANV-1 | ANV-2 | VF04-1/2 | VF07-13/7 | VF08-3a |
|---|---|---|---|---|---|
| ANV-1 | — | 73 | 66 | 65 | 65 |
| ANV-2 | 69 | — | 62 | 62 | 62 |
| VF04-1/2 | 69 | 83 | — | 78 | 79 |
| VF07-13/7 | 52 | 49 | 52 | — | 98 |
| VF08-3a | 63 | 60 | 63 | 60 | — |

N terminal part comparisons in top right; C terminal part comparisons in bottom left.

Chimeric Clones

According to a further aspect of the present invention there is provided a method of generating an infectious clone wherein the clone comprises a capsid protein wherein the C-terminal part of the capsid protein is encoded by a nucleic acid sequence of a first ANV type and a N-terminal part of the capsid protein is encoded by a nucleic acid sequence part derived from a different ANV antigenic type, for example combinations of portions of SEQ ID NO 1, 2 or 3, a nucleic acid encoding a capsid protein of ANV-1 or ANV-2.

According to a further aspect of the present invention, there is provided a nucleic acid construct encoding a capsid protein wherein the nucleic acid construct comprises a nucleic acid sequence encoding a capsid protein from more than one ANV type, for example a combination of parts of a nucleic acid sequence encoding the capsid proteins of any one of ANV-1 or ANV-2 and a part of the nucleic acid sequence of any one of SEQ ID NOs 1 to 3. The present invention also relates to chimeric capsid proteins provided by such constructs. Such chimeric capsid proteins can be used as vaccines or diagnostic antigens, for example after baculovirus expression in insect cells.

The inventors have also established that particular regions of the capsid proteins of the ANVs studied are more variable than the rest of the sequence. It is believed that these regions are likely to correspond to regions of antigenic variability. This means that peptides based on such variable regions of the sequence may be particularly useful for producing antibodies that are specific to each of the novel ANV types.

In embodiments a nucleic acid construct can comprise an arrangement of nucleic acid sequences which are considered to form variable sequences of the ANV types as indicated herein, wherein the arrangement is novel i.e. not found in natural ANV types.

For example, a nucleic acid construct may provide an infectious clone including a C-terminal part derived from ANV-1 and an N-terminal part derived from SEQ ID NO 1. The production of an infectious ANV clone with a capsid protein from a single ANV type has been described in the literature with the G4260 serotype 1 ANV (Imada et al. 2000, J Virology 74: 8487-8493). Similar techniques may be used to provide infectious ANV clones with chimeric capsid proteins, wherein the chimeric capsid proteins are formed from portions of a capsid protein from more than one identified ANV or ANV type for example chimeric capsid proteins comprising at least a part of an amino acid sequence of SEQ ID NO 4, 5 or 6.

Definitions

As used herein, the term "isolated" refers to an in vitro preparation, isolation and/or purification of a peptide, polypeptide, protein, antibody, virus or nucleic acid molecule of the invention, such that it is not associated with in vivo substances or is substantially purified from in vivo substances.

As used herein the terms "nucleic acid sequence" or "nucleotide sequence" includes genomic DNA, cDNA or RNA.

Sequence identity—in relation to nucleic acid sequences provided by the invention, sequence identity is determined using a suitable mathematical algorithm. Computer implementations of such mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version8 (available from Genetics Computer Group (GCG), 575 Science Drive, Madison, Wis., USA).

Suitably alignments using these programs may be performed using the default parameters.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection.

When percentage of sequence identity is used in reference to amino acid sequences it will be understood by those of skill in the art that residue positions which are not identical often differ by conservative amino acid substitutions, i.e. wherein amino acids are substituted with amino acids which have similar chemical properties to those amino acids which are replaced. The percent sequence identity may be adjusted upwards to correct for the conservative nature of a substitution.

Hybridisation as discussed herein refers to the binding, duplexing, or hybridizing of a nucleic acid sequence to another nucleic acid sequence. These conditions are typically classified by degree of "stringency" of the conditions under which hybridization is measured.

Stringent hybridisation occurs when a nucleic acid binds a target nucleic acid with minimal background. Typically, to achieve stringent hybridisation, temperatures of around 1° C. to about 20° C., more preferably 5° C. to about 20° C. below the Tm (melting temperature at which half the molecules dissociate from their partner) are used. High stringency" at about 5-10° below the Tm; "intermediate stringency" at about 10-20° below the Tm of the probe; and "low stringency" at about 20-25° below the Tm. Alternatively, or additionally, stringency is defined by ionic strength and pH of the solution. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

An example of highly stringent wash conditions is 0.15 M NaCl at 72° C. for about 15 minutes. An example of a stringent wash condition is a 0.2× sodium chloride and sodium citrate (SSC) wash at 65° C. for 15 minutes (see, Sambrook and Russell, infra, for a description of SSC buffer for example 20×SSC made by dissolving 175.3 g of NaCl and 88.9 g of sodium citrate in 800 ml distilled water. Adjusting pH to pH7.0 with HCl (1M) and adjusting volume to 1 L with distilled water.). Often, a high stringency wash is preceded by a low stringency wash to remove background probe signal. An example of a medium stringency wash for a duplex of, for example, more than 100 nucleotides, is 1×SSC at 45° C. for 15 minutes. An example of a low stringency wash for a duplex of for example more than 100 nucleotides, is 4-6×SSC at 40° C. for 15 minutes. For short probes (for example about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (for example, >50 nucleotides).

By "complementary" it is meant a nucleic sequence in which all the bases or substantially all the bases are able to form base pairs with a sequence of bases in a second nucleic acid. Suitably, said complementary nucleic acid sequences may remain bound to each other under stringent, or highly stringent wash conditions.

An antibody may be natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and diabodies.

An avian may be a chicken, turkey, duck, quail, goose, ostrich, pheasant, peafowl, guinea fowl, pigeon, swan, emu, bantam and/or penguin.

By the term treat or treatment it is meant any regimen that can benefit an avian. The treatment may be in respect of an existing condition or may be prophylactic (preventative treatment). Treatment may include curative, alleviation or prophylactic effects. Such treatment may be provided via any suitable route. The precise dose of treatment will depend upon a number of factors, for example the precise nature of the antigen of the vaccine or the use of particular adjuvants.

As defined herein, the term "specifically binds", "binds specifically" or "binding specificity" refers to the ability of binding member, for example an antibody or fragment thereof to bind to an amino acid sequence of the invention, in particular an amino acid sequence comprising or consisting of a sequence selected from SEQ ID NO 4, 5 or 6 with greater affinity than it binds to an amino acid sequence not of the invention. In certain embodiments specific binding refers to binding to a target epitope present on an ANV type with a capsid protein comprising an amino acid sequence of the invention with an affinity which is at least 10, 50, 100, 250, 500 or 1000 times greater than the affinity for a non-target epitope. In certain embodiments binding affinity is determined by an affinity ELISA assay. In certain embodiments affinity is determined by a BIAcore assay. In certain embodiments binding affinity is determined by a kinetic method. In certain embodiments affinity is determined by an equilibrium/solution method.

The term "epitope" as used herein relates to a portion or portions of a capsid protein of ANV which is capable of being bound by a specific antibody. As would be understood in the art, epitopes generally consist of chemically active surface groups and have specific three dimensional structural characteristics, as well as specific charge characteristics. Epitopes may be defined from contiguous or non-contiguous sequences of amino acid residues comprised within a polypeptide sequence. The term "contiguous epitope" defines an epitope comprised of a linear series of amino acid residues within a polypeptide which define the epitope. A "non-contiguous epitope", which may also be referred to as a conformational and discontinuous epitope, is an epitope which is comprised of a series of amino acid residues which are non-linear in alignment, that is that the residues are spaced or grouped in a noncontinuous manner along the length of a polypeptide sequence. A noncontinuous epitope can be a discontinuous epitope wherein the amino acid residues are grouped into 2 linear sequences, or alternatively the noncontinuous epitope can be a discontinuous scattered epitope wherein the residues which contribute to the epitope are provided in three or more groups of linear amino acid sequences arranged along the length of the polypeptide.

As used in the description of the invention and the appended claims, the singular forms "a", "an" and "the" are intended to include the plural forms as well, unless context clearly indicates otherwise.

By "consisting essentially of" it is meant that that nucleic acid sequences of the invention described herein which include additional, substituted or deleted nucleotide(s), do not encode amino acid sequences which have significantly altered antigenic character to amino acid sequences encoded by the nucleic acid sequence of the of the invention, such that antibodies raised against the amino acid sequences encoded by nucleic acid sequences of the invention still have binding specificity to an amino acid sequence encoded by the nucleic acids sequences including additional, substituted or deleted nucleotide(s) or amino acid(s). Where the sequence is an amino acid sequence, "consisting essentially of" means the sequence does not include an additional substituted or deleted amino acid, which significantly alters the antigenic character of the amino acid sequence of the invention.

A variant of the invention can have at least 80%, at least 85%, preferably at least 90%, preferably at least 93%, more preferably at least 95%, more preferably at least 98%, even more preferably at least 99%, and most preferably 100% sequence identity to at least one of SEQ ID NO 4, SEQ ID NO 5 or SEQ ID NO 6. Suitably a variant of the invention may be an amino acid sequence encoded by any one nucleic acid comprising SEQ ID NO 1, SEQ ID NO 2 or SEQ ID NO 3 or an amino acid sequence comprising SEQ ID NO 4, SEQ ID NO 5 or SEQ ID NO 6 wherein the amino acid sequence has between 1 to 5, 1 to 10, 1 to 15, or 1 to 20 amino acid residues deleted, substituted, and/or added to the amino acid sequence and wherein said amino acid sequence is capable of stimulating an immune response (i.e. has antigenic activity), in an avian.

A fragment can be a portion of an amino acid sequence encoded by any one nucleotide sequence comprising SEQ ID NOs 1 to 3 or a variant thereof which is capable of generating an immune response directed there against similar to that provided by an amino acid sequence comprising SEQ ID NO 4, 5 or 6. In embodiments, the length of a fragment which generates an immune response can comprise at least 6, up to 15, preferably up to 25, and more preferably up to 50 contiguous amino acids. An antigenic fragment may be generated using for example C-terminal deletion of any one of the nucleic acid sequences of SEQ ID NO 1, SEQ ID NO 2 or SEQ ID NO 3 and said C-terminal deletion constructs may then be inserted into a suitable prokaryotic or eukaryotic expression plasmid. The antigenic activity of the expression products derived from the constructs may then be tested by assessing reactivity with antisera from naturally and/or experimentally infected chickens using immunoblotting methods.

In alternative embodiments a series of synthetic peptide fragments with greater than 85% greater than 90%, greater than 95%, or 100% sequence identity to portions of any one of SEQ ID NO 4, SEQ ID NO 5, or SEQ ID NO 6, or a fragment thereof can be generated. In further embodiments, a fragment can be generated by chemical or mechanical disruption of an amino acid comprising at least one of SEQ ID NOs 4, 5, 6, 23, 24, 25, 26, 27, 28, 29, 30 and 31. These peptides may then be reacted with antisera from naturally or experimentally infected chickens using an ELISA method to determine which peptide fragments are antigenic. Alternatively, synthetic peptides may be used to immunise, for example, mice, rabbits, or chickens and the antisera produced can be assessed for reactivity with ANV using indirect immunofluorescence assays. In this way immunogenic fragments may be identified and virus-specific antisera may be produced. These two latter approaches described are particularly advantageous for small peptides that contain linear, continuous epitopes.

The invention described herein will now be exemplified with reference to the following non-limiting examples and figures. Other embodiments of this invention will be apparent to those of ordinary skill in the art in view of this description.

FIG. 1 illustrates an alignment of 5 representative ANV types, ANV-1, ANV-2 and SEQ ID NOs 4, 5 and 6 to show variable regions.

Discussion

The present inventors have determined that ANV is vertically transmitted by using the described real-time RT-PCR test, and detecting ANV RNA in dead embryos which provides strong evidence that the virus was transmitted from an infected parent bird to the embryo within the egg.

There is also indirect evidence based on serological studies (Connor et al. 1987. Avian Pathology 16: 15-20)

This inventors' determinations have implications for the manufacture of poultry vaccines that are produced in chicken embryos, as SPF flocks used to produce embryonated eggs or chicks for vaccine production are required to be free from ANV infection. To demonstrate that ANV infection is not present in an avian, an antibody-detecting test to screen SPF flocks for ANV infection is required. Presently, the G4260 ANV-1 isolate provides a basis for serological screening of most flocks. However, in practice, this only exhibits low levels of antigenic cross-reactivity with other ANVs belonging to different serotypes. The present inventors have determined the capsid protein sequence diversity of around 20 ANVs and based on the diversity of capsid protein sequences observed, the inventors have determined three novel representative sequences. These additional novel sequences can be utilised with the two known amino acid sequences for the capsid protein of ANV-1 and the second serotype ANV-2, which are present in databases. Moreover, the inventors have determined key variable regions between ANV capsid protein sequences. Knowledge of these sequences allows the preparation of antibodies which show cross-reactivity and the ability to differentiate between different avian nephritis viruses.

TABLE 2

Pairwise amino acid and nucleotide identities (%) shared by the capsid protein genes of 5 representative ANVs

|  | ANV-1 | ANV-2 | VF04-1/2 | VF07-13/7 | VF08-3a |
|---|---|---|---|---|---|
| ANV-1 | — | 71 | 68 | 58 | 64 |
| ANV-2 | 69 | — | 73 | 56 | 61 |
| VF04-1/2 | 67 | 74 | — | 66 | 71 |
| VF07-13/7 | 62 | 62 | 68 | — | 78 |
| VF08-3a | 64 | 65 | 72 | 80 | — |

Amino acid comparisons in top right; nucleotide comparisons in bottom left

Determination of Representative Sequences

On examination of around 20 capsid protein genes it was recognised by the inventors that there were conserved or semi-conserved regions and highly variable regions of amino acid sequence. Using the amino acid numbering of the G4260 isolate of ANV-1, the 9 major variable regions, designated "A to I", were identified at amino acid residues: 15-37 (A), 113-127 (B), 221-239 (C), 338-352 (D), 399-418 (E), 438-454 (F), 474-483 (G), 523-544 (H) and 628-639 (I). This is illustrated in FIG. 1.

Because ANVs show antigenic variation, for example, ANV-1 and ANV-2 are serotypically different, at least some of these variable regions will correspond to regions of antigenic variation. ANVs were considered by the inventors to have different variable regions if, over the sequence considered, less than 75% of the amino acid residues were the same. The serotypically different ANV-1 and ANV-2 isolates were identified to be different in at least 9 major variable regions.

When the amino acid sequences for a capsid protein from 5 different representative ANVs, including the capsid protein amino acid sequences of ANV-1, ANV-2, were compared in terms of their variable regions, they were found to show substantial differences in these variable regions (Table 3). However, when some representative ANVs were compared to each other the sequences of some variable regions were very similar (75% or >75% amino acid identity). For example, representative ANVs 2 and 3 were similar in variable regions F, G, H and I, whereas representative ANVs 4 and 5 were similar in variable regions A, B, C and D.

TABLE 3

Variation in the "variable regions" displayed by 5 representative ANVs

| Repr. ANV[a] | A | B | C | D | E | F | G | H | I |
|---|---|---|---|---|---|---|---|---|---|
| ANV-1 | 1 | 1 | 1 | 1 | 1 | 1 | 1 | 1 | 1 |
| ANV-2 | 2 | 2 | 2 | 2 | 2 | 2 | 2/3[b] | 2/3 | 2/3 | 2/3 |
| VF04-1/2 | 3 | 3/4/5 | 3 | 3 | 3 | 3 | 2/3 | 2/3 | 2/3 | 2/3 |

TABLE 3-continued

Variation in the "variable regions" displayed by 5 representative ANVs

| Repr. ANV[a] | A | B | C | D | E | F | G | H | I |
|---|---|---|---|---|---|---|---|---|---|
| VF07-13/7 | 4 | 3/4/5 | 4/5 | 4/5 | 4/5 | 4 | 4 | 4 | 4 | 4 |
| VF08-3a | 5 | 3/4/5 | 4/5 | 4/5 | 4/5 | 5 | 5 | 5 | 5 | 5 |

[a]5 representative (Repr.) isolates were identified including ANV-1 and ANV-2
[b]variable region of representative (Repr.) ANV 2 is shared with representative ANV 3 etc.

When the capsid sequences of 14 additional ANVs were compared with the 5 representative ANVs in terms of their variable regions, in most cases their variable regions were shown to resemble those of particular representative ANVs (Table 4). In some cases, the sequences of the variable regions were less than 75% identical to those of the 5 representative ANVs. Of the 14 ANVs investigated, 9 were found to differ from the 5 representative ANVs in relation to their variable regions, when the 75% cut-off value for similarity was applied. For example 9 different sequences were observed for variable region E, and 7 different sequences were observed for variable region I.

Additional examination showed that different combinations of the variable regions displayed by different representative ANVs were observed in particular examples of the 20 ANVs investigated (Table 4). For example, the variable regions F, G and H of ELV276Cl3, VF05-1/5 and VF08-3b were similar to those of the representative isolate 1 (ANV-1), whereas the variable regions B, C and D of these ANVs were different. This suggests recombination can occur between different ANVs, bringing together different parts of the capsid protein gene. In this connection the variable regions A, B, C and D and sometimes E of the around 20 individual ANV examples were mainly the same as that of a particular representative ANV, for example all like 1, all like 2, and these could be found combined with F, G and H variable regions that were typical of a different representative ANV (Table 4).

Knowledge of the sequences of individual variable regions (i.e. that are different from those of the 5 representative ANVs) might be useful in the generation of antibodies for diagnosis as such antibodies may be able to differentiate isolates. Further, knowledge of the sequence of the variable region may allow the modification of an infectious clone or a capsid protein construct to include the different variable region.

Of the around 20 novel ANVs determined, 3 of these are considered to be representative. Of the remainder, 9 were considered to be distinguishable following comparison of the variable regions i.e. less than 75% identical over the variable region peptide sequences (Table 4).

TABLE 4

Variation in the "variable regions" displayed by capsid protein sequences of the 5 representative ANVs and 9 additional ANVs displaying variation within variable regions.

|  | A | B | C | D | E | F | G | H | I |
|---|---|---|---|---|---|---|---|---|---|
| ANV1 | 1 | 1 | 1 | 1 | 1 | 1 | 1 | 1 | 1 |
| ANV2 | 2 | 2 | 2 | 2 | 2 | 2/3 | 2/3 | 2/3 | 2/3 |
| VF04-1/2 | 3/4/5 | 3 | 3 | 3 | 3 | 2/3 | 2/3 | 2/3 | 2/3 |
| VF07-13/7 | 3/4/5 | 4/5 | 4/5 | 4/5 | 4 | 4 | 4 | 4 | 4 |
| VF08-3a | 3/4/5 | 4/5 | 4/5 | 4/5 | 5 | 5 | 5 | 5 | 5 |
| ELV276Cl5 | 2 | 2 | ELV276cl5 | 2 | 2 | 2/3 | 2/3 | 2/3 | 2/3 |
| ELV276Cl3 | 2 | 2 | ELV276cl5 | 2 | 2 | 1 | 1 | 1 | ELV276cl3 |
| Belgian ELV1 | Belgian ELV1 | 2 | ELV276cl5 | 2 | 2 | 1 | 1 | 1 | ELV276cl3 |
| VF05-1/5 | 3/4/5 | 3 | 3 | 3 | VF05-1/5 | 1 | 1 | 1 | VF05-1/5 |
| VF08-3b | 3/4/5 | 4/5 | 4/5 | 4/5 | VF08-3b | 1 | 1 | 1 | 1 |
| VF08-18/14 | 3/4/5 | 4/5 | 4/5 | 4/5 | 5 | 5 | 5 | 5 | 5 |
| VF08-18/5 | 3/4/5 | 4/5 | 4/5 | 3 | 3 | VF08-18/5 | 4 | 4 | 4 |
| VF08-29a | VF08-29a | 1 | 1 | 1 | VF08-29a | 1 | 1 | 1 | VF08-29a |
| VF08-29b | VF08-29a | 1 | 1 | 1 | VF08-29b | 2/3 | 2/3 | 2/3 | 2/3 |
| Total | 5 | 4 | 5 | 4 | 9 | 5 | 4 | 4 | 7 |

ANV-1, ANV-2, VF04-1/2, VF07-13/7 and VF08-3a were considered to be "representative" ANVs 1 to 5 respectively.

Based on the nucleic acid sequences of the novel ANV sequences and also ANV-1 and ANV-2, primers were determined which provide for an amplification of a fragment of 182 bp located in the 3'UTR of the ANV genome (Table 5).

TABLE 5

Primers used for RT-PCR test for detecting ANV

| Primer Name | Sequence 5' -> 3' | Nucleotide Position in ANV-1 (G4260) genome |
|---|---|---|
| ANV Forward | ACGGCGAGTACCATCGAG | 6715-6732 |
| ANV Reverse | AATGAAAAGCCCACTTTCGG | 6877-6896 |

Example of Conventional RT-PCR Test to Determine ANV within a Sample

A single tube RT-PCR format was used, involving reverse transcription at 45° C. for 30 min, followed by an initial denaturation step at 94° C. for 2 min, followed by 40 PCR cycles with each cycle comprising denaturation at 94° C. for 30 sec, annealing at 50° C. for 30 sec, and extension at 68°

C. for 30 sec. Reactions were carried out in 25 µl volumes comprising 12.5 µl reaction mix (×2) Superscript III one-step RT-PCR kit, 1.0 ul Forward primer, 1.0 ul Reverse primer, 7.0 ul DEPC water, 1.0 ul Enzyme and 2.5 µl RNA template. PCR products were analysed by agarose gel electrophoresis and visualised following ethidium bromide staining using UV transillumination.

Using serial 10-fold dilutions of in vitro transcribed RNA, that had been produced from a recombinant plasmid containing ANV cDNA, the limit of detection (LOD) of the conventional RT-PCR test was estimated to be 18 molecules. No RT-PCR amplicons were produced with RNAs that had been extracted from samples of DHV-2, DHV-3, and the 11672 and 612 isolates of CAstV, which were previously shown to be positive using the pan-avian astrovirus degenerate primer based RT-PCR test (Todd et al., 2009), thereby indicating that the RT-PCR test was specific for ANV and not for other avian astroviruses.

Application of Conventional RT-PCR Tests to Field Samples.

Gut content or faeces samples that had been collected from broiler chicken flocks experiencing enteritis and growth retardation problems were tested by the RT-PCR test. Fifty-five samples were received from October 2004 to May 2008 as part of 10 submissions obtained from 6 different UK poultry organisations. Additional samples were obtained from affected broiler flocks in Germany (n=15) and the USA (n=12). Of 82 samples tested 82 (100%) were positive by RT-PCR, the majority producing single DNA bands, sized 182 bp, after agarose gel electrophoresis, ethidium bromide staining and UV transillumination. In addition, positive RT-PCR results were obtained with 5 pooled swab samples that were collected from broiler chickens affected by wet litter problems and 5 pooled samples collected from chicken flocks that were unaffected by wet litter problems. Additional amplicon bands were observed with some samples especially those prepared from swabs that had been extracted with the RNeasy extraction kit.

Application of RT-PCR Tests to Longitudinal Surveys Samples.

Four flocks, which, based on recent performances, were predicted to exhibit average and below average performances were sampled longitudinally. The flocks belonged to the same UK poultry organisation, but were located on different sites. Gut contents from ~12 birds were sampled from each flock at days 0, 4 or 5, 7, 10, 14, 21 and 28. The samples were grouped into 4 pools and processed by homogenisation as described above. In total ~84 gut content samples were collected from each surveyed flock, from which 28 pooled samples were processed for RNA extraction. The performance of each flock was estimated after slaughter by calculating European production efficiency factor (EPEF) values, which represent standard measures of overall flock performance as determined by the equation:

$$EPEF = \frac{liveweight\ (kg) \times liveability\ (\%)}{age\ at\ depletion\ (days) \times feed\ conversion\ rate} \times 100$$

Of 96 pooled gut content samples, collected in longitudinal surveys of 4 broiler flocks from day 0 to day 28, 80 (83%) tested positive by the RT-PCR test. The 16 negative samples were those collected at day 0, when the chicks were introduced to the broiler house, but all pooled samples collected the later timepoints tested positive. Below average EPEF values of 327, 315 and 308 were estimated for the 3 male broiler flocks and an EPEF value of 238 was estimated for the female broiler flock that was surveyed.

Comparison of Conventional RT-PCR Tests.

The RNAs extracted from 12 representative field samples, which tested positive by our newly-developed RT-PCR test, were tested by 2 previously described RT-PCR tests. Using the test reported by Day et al. (2007), 10 samples were positive, while 9 of the 12 samples were positive by the RT-PCR test described by (Mandoki et al. (2006b)). Thus, the primers disclosed herein advantageously provide a more sensitive assay.

Real-Time RT-PCR

TABLE 6

Primers used in the TaqMan real-time RT-PCR test

| Primer/Probe | Sequence 5' -> 3' | Nucleotide Position in ANV-1 (G4260) genome |
|---|---|---|
| Q panANV Probe | 5'-FAM-CAGCAAATGACTTTC-MGB | 6692-6706 |
| QpanANV Forward | GTAAACCACTGGYTGGCTGACT | 6669-6690 |
| Qpan ANV Reverse | TACTCGCCGTGGCCTCG | 6708-6724 |

The real-time test used TaqMan® technology, involving the use of forward and reverse primers and the internal TaqMan® hydrolysis probe. The target sequence is a highly conserved region within the 3' UTR of the ANV genome, identified following comparison of approximately 20 ANVs including the published ANV-1 and ANV-2 sequences. Despite the high levels of conservation, the Forward primer was degenerate in one position. The RT-PCR product comprised 56 nucleotides. Following reverse transcription at 45° C. for 10 min and an initial denaturation stage at 95° C. for 10 min, amplifications were performed over 40 cycles of denaturation at 95° C. for 15 sec, and annealing/elongation at 60° C. for 45 sec (Primer: Probe ratio: 400 nM:400 nM:120 nM). Reactions were carried out in 25 µl volumes.

Sensitivity, Efficiency and Specificity of Real-Time Assay.

The detection limit and efficiency of the ANV real-time RT-PCR assay were determined using $C_T$ values obtained from a ten-fold dilution series of run-off RNAs, which had been in vitro transcribed from a cloned PCR product of 394 bp. An LOD of approximately 180 copies was estimated for the assay, based on the last reproducibly detectable dilution, which had a $C_T$ value of ~35. Standard curves of the $C_T$ values versus the RNA dilutions were constructed and used to estimate the number of viral copies in unknown samples. For convenience, the viral copy numbers were transformed into logarithm values, hereafter termed "log values". The PCR amplification efficiencies of the assay was estimated as 99.0% from the slope generated from the same dilution series using the equation, Efficiency=$10^{(-1/slope)}-1$. The $R^2$ value was 0.999. RNA extracted from a cell culture pool of ANV-1 was used at a $10^{-5}$ dilution as a positive control in all further RT-PCR assays. The ANV RT-PCR assay was negative when applied to the 5 isolates of chicken astrovirus and the duck hepatitis virus types 2 and 3. Using an internal positive control assay, no PCR inhibition was observed with any of 20 randomly selected gut content samples, indicating RNAs that were extracted from gut content samples using the QIAamp Viral RNA Mini Kit, were unlikely to be display PCR inhibition.

Detection of ANV RNA in Diagnostic Samples from Broiler Flocks

The assay was assessed using RNAs extracted from a panel of 36 field samples that originated in the UK and USA (Table 7).

TABLE 7

Summary of ANV real-time RT-PCR results obtained with field samples

| Sample | Age days | ANV Log Value |
|---|---|---|
| VF04-01/2 | U[a] | 5.79 |
| VF04-01/6 | U | 6.26 |
| VF0401/11 | U | 5.69 |
| VF05-01/3 | 6 | 8.23 |
| VF0501/14 | 10 | 5.88 |
| VF06-01/2 | 13 | 7.60 |
| VF06-01/3 | 11 | 7.53 |
| VF06-02/1 | 25 | 6.16 |
| VF06-02/3 | 39 | 3.22 |
| VF06-02/9 | 42 | Neg |
| VF06-07/1 | 10 | 7.50 |
| VF07-04/1 | U | 5.39 |
| VF07-04/2 | U | NT |
| VF07-13/1 | 14 | 7.64 |
| VF07-13/1[k] | 14 | 4.39 |
| VF07-13/7 | 14 | 7.63 |
| VF07-13/7[k] | 14 | 5.67 |
| VF07-13/9 | 17 | 7.02 |
| VF07-13/9[k] | 17 | 4.17 |
| VF08-05/8[s] | U | 6.57 |
| VF08-05/9[s] | U | 5.13 |
| VF08-05/21[s] | U | 4.38 |
| VF08-05/24[s] | U | 4.38 |
| VF08-07/2 | 10-17 | 6.02 |
| 799 MO/2005 | 7 | 7.55 |
| 802 AR/2005 | 7 | 7.59 |
| 812 DE/2005 | 10 | 7.84 |

TABLE 7-continued

Summary of ANV real-time RT-PCR results obtained with field samples

| Sample | Age days | ANV Log Value |
|---|---|---|
| 836 NC/2005 | 8 | 6.91 |
| 840 AR/2005 | 5 | 7.49 |
| 866 GA/2006 | 14 | 7.08 |
| 883 MO/2006 | 7 | 7.52 |
| 916 CA/2006 | 12 | 6.14 |
| 1254 GA/2008 | 7 | 8.80 |
| 1255 GA/2008 | 4 | 8.42 |
| 1335 GA/2009 | 9 | 7.92 |
| 1340 GA/2009 | 9 | 6.86 |

[a]Birds were of unknown (U) age
[k]All samples are from gut contents with exception of those marked with "k", which are from kidney These comprised samples prepared from intestinal contents (n=29), kidneys (n=3) and cloacal swabs (n=4). The majority (27 of 29) of the intestinal content samples came from broiler flocks with enteritis and/or growth depression problems. ANV RNA was detected in 34 of 35 samples tested, with a broad log value range (3.22-8.80) being observed. The majority of samples (23/34; 67.6%) were considered to have high (>5.99) log values, including 3 samples with log values greater than 7.99. Of the 26 gut content samples tested from growth-retarded broilers 21 (80.8%) had high log values. Although one of the 26 samples tested negative, none of the 4 remaining positive samples had low (<4.00) log values. The ANV RNA log values for the 3 kidney samples ranged from 4.17 to 5.67 and these were less than the values (range 7.02-7.63) obtained for gut content samples collected from the same birds.

Detection of ANV RNA in Longitudinal Survey Samples of Broiler Flocks

In the longitudinal surveys of 2 broiler flocks, A & B, gut content and kidney samples from ~12 birds, collected at timepoints from days 0 to 42, were tested for ANV using the real-time RT-PCR test. Results obtained with the day 0 samples showed that ANV RNA was detected in very few chickens and resulted in very low mean log values. ANV RNAs were detected in all 12 or in the majority of gut content and kidney samples collected at all timepoints after day 0 (Table 8).

TABLE 8

Summary of ANV real-time RT-PCR results obtained with gut content and kidney samples collected in longitudinal surveys of flocks A abnd B[1].

|  | Day 0 | Day 5 | Day 7 | Day 14 | Day 21 | Day 28 | Day 35 | S.E.M. | P value |
|---|---|---|---|---|---|---|---|---|---|
| A gut | 0.00 (1) | 4.67[ab] (12) | 7.27[c] (12) | 7.02[cd] (12) | 6.43[d] (12) | 5.21[a] (12) | 4.35[b] (12) | 0.244 | <0.001 |
| A kid | 0.00 (2) | 1.02 (4) | 3.62[a] (12) | 4.01[a] (12) | 4.00[a] (12) | 2.82 (10) | 1.94 (3) | 0.267 | <0.001 |
| B gut | 0.00 (1) | 8.09[a] (12) | 8.00[a] (12) | 6.84[b] (12) | 6.26[b] (12) | 5.08[c] (12) | 5.16[c] (12) | 0.211 | <0.001 |
| B kid | 0.00 (0) | 4.71[ab] (12) | 4.94[a] (12) | 4.31[ab] (12) | 3.89[b] (12) | 2.10[c] (8) | 1.41[c] (6) | 0.320 | <0.001 |

[1]Within a row, means with a common superscript are not significantly different.
The Day 0 values were not included in the statistical analysis and were therefore not included with in relation to the use of superscripts.
Figures in brackets denote the number of positive samples out of 12.

It was noted that the levels of ANV RNA in the gut contents and kidneys were considerably greater at early timepoints (days 7 and 14) than those at later timepoints (days 28 and 35). For example, in flock A, the ANV log values for the gut content samples at days 28 and 35 were 5.21 and 4.35 respectively whereas those at days 7 and 14 were 7.27 and 7.02 respectively, while in flock B the ANV log values for the kidney samples were 2.10 and 1.41 at days 28 and 35 respectively, whereas values of 4.94 and 4.31 were obtained for kidney samples at days 7 and 14 respectively.

The variation in ANV RNA levels present in gut content and kidney samples at early timepoints was further investigated by testing day 4/5 and day 7 samples from 2 additional broiler flocks (Table 9).

TABLE 9

Summary of ANV real-time RT-PCR results obtained with gut content and kidney samples collected at early timepoints from four broiler flocks different performance values.[1]

|  | Flock A | Flock B | Flock C | Flock D | S.E.M. | P value |
|---|---|---|---|---|---|---|
| Day 4/5 gut | 4.67[a] | 8.09[b] | 4.69[a] | 7.69[b] | 0.289 | <0.001 |
| Day 4/5 kid | 1.02 | 4.71[a] | 2.92 | 5.12[a] | 0.383 | <0.001 |
| Day 7 gut | 7.27 | 8.00[a] | 8.48 | 7.89[a] | 0.172/0.157[2] | <0.001 |
| Day 7 kid | 3.62[a] | 4.94[b] | 4.69[b] | 3.98[a] | 0.226/0.206[2] | <0.001 |
| EPEF | 327 (male) | 308 (male) | 315 (male) | 238 (female) | | |

[1]Within a row, means with a common superscript are not significantly different
[2]S.E.M. presented for min/max replication as the number of birds from each flock differs.

With flocks C and D, samples were collected at day 4 and not day 5 as was the case for flocks A and B. For the purposes of this study, the results obtained with the 4 flocks were compared at the day 4/5 timepoint and at the day 7 timepoint. Significant differences were observed when the flocks were compared with regards to the ANV RNA levels detected at both the day 4/5 and day 7 timepoints and with both the gut content and kidney samples. Thus, at day 4/5 the ANV RNA levels in samples from flocks A (gut content: 4.67, kidney: 1.02) and C (gut content: 4.69; kidney: 2.92) were significantly lower than the levels detected in flocks B (gut content: 8.09; kidney 4.71) and D (gut content: 7.69; kidney: 5.12). In addition, the flock A day 5 ANV RNA level detected in the kidney was significantly lower than that detected in the day 4 kidney sample from flock C. In contrast to the large differences observed between flocks at day 4/5, the ANV RNA levels detected in the day 7 gut content samples were much closer in value (log value range: 7.27-8.48) as were those detected in the day 7 kidney samples (log value range: 3.62-4.94), although some differences were considered to be significant (Table 4). For example the flock A day 7 ANV RNA levels in kidney was significantly less than those detected in corresponding samples from flocks C and D, and the flock A day 7 ANV RNA level in gut content was significantly less than that detected in the corresponding sample from flock C. The EPEF values obtained for the 3 male broiler flocks were 327 (flock A), 308 (flock B) and 315 (flock C), while an EPEF value of 238 was estimated for the flock D, the only female broiler investigated.

Application to Real-Time RT-PCR Test to Experimental Infection Samples.

One-day-old broiler chicks were infected orally with pooled gut content samples that were collected at days 4 and 7 from flock D. The ANV RT-PCR tests was applied to gut content and kidney samples that were collected from groups of 5 experimentally infected chickens at different days post infection. Results showed that ANV RNA was detected in 30/30 (100%) gut content and 25/30 (83.3%) kidney samples that were collected up to day 28 p.i. (Table 10).

TABLE 10

Summary of real-time ANV results obtained with gut content and kidney samples collected from experimentally infected broiler chickens (infected at day 0) at selected times post infection.[1]

| Virus | Sample | Day 3 Virus RNA log value (No +ve) | Day 7 Virus RNA log value (No +ve) | Day 10 Virus RNA log value (No +ve) | Day 14 Virus RNA log value (No +ve) |
|---|---|---|---|---|---|
| ANV | Gut | 8.07[a] (5) | 7.80[a] (5) | 7.68[ab] (5) | 6.85[b] (5) |
| ANV | Kidney | 5.36[a] (5) | 5.00[a] (5) | 4.60[a] (5) | 4.00[a] (5) |

| Virus | Day 21 Virus RNA log value (No +ve) | Day 28 Virus RNA log value (No +ve) | S.E.M. | P value |
|---|---|---|---|---|
| ANV | 4.84[c] (5) | 4.05[c] (5) | 0.321 | <0.001 |
| ANV | 1.09[b] (2) | 1.61[b] (3) | 0.500 | <0.001 |

[1]Within a row, means with a common superscript are not significantly different ANV RNA levels were high (log values: 6.85-8.07) in the gut content samples collected up to day 14 p.i., with substantially reduced virus levels detected at days 21 (log value: 4.84) and 28 (log value: 4.05). A similar trend was observed with the kidney samples, although the ANV RNA levels were markedly less (2-3 log values) at most timepoints p.i.

Although the invention has been particularly shown and described with reference to particular examples, it will be understood by those skilled in the art that various changes in the form and details may be made therein without departing from the scope of the present invention.

The invention claimed is:

1. A method for detecting avian nephritis viruses (ANVs) in a sample comprising the steps:

a. isolating total RNA from the sample, b. synthesising a first strand of DNA from said isolated RNA using a forward primer consisting of SEQ ID NO: 11, where Y is C or T, c. amplifying said first strand of DNA using a reverse primer comprising SEQ ID NO: 35 to form an amplified product and d. detecting the amplified product.

2. The method of claim 1 wherein the method further includes the use of a detectable probe comprising SEQ ID NO: 13 for use as an internal probe in a real-time RT-PCR test.

* * * * *

SEQUENCE LISTING

<160> NUMBER OF SEQ ID NOS: 40

<210> SEQ ID NO 1
<211> LENGTH: 2031
<212> TYPE: DNA
<213> ORGANISM: Avian Nephritis Virus

<400> SEQUENCE: 1
atgcctggcc ctgccggccc tgccaatggg ggcgctcgcc ccaaaactca aatggccaaa    60
cccaagaagg ctaaaaaacc tccatctcag aaaaagcctt ctcagcaaaa accactcaga   120

-continued

```
agggaaataa aaaaggtgga gaaacaggtg agagtgctca agaaacgcac taatgggccc    180
aagcagaatg atctcttcac aacaactgtt acgcttggga caatttctgg acagagtgac    240
aatggcctta ctaggcagat aaggctgcca cttaatccgc tacttctgaa atcatcagac    300
ggtggttcta caacaccact ctctatacgc ggttcaatgt atgagatgtg aaagttatt     360
agagcggaac tcatcgccac tcctctaaca ggtggtgcta atattgtggg ctccgtcggc    420
ttcatggtac tcacccttaa tgagcttgaa gcaactgcag actcaatcga ctccatcaaa    480
gccagaaagc atgtccagat accacttggt aggcttgcaa gactgaggct caccgcgcgt    540
gaatgcgcgg gtccgcgtga aggctggtgg cttactgata cttcccagtc accagctgac    600
tcgtatgggc cagcagtcga tcttatgatt gcctatgcaa ccacaaacct cctcaataca    660
tctgggggag ctagtgctac ctttcttggt actctctggc aagttgaaat cagagtcacc    720
tatgctttta gcacctacaa tccaaaacca ggtctgcaaa caatggtttc gcaaaccctg    780
gctggctcaa atcatcaagt cacaattcag cagtcgacaa ctgatggctc ccttataatg    840
acaacaaatg atgccaacct cctttctatc cttacccccc gtgttgcggg gcagaggtca    900
ggaaagtctc agacggtctg ggcgattgct ggggctgcgg ttgaggccgc tgctccactg    960
cttgggccgt ggggttggct tctaaaaggg ggttttggc ttgtgaggaa aatctttggt    1020
gcgtctgcac gtgacaccac ttcacagtac cagatctatc cctctattga agccgcaatg   1080
tctgaccaac ctatttttgg tcaaactggc acttccacaa ctgtcactct gcctattgtg   1140
cacatctcag aggtgatgaa tcctaaccct gagaataatg acctgactaa tccaaccgcc   1200
aggtctctcc caccagtacc accagcacct tcagaagacc ccatactccc gttggcggaa   1260
cttactgggc aagatggggt tccagcaaat tacacccttta atggtgactc ctatacgggt   1320
caagctgatt ggagggctc tacacttgtt cttactggaa taccaaaaca taagcgagta   1380
gctggtagtc tggccaattt tggtgtggta actaaccaaa tgtcaaaggt caccaccact   1440
gcccttgaga tctatgactt caccgatttt gggatcttct tcggtggagg ctatcaactt   1500
caggaaggtg gtgtacacac tggcaaaaca atggtacact cgcttatgac aggtgcccct   1560
ataaaaccct ggctttatgc aactcaatca tctacaacat ggtattggcc aacctggact   1620
ggctttccac agcccggaga aggcgactat ttcctacaga tgcaggacac cactgataga   1680
actacacata caacttgtgt tagtgtatat ctgcttgttg cctatcgagc gtcgcgtaga   1740
cttatagcct tctataacaa cggcggtcct gtgcgggcgg ctcctacaac catgctctgc   1800
ttatacaatg tagatgcagg ccgggcacca gcaacacctt acaacacctt ccaactcaca   1860
cttcaaagtg aaggtgctga cccaaattct ccatctgaag atgaagacga tgacatctca   1920
ttggcgggtt catgtcttca agatgagttt gattgtgtgg atcaactcga aaagaaaga   1980
gaagatctta tgaggaggtt aagagatcta gacctccggc gctttcagat c            2031
```

<210> SEQ ID NO 2
<211> LENGTH: 2031
<212> TYPE: DNA
<213> ORGANISM: Avian Nephritis Virus

<400> SEQUENCE: 2

```
atggctggcc ctgcgggctc gtccaatcgg ggcgctcgcc ctaaaactca aatggcaaaa    60
cctaagaagg ctaagaaacc tccatctcag aaaaagcctt ctcaaaaacc actcaggaag   120
gaagtaaaaa aggtggaaag acaggtcaag gtgcttaaga aacgcaccaa tggccctaag   180
```

```
caaaatgatg tgttcacaac aacagtcacc cttggaacca tctcgggcca aaatgacaat      240
ggtctaacca ggcaaattcg ggtgcctttc aaccccctac tttgtaagtc atctgatggt      300
ggctccacca caccactatc tataagggt tcaatgtatc aaatgtggaa ggtgcttaag       360
gcagagctac gtgcaacacc actaacaggg ggcaaatg tagtcggttc agtcggcttt       420
atggttctca ccctaaatgg tctcgaagcc actgcagatt ccatcgacac aataaaagca      480
agaaagcacg tgcagattcc gataggcaga agtgccgttc ttcgcattct tgcacgcgat      540
tgtgcgggtc ctcgcgaggg ttggtggctc actgatactt caagctcacc agctgacgct      600
tatgggcctg cggttgatct tatgattgcc tataaaacat caaacttgct taatgtgtca      660
agtaccaccg gtcctcaacc ctttaccggt actctgtggc aggcggagct caaagttact      720 tatgcttta gtacctacga cccgaaacct gggcttcaga cccttgtgtc ggagacactc       780
tctggtagtc atcaagtcac tattcaaacc tcagcagacg acggctcact tataatgaca      840
acaactgata cgcaactgct ttcactcctt acgccacgta cgggtgacca aagaagggg       900 aaatctccaa ctgtctgggc agtcgcaggc gccgttgttg atgctgtagc ccctgtacta     960
ggaccttggg gctggctact taagggtggc ttcttcctcg ttaggaagat ctttggggct     1020
tctactcgga atgcgggagc gtcttatcag atctacccct caattgagca ggctatgtct     1080
gatcaaccaa tttttggtca gcaatctgga acaacacaag tgacactccc gcttgttcat     1140
gtttccgagg ttatgaaccc caactccgag agtaacgacc taaatccaac tgctaggtca     1200
cttccaccta ttccacctgc tcaggagaaa attttaccac ttactctcct cgagggtcaa     1260
tcaggtgtcc ctgcactcta caccttaaac tctgggactg gagcttatac ccccatgacg     1320
cgttggacag gtggtactct acttctcact ggtgtaccag aatatgagct ccgtagtgga     1380
tcctcacaac aatttggggt tcgagtacaa aactcaccag gcctatcacc agctgcggca     1440
acatcaatac aaatttatga ttttacaaaa tttggcatct tctttggtgc tggtgagttc     1500
cttgggcaag ggggagtcca tacagcaaag actctcctga cagcaatcac tgcttctagc     1560
aaccctccct ggcttgattg ttccaggtac acatggagct ggcctgattg cttacctcg      1620 gctggctatc caaaacctgc ccagggtgat tggtggctgc agatgcaaaa agttggtgac      1680
actacatctc acacgacccc agttggcatc tatttcttaa tagcgtatga ggagatgcaa      1740
caacttgtgg cattctggca cacgggttct ggagcccaag ccgaacccac ttctcttctg      1800
tgcctataca atgttgatgc agggcgtgca cctgtgagag tcccacactt cattattaca      1860
actactgccc gcaatgaagt ggaggttgat ggggggtgatg actcagacga cgacatctct      1920
cttgctgggt cttgtgttgg cgacgagttt gagggtgtgg atcaactcga acgcgaaagg      1980
gcagaactca tgagcaggtt aagagaccta gacctgcggc gctttcagat c               2031
```

<210> SEQ ID NO 3
<211> LENGTH: 2019
<212> TYPE: DNA
<213> ORGANISM: Avian Nephritis Virus

<400> SEQUENCE: 3

```
atgcctggcc ctgccggccc tgccaatggg ggcgctcgcc ccaaaactca aatggcaaaa       60
cctaagaagg ctaagaaacc tccatctcag aaaaagcctc ctcaaaaacc acccaggaag      120
gaagtgaaga aggtggaaag acaggtaaag gtgcttaaga acgcaccaa tggccctaag      180 cagaatgatg tgttcacaac aacagtcact cttggaacca tctcgggcca aaatgacaat      240
ggtctaacca ggcaaatccg ggtgcctttc aacccccttac tatgtaagtc atctgacggt      300
```

```
ggttctacca caccactgtc aataagdggt tcaatgtatc aaatgtggaa ggtgcttaag    360
gcagagctac gtgcaacacc tctaacaggg ggggcaaata tagttggctc agtcggcttt    420
atggttctca ccctgaacgg gctcgaagcc actgcagact ccatcgacac aataaaagca    480
agaaagcacg tgcagattcc aattggcaga agtgccgttc ttcgcatact tgcgcgtgat    540
tgtgctgggc ctcgcgaagg ctggtggcta actgatacgt caagctcacc ggctgacgca    600
tatgdacccg cagtcgacct tatggttgcc tacagaacat caaacttgct taatgtgtcg    660
agtgccagta cccaacctca atcctttact ggtactctgt ggcaggcaga gctcaaagtt    720
acatatgctt ttagcaccta tgacccgaaa cctggtcttc aaactctcgt gtcagagacg    780
ctatctggta gccatcaagt tactattcaa acttcagcag acgacggctc acttataatg    840
acaacaaccg atacgcaact gctgtcactc cttacgccac gtacgggtga ccagaagaag    900
ggaaagtccc caactgtctg ggcagtcgca ggcgccgttg ttgacgctgt agcccctgtt    960
ctaggaccct ggggctggct acttaagggt ggcttcttcc tcgttaggaa gatctttggg   1020
gtttctgccc ggaatgcggg agcgtcctat cagatctacc cctctattga gcaggctatg   1080
tctgatcaac caatctttgg tcagcaatct ggaacaacac aagtgacact cccgcttgtc   1140
catgtctccg aggttatgaa ccccaactcc gagagtaacg acctaactcc aacttcaagg   1200
gctcttccac ctgcacctga gtcagagcct gagcttccac tggctcttct agttggccag   1260
gctggtgtcc ctgcagtgta tgagtatact ggggatgcct atacaccaca accaagatgg   1320
actggctcaa ctatcttcct tactggtgtt ccctatcata ctagggctac aggtgctaca   1380
cagtcttttg gagtgagaac taacaatatg tcaccttcaa actgcaccac acttgatatc   1440
tatgacttca cagattttgg ggtctttttt ggtagtaatg gctacctttc acaaggtgcc   1500
atacatactt caaaaacaat gatctactca ctcaagacaa atccaaatat caacccttgg   1560
cttgctgcaa accagtcttc caccacgtgg tccatgccaa cgtggtctgg ctatcccgca   1620
ccaggccaag gagattactt cctgcaaatg caagatacca ccgatacaac cacccatacg   1680
acttctgtgg gttgttattt tctggtgatg tatggtgaat cccggaaact tgttgcattt   1740
tttaatactg gcactggcac agcaagacct gcactttcat ctatgatgtg cctctataat   1800
gttgatgcag aagagcacc agtaaggata cagggctttc ttctcagccc ttcacaaaac   1860
tttgttgaaa ctgataatca ggacaatgac gacgatgatg acatctctct cgccgggtcc   1920
tgtctgcaag atgagtttga ttgtgtggat caactcgaaa agaaagaga agatcttatg   1980
aggaggctta gagatctaga cctccggcgc tttcagatc                          2019
```

<210> SEQ ID NO 4
<211> LENGTH: 677
<212> TYPE: PRT
<213> ORGANISM: Avian Nephritis Virus

<400> SEQUENCE: 4

Met Pro Gly Pro Ala Gly Pro Ala Asn Gly Gly Ala Arg Pro Lys Thr
1               5                   10                  15

Gln Met Ala Lys Pro Lys Lys Ala Lys Lys Pro Pro Ser Gln Lys Lys
            20                  25                  30

Pro Ser Gln Gln Lys Pro Leu Arg Arg Glu Ile Lys Lys Val Glu Lys
        35                  40                  45

Gln Val Arg Val Leu Lys Lys Arg Thr Asn Gly Pro Lys Gln Asn Asp
    50                  55                  60

```
Leu Phe Thr Thr Thr Val Thr Leu Gly Thr Ile Ser Gly Gln Ser Asp
 65                  70                  75                  80

Asn Gly Leu Thr Arg Gln Ile Arg Leu Pro Leu Asn Pro Leu Leu Leu
                 85                  90                  95

Lys Ser Ser Asp Gly Gly Ser Thr Thr Pro Leu Ser Ile Arg Gly Ser
            100                 105                 110

Met Tyr Glu Met Trp Lys Val Ile Arg Ala Glu Leu Ile Ala Thr Pro
        115                 120                 125

Leu Thr Gly Gly Ala Asn Ile Val Gly Ser Val Gly Phe Met Val Leu
    130                 135                 140

Thr Leu Asn Glu Leu Glu Ala Thr Ala Asp Ser Ile Asp Ser Ile Lys
145                 150                 155                 160

Ala Arg Lys His Val Gln Ile Pro Leu Gly Arg Leu Ala Arg Leu Arg
                165                 170                 175

Leu Thr Ala Arg Glu Cys Ala Gly Pro Arg Glu Gly Trp Trp Leu Thr
                180                 185                 190

Asp Thr Ser Gln Ser Pro Ala Asp Ser Tyr Gly Pro Ala Val Asp Leu
            195                 200                 205

Met Ile Ala Tyr Ala Thr Thr Asn Leu Leu Asn Thr Ser Gly Gly Ala
        210                 215                 220

Ser Ala Thr Phe Leu Gly Thr Leu Trp Gln Val Glu Ile Arg Val Thr
225                 230                 235                 240

Tyr Ala Phe Ser Thr Tyr Asn Pro Lys Pro Gly Leu Gln Thr Met Val
                245                 250                 255

Ser Gln Thr Leu Ala Gly Ser Asn His Gln Val Thr Ile Gln Gln Ser
            260                 265                 270

Thr Thr Asp Gly Ser Leu Ile Met Thr Thr Asn Asp Ala Asn Leu Leu
        275                 280                 285

Ser Ile Leu Thr Pro Arg Val Ala Gly Gln Arg Ser Gly Lys Ser Gln
        290                 295                 300

Thr Val Trp Ala Ile Ala Gly Ala Ala Val Glu Ala Ala Ala Pro Leu
305                 310                 315                 320

Leu Gly Pro Trp Gly Trp Leu Leu Lys Gly Gly Phe Trp Leu Val Arg
                325                 330                 335

Lys Ile Phe Gly Ala Ser Ala Arg Asp Thr Thr Ser Gln Tyr Gln Ile
            340                 345                 350

Tyr Pro Ser Ile Glu Ala Ala Met Ser Asp Gln Pro Ile Phe Gly Gln
        355                 360                 365

Thr Gly Thr Ser Thr Thr Val Thr Leu Pro Ile Val His Ile Ser Glu
    370                 375                 380

Val Met Asn Pro Asn Pro Glu Asn Asn Asp Leu Thr Asn Pro Thr Ala
385                 390                 395                 400

Arg Ser Leu Pro Pro Val Pro Pro Ala Pro Ser Glu Asp Pro Ile Leu
                405                 410                 415

Pro Leu Ala Glu Leu Thr Gly Gln Asp Gly Val Pro Ala Asn Tyr Thr
            420                 425                 430

Phe Asn Gly Asp Ser Tyr Thr Gly Gln Ala Asp Trp Arg Gly Ser Thr
        435                 440                 445

Leu Val Leu Thr Gly Ile Pro Lys His Lys Arg Val Ala Gly Ser Leu
    450                 455                 460

Ala Asn Phe Gly Val Val Thr Asn Gln Met Ser Lys Val Thr Thr Thr
465                 470                 475                 480

Ala Leu Glu Ile Tyr Asp Phe Thr Asp Phe Gly Ile Phe Phe Gly Gly
```

```
                    485                 490                 495
Gly Tyr Gln Leu Gln Glu Gly Val His Thr Gly Lys Thr Met Val
                500                 505                 510

His Ser Leu Met Thr Gly Ala Pro Ile Lys Pro Trp Leu Tyr Ala Thr
            515                 520                 525

Gln Ser Ser Thr Thr Trp Tyr Trp Pro Thr Trp Thr Gly Phe Pro Gln
        530                 535                 540

Pro Gly Glu Gly Asp Tyr Phe Leu Gln Met Gln Asp Thr Thr Asp Arg
545                 550                 555                 560

Thr Thr His Thr Thr Cys Val Ser Val Tyr Leu Leu Val Ala Tyr Arg
                565                 570                 575

Ala Ser Arg Arg Leu Ile Ala Phe Tyr Asn Asn Gly Gly Pro Val Arg
            580                 585                 590

Ala Ala Pro Thr Thr Met Leu Cys Leu Tyr Asn Val Asp Ala Gly Arg
        595                 600                 605

Ala Pro Ala Thr Pro Tyr Asn Thr Phe Gln Leu Thr Leu Gln Ser Glu
    610                 615                 620

Gly Ala Asp Pro Asn Ser Pro Ser Glu Asp Glu Asp Asp Ile Ser
625                 630                 635                 640

Leu Ala Gly Ser Cys Leu Gln Asp Glu Phe Asp Cys Val Asp Gln Leu
                645                 650                 655

Glu Lys Glu Arg Glu Asp Leu Met Arg Arg Leu Arg Asp Leu Asp Leu
            660                 665                 670

Arg Arg Phe Gln Ile
        675

<210> SEQ ID NO 5
<211> LENGTH: 677
<212> TYPE: PRT
<213> ORGANISM: Avian Nephritis Virus

<400> SEQUENCE: 5

Met Ala Gly Pro Ala Gly Ser Ser Asn Arg Gly Ala Arg Pro Lys Thr
1               5                   10                  15

Gln Met Ala Lys Pro Lys Ala Lys Pro Pro Ser Gln Lys Lys
            20                  25                  30

Pro Ser Gln Lys Pro Leu Arg Lys Glu Val Lys Val Glu Arg Gln
        35                  40                  45

Val Lys Val Leu Lys Lys Arg Thr Asn Gly Pro Lys Gln Asn Asp Val
    50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
                85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
        115                 120                 125

Thr Gly Gly Ala Asn Val Val Gly Ser Val Gly Phe Met Val Leu Thr
    130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
                165                 170                 175
```

```
Leu Ala Arg Asp Cys Ala Gly Pro Arg Glu Gly Trp Trp Leu Thr Asp
            180                 185                 190

Thr Ser Ser Pro Ala Asp Ala Tyr Gly Pro Ala Val Asp Leu Met
        195                 200                 205

Ile Ala Tyr Lys Thr Ser Asn Leu Leu Asn Val Ser Ser Thr Thr Gly
210                 215                 220

Pro Gln Pro Phe Thr Gly Thr Leu Trp Gln Ala Glu Leu Lys Val Thr
225                 230                 235                 240

Tyr Ala Phe Ser Thr Tyr Asp Pro Lys Pro Gly Leu Gln Thr Leu Val
                245                 250                 255

Ser Glu Thr Leu Ser Gly Ser His Gln Val Thr Ile Gln Thr Ser Ala
        260                 265                 270

Asp Asp Gly Ser Leu Ile Met Thr Thr Thr Asp Thr Gln Leu Leu Ser
        275                 280                 285

Leu Leu Thr Pro Arg Thr Gly Asp Gln Lys Lys Gly Lys Ser Pro Thr
        290                 295                 300

Val Trp Ala Val Ala Gly Ala Val Val Asp Ala Val Ala Pro Val Leu
305                 310                 315                 320

Gly Pro Trp Gly Trp Leu Leu Lys Gly Gly Phe Phe Leu Val Arg Lys
                325                 330                 335

Ile Phe Gly Ala Ser Thr Arg Asn Ala Gly Ala Ser Tyr Gln Ile Tyr
                340                 345                 350

Pro Ser Ile Glu Gln Ala Met Ser Asp Gln Pro Ile Phe Gly Gln Gln
        355                 360                 365

Ser Gly Thr Thr Gln Val Thr Leu Pro Leu Val His Val Ser Glu Val
        370                 375                 380

Met Asn Pro Asn Ser Glu Ser Asn Asp Leu Asn Pro Thr Ala Arg Ser
385                 390                 395                 400

Leu Pro Pro Ile Pro Pro Ala Gln Glu Lys Ile Leu Pro Leu Thr Leu
                405                 410                 415

Leu Glu Gly Gln Ser Gly Val Pro Ala Leu Tyr Thr Phe Asn Ser Gly
                420                 425                 430

Thr Gly Ala Tyr Thr Pro Met Thr Arg Trp Thr Gly Gly Thr Leu Leu
        435                 440                 445

Leu Thr Gly Val Pro Glu Tyr Glu Leu Arg Ser Gly Ser Ser Gln Gln
450                 455                 460

Phe Gly Val Arg Val Gln Asn Ser Pro Gly Leu Ser Pro Ala Ala Ala
465                 470                 475                 480

Thr Ser Ile Gln Ile Tyr Asp Phe Thr Lys Phe Gly Ile Phe Phe Gly
                485                 490                 495

Ala Gly Glu Phe Leu Gly Gln Gly Gly Val His Thr Ala Lys Thr Leu
                500                 505                 510

Leu Thr Ala Ile Thr Ala Ser Ser Asn Pro Pro Trp Leu Asp Cys Ser
        515                 520                 525

Arg Tyr Thr Trp Ser Trp Pro Asp Trp Leu Thr Ser Ala Gly Tyr Pro
        530                 535                 540

Lys Pro Ala Gln Gly Asp Trp Trp Leu Gln Met Gln Lys Val Gly Asp
545                 550                 555                 560

Thr Thr Ser His Thr Thr Pro Val Gly Ile Tyr Phe Leu Ile Ala Tyr
                565                 570                 575

Glu Glu Met Gln Gln Leu Val Ala Phe Trp His Thr Gly Ser Gly Ala
                580                 585                 590

Gln Ala Glu Pro Thr Ser Leu Leu Cys Leu Tyr Asn Val Asp Ala Gly
```

```
                595                 600                 605
Arg Ala Pro Val Arg Val Pro His Phe Ile Ile Thr Thr Thr Ala Arg
        610                 615                 620

Asn Glu Val Glu Val Asp Gly Gly Asp Asp Ser Asp Asp Ile Ser
625                 630                 635                 640

Leu Ala Gly Ser Cys Val Gly Asp Glu Phe Glu Gly Val Asp Gln Leu
                645                 650                 655

Glu Arg Glu Arg Ala Glu Leu Met Ser Arg Leu Arg Asp Leu Asp Leu
        660                 665                 670

Arg Arg Phe Gln Ile
        675

<210> SEQ ID NO 6
<211> LENGTH: 673
<212> TYPE: PRT
<213> ORGANISM: Avian Nephritis Virus

<400> SEQUENCE: 6

Met Pro Gly Pro Ala Gly Pro Ala Asn Gly Gly Ala Arg Pro Lys Thr
1               5                   10                  15

Gln Met Ala Lys Pro Lys Lys Ala Lys Lys Pro Pro Ser Gln Lys Lys
            20                  25                  30

Pro Pro Gln Lys Pro Pro Arg Lys Glu Val Lys Lys Val Glu Arg Gln
        35                  40                  45

Val Lys Val Leu Lys Lys Arg Thr Asn Gly Pro Lys Gln Asn Asp Val
    50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
                85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
        115                 120                 125

Thr Gly Gly Ala Asn Ile Val Gly Ser Val Gly Phe Met Val Leu Thr
    130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
                165                 170                 175

Leu Ala Arg Asp Cys Ala Gly Pro Arg Glu Gly Trp Trp Leu Thr Asp
            180                 185                 190

Thr Ser Ser Pro Ala Asp Ala Tyr Gly Pro Ala Val Asp Leu Met
        195                 200                 205

Val Ala Tyr Arg Thr Ser Asn Leu Leu Asn Val Ser Ser Ala Ser Thr
    210                 215                 220

Gln Pro Gln Ser Phe Thr Gly Thr Leu Trp Gln Ala Glu Leu Lys Val
225                 230                 235                 240

Thr Tyr Ala Phe Ser Thr Tyr Asp Pro Lys Pro Gly Leu Gln Thr Leu
                245                 250                 255

Val Ser Glu Thr Leu Ser Gly Ser His Gln Val Thr Ile Gln Thr Ser
            260                 265                 270

Ala Asp Asp Gly Ser Leu Ile Met Thr Thr Thr Asp Thr Gln Leu Leu
        275                 280                 285
```

```
Ser Leu Leu Thr Pro Arg Thr Gly Asp Gln Lys Lys Gly Lys Ser Pro
    290             295                 300

Thr Val Trp Ala Val Ala Gly Ala Val Val Asp Ala Val Ala Pro Val
305             310              315                 320

Leu Gly Pro Trp Gly Trp Leu Leu Lys Gly Gly Phe Phe Leu Val Arg
                325             330                 335

Lys Ile Phe Gly Val Ser Ala Arg Asn Ala Gly Ala Ser Tyr Gln Ile
                340             345             350

Tyr Pro Ser Ile Glu Gln Ala Met Ser Asp Gln Pro Ile Phe Gly Gln
        355             360             365

Gln Ser Gly Thr Thr Gln Val Thr Leu Pro Leu Val His Val Ser Glu
    370             375             380

Val Met Asn Pro Asn Ser Glu Ser Asn Asp Leu Thr Pro Thr Ser Arg
385             390             395                 400

Ala Leu Pro Pro Ala Pro Glu Ser Glu Pro Glu Leu Pro Leu Ala Leu
                405             410             415

Leu Val Gly Gln Ala Gly Val Pro Ala Val Tyr Glu Tyr Thr Gly Asp
            420             425             430

Ala Tyr Thr Pro Gln Pro Arg Trp Thr Gly Ser Thr Ile Phe Leu Thr
        435             440             445

Gly Val Pro Tyr His Thr Arg Ala Thr Gly Ala Thr Gln Ser Phe Gly
    450             455             460

Val Arg Thr Asn Asn Met Ser Pro Ser Asn Cys Thr Thr Leu Asp Ile
465             470             475                 480

Tyr Asp Phe Thr Asp Phe Gly Val Phe Phe Gly Ser Asn Gly Tyr Leu
                485             490             495

Ser Gln Gly Ala Ile His Thr Ser Lys Thr Met Ile Tyr Ser Leu Lys
            500             505             510

Thr Asn Pro Asn Ile Asn Pro Trp Leu Ala Ala Asn Gln Ser Ser Thr
        515             520             525

Thr Trp Ser Met Pro Thr Trp Ser Gly Tyr Pro Ala Pro Gly Gln Gly
    530             535             540

Asp Tyr Phe Leu Gln Met Gln Asp Thr Thr Asp Thr Thr Thr His Thr
545             550             555                 560

Thr Ser Val Gly Cys Tyr Phe Leu Val Met Tyr Gly Glu Ser Arg Lys
                565             570             575

Leu Val Ala Phe Phe Asn Thr Gly Thr Gly Thr Ala Arg Pro Ala Leu
            580             585             590

Ser Ser Met Met Cys Leu Tyr Asn Val Asp Ala Gly Arg Ala Pro Val
        595             600             605

Arg Ile Gln Gly Phe Leu Leu Ser Pro Ser Gln Asn Phe Val Glu Thr
    610             615             620

Asp Asn Gln Asp Asn Asp Asp Asp Asp Ile Ser Leu Ala Gly Ser
625             630             635                 640

Cys Leu Gln Asp Glu Phe Asp Cys Val Asp Gln Leu Glu Lys Glu Arg
                645             650             655

Glu Asp Leu Met Arg Arg Leu Arg Asp Leu Asp Leu Arg Arg Phe Gln
            660             665             670

Ile

<210> SEQ ID NO 7
<211> LENGTH: 182
<212> TYPE: DNA
<213> ORGANISM: Avian Nephritis Virus
```

```
<400> SEQUENCE: 7
acggcgagta gcatcgaggg tacaggaaag ctgggaccat tgcatagtca actaatttgg    60
ctgtgctagg gggaccaatg gggtggtagg tcaatcaaac cgccactcac gcaacttgga   120
gcctgctaaa acctacgctc ctgtgcgcta aagttggttc tcccgaaagt gggcttttca   180
tt                                                                 182

<210> SEQ ID NO 8
<211> LENGTH: 18
<212> TYPE: DNA
<213> ORGANISM: Artificial
<220> FEATURE:
<223> OTHER INFORMATION: synthesised nucliec acid sequence

<400> SEQUENCE: 8
acggcgagta gcatcgag                                                 18

<210> SEQ ID NO 9
<211> LENGTH: 20
<212> TYPE: DNA
<213> ORGANISM: Artificial
<220> FEATURE:
<223> OTHER INFORMATION: synthesised nucleic acid sequence

<400> SEQUENCE: 9
ccgaaagtgg gcttttcatt                                               20

<210> SEQ ID NO 10
<211> LENGTH: 56
<212> TYPE: DNA
<213> ORGANISM: Avian Nephritis Virus

<400> SEQUENCE: 10
gtaaaccact ggttggctga ctacagcaac tgactttccc gaggccacgg cgagta        56

<210> SEQ ID NO 11
<211> LENGTH: 22
<212> TYPE: DNA
<213> ORGANISM: Artificial
<220> FEATURE:
<223> OTHER INFORMATION: synthesised nucleic acid sequence
<220> FEATURE:
<221> NAME/KEY: Y
<222> LOCATION: (13)..(13)
<223> OTHER INFORMATION: y is c or t

<400> SEQUENCE: 11
gtaaaccact ggytggctga ct                                            22

<210> SEQ ID NO 12
<211> LENGTH: 17
<212> TYPE: DNA
<213> ORGANISM: Artificial
<220> FEATURE:
<223> OTHER INFORMATION: synthesised nucleic acid sequence

<400> SEQUENCE: 12
cgaggccacg gcgagta                                                  17

<210> SEQ ID NO 13
<211> LENGTH: 15
<212> TYPE: DNA
<213> ORGANISM: Artificial
<220> FEATURE:
```

<223> OTHER INFORMATION: synthesised nucleic acid sequence

<400> SEQUENCE: 13
cagcaactga ctttc                                                          15

<210> SEQ ID NO 14
<211> LENGTH: 2037
<212> TYPE: DNA
<213> ORGANISM: Avian Nephritis Virus

<400> SEQUENCE: 14
atggctggcg gtgccaccgc acctgcgggc gctaagccca agcagtccaa acaaaagcag 60
aaaaattctt ctcagcggaa atctaaaacc actcagaagg tgaaacaaca aaaacctcca 120
gtgaaaactg ttaggaggct tgagcaccaa gtcaacgcac tcaagaagaa gacaaatgga 180
cccaaaatga atgacatgat gaaaactact gtcacaattg gggtcatcca aggtcagact 240
caatcaggtc tcagtcgcca acttagggtg ccactaaacc ccctcttaat gaaatctaca 300
gaggggctag ctgctacccc gctatccatt aggtcatctt gctatgagct ctggaaagca 360
ctacatgttg agctttttgc aacaccacta actggtttct ccaatgtggt gggctcggta 420
ggctttatgg ctctaacact caatgggctt gaggcgaccg cagactccat cgactcaatc 480
aaggcgagga aacactacca aatggccctt ggtaggccag cgcggcttaa actcactgcc 540
cgtgaacttg cggggccgcg cgagggctgg tggctcactg atacatctga atcgcctgca 600
gatgcgtatg gacctgctat agacctgatg attgcttata aaactgagaa ccttcttaat 660
acaacaggtt cgacgacctc cacccacact ggaccactgt ggcagataga agcgcgggcg 720
acttatgggt ttgccaacta caacccaaaa ccaggacttc aaacgctcgt ctctcaaaca 780
ctgaccaacg ggcaaacggt gacaatccaa ccgtcaccaa atgatgggtc tctcataatg 840
acaacaacca gcctacaggt ccgatcgctg ctttcccctc gggctggtga cccaaagaag 900
gggaagtctc agacaatctg ggccatagca ggttctgcag ttgatgctgc ggcaaccgtc 960
cttggtccct ggggctggct actaaagggt ggtttctggc tagttagaca aatctttggt 1020
ggatcgtcta atgctgcagg cagcagctac cagatttatt cctcccttga gtctgcaatg 1080
gctgatcaac ccatctttgg cgcccaaact ggtacccagt ctattactgt acctgtagtg 1140
cacatctctg aagtcctgaa tccaaaccca atgtccaacc aagtacccac gcccagtgct 1200
ggctcggcac ctgcgccacc aacaccccca acccccattc aagacatcat acttccgctc 1260
gcggaactga cggggcaaga tggggttcca gcaaattaca cctttaatgg tgactcttat 1320
acgggtcaag gcgattggag gggttctaca cttgttctca ctggaatacc aagacataag 1380
cgagtaaccg gaaatctgtc taattttggt gtgacagtta atcaaatgtc aaaagtcacc 1440
acaactgcac ttgagatcta tgacttcacc gattttggtg tctccttcgg tggaggctac 1500
caacttcagg aaggtggtgt acatactggc aaaacaatgg ttcactcgct tatgacaggt 1560
gccccaataa aaccctggct ttatgcaact caatcatcta caacatggta ctggcccacc 1620
tggactggct ttccacagcc tggtcctggc gactattttc tacagatgca ggacaccact 1680
gacagaacaa cacacacaac ctgtgttagt gtctatctgc ttgtcgccta ccaagcgtcg 1740
cgcaggctta tagcgttcta caacaacggt ggtactgcgc gggcggcgcc tacaaccatg 1800
ctttgtctat acaatgtaga tgcaggccgg gcaccacaaa caccttataa caccttccaa 1860
ctcacacttc aaagtgaagt tgctgaccca aattctccat ctgaagatga agatgatgac 1920
atctcgcttg cgggttcttg tcttcaagat gagtttgatt gtgtggatca actcgaaaaa 1980

```
gaaagagaag accttatgag gaggttaaga gacctagacc tccggcgctt tcagatc     2037
```

<210> SEQ ID NO 15
<211> LENGTH: 2037
<212> TYPE: DNA
<213> ORGANISM: Avian Nephritis Virus

<400> S

<210> SEQ ID NO 16
<211> LENGTH: 2034
<212> TYPE: DNA
<213> ORGANISM: Avian Nephritis Virus

<400> SEQUENCE: 16

```
atggctggcg gtgccaccgc acctgcgggc gctaagccca acaacccaa acaaaagcag      60
aaaacttcct gtcagaggaa atccaaacct actcagaagg ttaaacaaca aaaacctcct    120
gtgaaaactg ttaggaggct tgagcgccaa gtcaacgcac tcaagaagaa gacaaatggg    180
cccaaaatga atgacataat gaaaactact gtcacacttg gggtcatcca aggccagact    240
caatcaggtc taagtcgcca acttagggtg ccactaaacc ccctcttgat gaaatctaca    300
gaggggctag ctgcgacccc gctgtccatt aggtcatctt gttatgagct atggaaagcc    360
ctacatgtcg agcttttgc aacaccactg actggctttt ccaatgtggt gggctcggta    420
ggctttatgg ctcttacact caatggactt gaggcgaccg cagattccat cgattcaatt    480
aaggcgagga aacattatca aatggccctc ggtaggccag cgcggcttaa acttactgcc    540
cgtgaactcg cggggccgcg tgagggctgg tggcttactg acacatctga atcgcctgca    600
gatgcctatg gacctgccat cgacctgatg attgcctaca aaactgagaa ccttctcaat    660
acatcaggtt ctacgacctc cacttacact ggaccctgt ggcagataga agcgcgggtg    720
acttatgggt tcgccactta caacccaaag ccaggacttc aaacgctcgt gtctcaatca    780
ttgaccaacg ggcaaacggt gacaatccaa ccgtcaccaa ctgatgggtc tcttataatg    840
acaacaaaca gcctacagat tcaatcactg ctctcccctc ggggttgatgg cccacagaag    900
gggaagtccc agacaatctg ggccatagca ggttctgcag ttgatgctgc ggcaaccgtt    960
cttggtccct ggggctggct acttaaaggt ggtttctggc tagttagact gatctttggt   1020
ggatcgtcta atgctgcagg cagcagctac cagttatact cctcccttga gtctgcaatg   1080
gctgatcaac ccatctatgg tgctcaaact ggtactcagt ccatcactgt acctgtggtg   1140
cacatctctg aagtcctgaa tccaaatcca atgttcaacc aggtatctgt gcctaccact   1200
ggttcggcac ctgcgccacc aacaccacca gcaccatctg aagacccat actcccgctg   1260
gcagaattaa ctggccaacc tggggtccca cctctctaca cctttgatgg cagtacctac   1320
actccaccga ctaactggct gggctccact ctattactaa ctggtatacc agctcacaaa   1380
cgagtcactg gtaattcggc taattttgga gttaccaacc ttcaaatgtc aaaagtaact   1440
gccactgcaa ttgaggtcta tgacttcaca gactttggtg ttttcttcgg cactggcact   1500
tatcttggtg aaggtggcat tcacactggg aagaccttag tgtactccct gatgtctggt   1560
caaacccca accctggct tgcagcaaac cagtcaggga cgacctggta cctcccttcg   1620
tgggttggtt ttcctacacc aggtgcgggt gactacttcc ttcaaatgca ggatgtaaca   1680
gacacgacaa ctcacacaac atcagtgaat gtctactttc tggtggccta ccgtgaatcc   1740
cgtaggctaa ttgccttctt taacacagga ggcacagcac gtccagcgcc aacatcaatg   1800
atctgtatgt acaacgtcga ttgtgggcgt gcacctcaaa caccgtaccc cacatttcaa   1860
tcgacactgc agtcaaaaga tgaggtggac aattctcaaa cccctgatga tgatgacatc   1920
tctctcgcag ggtcctttat aggcgacgag tttgatagcg tggatcaact cgaacgcgaa   1980
agggaagatc taatgaggag gttaagagat ctagacctcc ggcgctttca cgtc          2034
```

<210> SEQ ID NO 17
<211> LENGTH: 2037

<212> TYPE: DNA
<213> ORGANISM: Avian Nephritis Virus

<400> SEQUENCE: 17

```
atgcctggcc ctgccggccc tgtcaatggg ggcgctcgcc ccaaaactca aatggccaaa      60
cccaagaagg ctaaaaaatc tccatctcag aaaaagcctt ctcagcaaaa accactcaga     120
agggaaataa aaaaggtgga gaaacaggtg agagtgctca agaaacgcac taatgggccc     180
aagcagaatg atctcttcac aacaactgtt acgcttggga caatttctgg acagagtgac     240
aatggcctta ctaggcagat aaggctgcca cttaatccgc tacttctgaa atcatcagac     300
ggtggttcta caacaccact ctctatacgc ggttcaatgt atgagatgtg aaagttatc     360
agagcggaac tcatcgccac tcctctaaca ggtggtgcta atattgtggg ctccgtcggc     420
ttcatggtac tcacccttaa tgggcttgaa gcaactgcag actcaatcga ctccatcaaa     480
gccagaaagc atgtccagat accacttggt aggcttgcaa gactgaggct caccgcgcgt     540
gaatgcgcgg gtccgcgtga aggctggtgg cttactgata cttcccagtc accagctgac     600
tcgtatgggc cagcagtcga tcttatgatt gcctatgcaa ctacaaacct cctcaataca     660
tctggaggag ctagtgctac ctttctcggt actctctggc aagtcgaaat tagagtcacc     720
tatgctttca gcacctataa tcccaaacca ggtctgcaaa caatggtttc gcaaactctg     780
gctggatcaa atcatcaagt cacaattcgg caatcaacaa ctgatggctc ccttataatg     840
acaacaaatg ataccaacct cctttccatc cttactcccc gtgtcgcggg gcaaaggtca     900
ggaaagtccc agacggtttg gcgattgct ggagctgcgg ttgaagccgc cgctccactg     960
cttgggccgt ggggttggct tctaaagggg gcttttggc ttgtgagaaa aatctttggt    1020
gctagtgcac gtgacacgac ctcacagtac cagatctatc cttccattga gccgcaatg    1080
tctgaccaac caatctttgg tcaaactggt acatctacaa ctgtcactct gcccattgtg    1140
cacatttcag aagtgatgaa tcctaaccct gagaataatg acctatcaaa tcctacatct    1200
aggtcatttc cacctactcc gcctaccccct tctactgatc ccattcttcc tctggcggag    1260
ctaactggac aaccgggggt tccacctctt tacacctttg atggcagtac ttacaccca    1320
ccaactaatt ggctgggctc tactactttg ttaactggta ttccagcaca taaacgagtg    1380
actggtaact tgtctaactt tggagtcacc aacctccaaa tgtcaaaagt tactgccact    1440
gcaattgaga tttatgactt cacagacttt ggtgtctttt ttggcactgg tagttacctt    1500
ggtgaaggtg gcattcacac tgggaagact ttaatccatt ccttgatgtc tggtcaaacc    1560
ccgaacccct ggcttgctgc aaaccagtca gggacgacct ggtacctccc tacttgggtt    1620
ggctttccta caccaggtgc gggtgattac ttccttcaaa tgcaggatgt gacagacacg    1680
acaactcaca ctacatctgt gaatgtgtac ttcctggtag cttaccacca gtctcgaagg    1740
ctcatagcct tcttcaacac tggaggcaca gctcgtccag caccaacatc aatgctttgt    1800
ctctataatg ttgactgtgg gcgtgctcca caaacgccct accctacttt tcagtcaaca    1860
ctccaaagtc tgactcaatc tgaggtggat gcaaaaactg atcccgactc cgacgatgac    1920
atttcacttg cggggtcggt cattggcgac gagtttgata gtgtggatca tctcgaacgc    1980
gaaagagaag atttaatgag gaggctcaga gatctagacc tccggcgctt tcagatc       2037
```

<210> SEQ ID NO 18
<211> LENGTH: 2031
<212> TYPE: DNA
<213> ORGANISM: Avian Nephritis Virus

<400> SEQUENCE: 18

```
atgcctggcc ctgccggccc tgccaatggg ggcgttcgcc ccaaaactca atggcaaaa      60
cctaagaagg ctaagaaacc tccatctcag aaaaagcctt ctcaaaaacc actcaggaag    120
gaagtgaaga aggtggaaag acaggtaaag gtgctaaaga aacgcaccaa tggccctaag    180
cagaatgatg tgttcacaac aacagtcact cttggaacca tctcgggcca aaatgacaat    240
ggtctaacca ggcaaattcg ggtgcctttc aacccttac tttgtaagtc atctgacgt      300
ggttctacca caccactgtc aataagggt tcaatgtatc aaatgtggaa ggtgcttaag     360
gcagagctac gtgcaacacc actaacaggg gggcaaatg tggttggttc agtcggcttc     420
atggttctca ccctgaatgg gctcgaagcc actgcagatt ccatcgacac aataaaagca    480
agaaagcacg tgcagattcc dataggcaga agtgccgttc ttcgtattct tgcacgcgac    540
tgtgcggggc ctcgcgaggg ttggtggctt actgatactt caagttcacc agctgacgca    600
catgggcctg cggtcgatct catgatcgcc tataaaacat caaacttgct taatgtgtca    660
agtaccactg gacctcagcc ttttactggt accttatggc aggcggagct caaagtcact    720
tatgctttta gcacctatga cccgaaacct ggtcttcaga ctcttgtgtc agagacgcta    780
tctggtagcc atcaagttac tattcaaacc tcagcagacg acggttcact tataatgaca    840
acaactgata cgcaactgct ttcactcctt acgccacgta cgggtgacca gaagaagggg    900
aaatctccaa ctgtctgggc agttgcaggc gccgttgttg atgctgtagc tcctgtatta    960
ggaccctggg gctggctact aaaggcggc ttcttccttg ttaggaagat cttcggggct    1020
tctactcgga atgcgggagc gtcttatcag atttaccct caattgagca ggctatgtct    1080
gatcaaccaa tttttggtca gcaatctgga acaacacaag tgacactccc gcttgttcat    1140
gtttccgagg ttatgaaccc caactccgag agtaatgacc taaatccaac atctaggtca    1200
cttccaccta ccccgcctac tccatctact gatcccattc ttccttggc ggagctaact     1260
ggacaaccgg gggttccacc cctctacacc tttgacggca gtagctatac ccccctcaact   1320
aactggttgg gctctacaat tctactcaca ggtataccag cacataagag agttacaggt    1380
aatctctcaa actttggagt aaccaatctc cagatgtcca agttacagc tactgcactt     1440
gagatctatg atttcacaga ctttggagtc ttctttggaa caggaagcta tctcggagaa    1500
ggtggaatcc cccctggaac aaccctgatc cactccctaa tgtctggcca acaccaact    1560
cctccgccag cagcaaatca atctggcaca acttggtacc tgccatcgtg ggcaggtttt    1620
ccaccacctg gccagggcga ctactttctc caaacgcagg atgtcaccga cacaacaact   1680
cacacgacct cggttaatgt ctactttctc gtggcctacc gccagtctcg aaggcttaca    1740
gctttctttta atacaggagg cacagctcgt ccagcaccaa cttcaatgct atgcctctat    1800
aatgttgact gtgggcgtgc accacaaacg ccctacccta cctttcagtc aactctccaa    1860
agcctgaatc aaattgggt ggatgcaaaa cctgactccg actccgacga tgacatctca    1920
ctggcggggt catgcattgg cgacgagttt gagagtgtgg atcaactcga acgcgagaga    1980
gaagatttaa tgaggaggct aagagatcta gacctccggc gctttcagat c             2031
```

<210> SEQ ID NO 19
<211> LENGTH: 2025
<212> TYPE: DNA
<213> ORGANISM: Avian Nephritis Virus

<400> SEQUENCE: 19

```
atggctggcc ctgccggctc gtccaatggg ggcgctcgcc ccaaaactca atggcaaaa      60
```

```
tctaagaagg ctaagaaacc tccatctcag aaaaagcctt ctcaaaaacc actcaggaag      120
gaagtaaaaa aggtggaaag acaggtcaag gtgcttaaga aacgcaccaa tggccctaag      180
cagaatgatg tgtttacaac aacagtcact cttggaacca tctcgggcca aaatgataat      240
ggtctaacca ggcaaattcg ggtgcctttc aaccccttac tgtgtaagtc atctgatggt      300
ggttccacca caccactatc aataaggggt tcgatgtacc aaatgtggaa agtgcttaaa      360
gcagagcttc gtgcaacacc tctaacagga ggggcaaata tagtcggctc ggtcggcttt      420
atggtcctca ccctgaatgg gcttgaagcc actgcagatt ctattgacac aataaaagca      480
aggaagcacg tgcagattcc gattggcaga agtgccgttc tgcgtattct tgcgcgtgat      540
tgtgctgggc ctcgcgaggg ctggtggcta actgatacgt caagctcacc ggctgacgct      600
tatggacccg cagtcgacct tatggttgcc tacagaacat caaacttgct taacgtgtct      660
agtgccagta cacagcctca atctttcact ggtactctgt ggcaggcaga acttaaagtt      720
acttatgctt ttagcaccta tgacccaaaa cctggtcttc agactctcgt gtcagagacg      780
ctctccggca gccatcaagt caccattcaa gcttcagcag atgatggttc acttataatg      840
acaacaactg atacgcaact gctatcactc cttacgccac gtacgggtga ccagaagaag      900
ggcaaatctc caactgtctg gcagtcgct  ggtgctgttg ttgatgctgt agcccctgta      960
ttaggaccat ggggctggct tctcaagggt ggcttttttcc ttgttaggaa aatctttggg     1020
gtttcatctc gtaatgcggg ggcgtcttat cagatctacc cttcaattga gcaagctatg     1080
tctgaccaac caatctttgg tcagcaatct ggaacaggta cacagattac gctcccactt     1140
gttcatgtct ctgaggttat gaaccccaac tccgagagta atgacctgtc tgctccaaca     1200
tctagggcgc ttccacctgc acctgaacca gagcctgagc tcccactggc cctattagtt     1260
ggccagtcca acgtccctgc agtctatgag tacactgggg atgcttatac accacaacca     1320
aggtggacag gctcgaccat tttcctcact ggtattccct accatactag gctacaggt      1380 gctacacagt cttttggagt gagaactaac aatatgtcac cttcaaactg cacaacactt     1440
gacatctatg acttcacaaa ttttggagtc ttctttggca gtaatggcta cctctcacaa     1500
ggagccatac acacttcaag aacaatgatt cactcactca agactaatcc gaatataaac     1560
ccttggctag cagcaaatca atcttcaacc acgtggtcta tgcctacgtg gtctggctat     1620
cctacaccag gccaaggaga ttacttcctg caaatgcaag ataccactga ttcaactacc     1680
catacaacat ctgtgggttg ctatttctg gtgatgtatg gtgaatctcg gaaacttatt      1740 gccttttta acactggcac tggcacagca agacctgcac tttcatctat gatgtgcctc     1800
tataatgttg atgcaggaag agcaccagtg aggattcagg gctttcttct cagcccatca     1860
caaaattttg ttgaaactga caatcaggac ccagaagatg atgatgacat ctccatcgcc     1920
gggtcctgtc tgcaagatga gtttgattgt gtgggtcaac tcgaaaaaga aagagaagat     1980
ctaatgagga ggttaagaga tctagacctc cggcgctttc agatc                     2025

<210> SEQ ID NO 20
<211> LENGTH: 2040
<212> TYPE: DNA
<213> ORGANISM: Avian Nephritis Virus

<400> SEQUENCE: 20
atgcctggcc ctgccggccc tgccaatggg ggcgctcgcc ccaaaactca aatggtaaaa       60
cctaagaagg ccaagaaacc tccacctcag aaaaagcctt ctcaaaaacc actcaggaag      120
```

```
gaagtgaaga aggtggaaag acaggtaaag gtgcttaaga aacgcaccaa tggccctaag    180
cagaatgatg tgttcacaac aacagtcact cttggaacca tctcgggcca aaatgacaat    240
ggtctaacca ggcaaatccg ggtgcccttc aacccecttac tttgtaaatc atctgacggt    300
ggttctacca caccactgtc aattagggg tcaatgtatc aaatgtggaa ggtgcttaag    360
gcagagctac gtgcgacacc actaacaggg ggggcaaatg tagtcggttc agtcggcttt    420
atggttctca ccctgaacgg gctcgaagcc actgcagact ccattgacac aataaaagca    480
aggaaacatg tgcagattgc acttggcagg agtgctgctc ttcgcattct tgcccgtgac    540
tgcgcgggac ctcgcgaggg ctggtggctt actgatactt ctagttcccc ggctgactct    600
tatgggcctg cggttgatct tatgatcgcc tataaaacat ctaacttgct caatgtgtca    660
actgctggta tacctcaatc atttactggc acgctttggc aagtggagct caaagtcacc    720
tatgcgttta gcacttacga tccaaaacct ggtctgcaaa ctcttgtttc gcagactctg    780
gatgggtctc atcaagtcac actccaacaa tcaacaactg atggctccct cataatgaca    840
actactgatg ccacccttct ttctatcctt acccccccgcg ttgggggcca aaggtcggga    900
aagtctcaaa cggtctggtc gattgcagga gctgcggttg aggctgctgc cccgctgctt    960
ggtccgtggg gctggcttct taaggggggc ttttggcttg tgagaaaaat ttttggtgct   1020
tccgcgcgtg acacgacctc acagtaccaa atttatcctt ccattgagtc tgcaatgtct   1080
gaccaaccaa ttttttggcca gactggtatt tcaactgtca ctctgcccat tgtgcacatt   1140
tccgaagtga tgaatcctaa tcctgagaac aatgacctgt ctaatccaac ttctaggtca   1200
cttccaccta ctccacctac cccacctgct caggagaaaa ttctaccact tactctcctt   1260
gagggtcaac caggtgttcc tgccttatat acatttaacc ccagcacgga agcctataca   1320
gcagcaactg gctggacagg ggggacgcta cttcttaccg gcgtaccaga gtacgaactt   1380
cgcagcggct cctcacaaca atttggggtc cgagtgacta cctcaccagg tcttccacca   1440
gctgcagcaa catcgataca aatttatgat tttacaaaat ttggtatctt ctttggtgct   1500
ggtgcttttc ttgggcaagg aggagtccat acagcaaaga ctcttctaac agcaattaca   1560
tcttctagca accccccctg gcttgcttgc cacagataca cctggagctg gcctgattgg   1620
cttgttacgg ctggttatcc taaacctgtg gagggtggct ggtggctgca gatgcaaaaa   1680
attggtgata ccacatctca tacaactcca gttggtatct acttcctggt ggcatataag   1740
gagatgcaac aacttgtggc ttttggcac acgggttccg gagcccaagc cgaacccact   1800
tctcttatgt gcctttataa tgttgatgca gggcgtgcac ctgtgagagt tccgcacttc   1860
attcttacaa ctactgcccg caatgaagtg gaggttgatg ggggtgatga ctcagacgac   1920
gacatctctc ttgctgggtc ttgtgttggc gacgagtttg agggtgtgga tcaactcgaa   1980
cgcgaaaggg cagaacttat gagcaggtta agagacctgg acctgcggcg ctttcagatc   2040
```

<210> SEQ ID NO 21
<211> LENGTH: 2046
<212> TYPE: DNA
<213> ORGANISM: Avian Nephritis Virus

<400> SEQUENCE: 21

```
atggctggcg gtgccaccgc acctgcgggc gctaagccca agcaacccaa gcaaaagcag     60
cagaaacctt gttctcagcg gaaaaagaaa attccgcaaa aacagaagtc catgaaacca    120
gtaaaacagg agttgaggaa agttgagaag caagtcaagg tccttaaagc tcggacaaat    180
ggacccaaag taaatgatac aatgaagact acagtcacag tgggtaccct tgtgggacaa    240
```

```
acacaaagtg gactcaaccg ccaacttagg gtctcattca atcctcttct catgaagtca      300
acagatggcg gtaatactac tccactttcc attcgtgctt caatgtacga gatgtggaaa      360
ccactgagtg tagagatcta tgccacgcca cttagtggct tttcaagcgt ggtaggttca      420
gttggcttta tggttcttac tctgaatgga cttgaggctt ccgcagactc aattgacact      480
ataaaggcca ggaaacacgt ccaaatggcg cttggtaggc cttataggct taaactaagt      540
gctcgtgaac ttgctggtcc ccgtgaaggc tggtggctcg ttgatacatc tgagtcgcct      600
gccgatgcat acggcccagc tgttgatctc atgctggctt atgcaacgga aaatctactc      660
gggacatcct ctggctccac aacttcatat acaggcacac tctggcaagt tgagatgaga      720
gttagctatg ctttctccac ctataaccca aaacctgggc tgcagactct catttcccaa      780
tccatcacgg gtggtcagac tgtaaccgtt caaccgtctc cggacgatgg ctctctcatt      840
atgactacta ccagtcaaca agtccttgca cttctaacac ccagggtagc gggccaaaag      900
aagggcaaat cccagacaat ttgggcaatt gctggttcag caattgatgc tgccgctaca      960
gtgcttggac cctggggcta cctttttaaaa ggtggcttct ggcttgttcg acttatatttt     1020 ggtggaacgt ctgctagaaa cccaacaaca cgccagtatc agatttaccc gtcggtcgag     1080
tcagctctta ccgaccaacc tattttttggc aatgctactg gcacccagag tgttactgtt     1140
ccaatctgcc atattacaga agttgtgaat ccaaatgcgg gaaagcaaca atttcactgg     1200
tccaacaacc aagtgcacca gcaccaccgg tgcccccccaa ctccaattca agatgtcatt     1260
ctaccactcg cagaattgac tgggcaagat ggagtgccag caaactacac cttcaatggt     1320
gattcttata cagctcagtc cgattggagg gggtctacgc ttgttctcac tggaattcca     1380
agacataagc gagtggccgg gaacctgtcc aattttggtg tggtgactaa ccagatgtca     1440
aaagtcacca caaccgcact tgagatatat gacttcaccg acttcgggat cttcttcggt     1500
ggaggctacc aactccagga aggtggaata catactggta aaacactggt acactcgctc     1560
atgacaggtg ctccaataaa accttggctc tatgctaccc aatcatcaac aacctggtac     1620
tggcctgatt ggactggctt cccaaaaacct ggggaaggag actatttttct ccaagtgcaa     1680 gatacaaccg atagaacaac acatacaacg tgtgttggta tctacatcgt tgttgcttat     1740
cgccagtcac gaaggttaat agccttcttt aataatgcag gtccagtccg ggcggcgccc     1800
acaactatgc tttgtctata caatgtggat gcgggccgag caccagcaac accttataac     1860
accttccaac tcacactcca aagtgaaaac tctgacccaa attctccatc tgatgatgaa     1920
gatgatgaca tctcaattgc tggctcctgt ctccaagacg agtttgactg tgtggatcaa     1980
ctcgaaaaag aaagagaaga tcttatgagg aggttaagag atctagacct ccggcgcttt     2040
cagagc                                                                2046
```

<210> SEQ ID NO 22
<211> LENGTH: 2046
<212> TYPE: DNA
<213> ORGANISM: Avian Nephritis Virus

<400> SEQUENCE: 22

```
atggctggcg gtgccaccgc acttgcgggc gctaagccca acaacccaa acagaagcag       60 cagaaacctg gctctcagcg gaaaaagaaa cctccgcaaa acagaaatg tatgaagcca      120 gttaaacagg agctgaggaa agtcgaaaaa caagtcaaag tcctaaaggc tcggacaaat      180
ggacctaaag ttaatgacac aatgaagacc acagtcacag tgggcactct ggtgggacaa      240
```

```
acacaaagtg gacttaaccg ccaactcagg gtttctttca acccgcttct tatgaagtca    300
acagatggcg gtaacactac tccactttcc atccgtgcct caatgtacga gatgtggaaa    360
gcactgagtg tagaaatcta tgccacgcca cttagtggtt tttcgagcgt ggtaggctca    420
gttggcttta tggtcctgac actgaatggg cttgaggctt ccgcggattc aatcgacacc    480
atcaaggcaa gaagacatgt ccaaatggca cttggtaggc cctataggtt gaaactaaac    540
gcccgtgaac tcgctggtcc ccgcgagggc tggtggctgg ttgacacatc tgagacgcct    600
gccgaagcat acggcccggc agttgatctt atgctggcct atgcgacaga aaatctactt    660
gggacgtctt ctggctctac aacttcatac acaggtacac tctggcaagt tgaaatgagg    720
gttagttatg ctttctccac ctacaatcca aaacctgggc tgcaaactct catttctcaa    780
cccatcactg gtggccaaac tgtgaccatt caaccgtctc cggacgatgg ctcactcata    840
atgactacca ctagtcaaca agtccttgca ctcctaacac ctagggtagc ggcaggtcaa    900
aagaagggca atcccaaac aatttgggca attgccggtt cagcagttga cgccgctgcc    960
acagtgctcg gaccctgggg ctacctcctg aagggtggtt tctggctcgt tcgactcatt   1020
tttggtgggg gatctgccag aaacacaaca accaggcagt tccagatcta cccgtcggtc   1080
gagtcagcac ttgccgacca gcctatttat ggcaattcta ctggaaccca gagtgttacc   1140
gttccaattt gccacatcac tgaagttgtg aatccgaacg cggaaagtaa taacctcact   1200
ctccccacaa cctcagcacc tgcaccacca acaccaccat caccatctga agaccccata   1260
ctaccgctgg cagaattaac tggccagcct ggggtcccac ctctttacac ttttgatggc   1320
agtagctata ctccagcgcc caactggctg ggtcaacac tattactaac tgggatacca   1380
gcacataaac gagtgactgg taatttggcc aactttggag ttaccaacct ccaaatgtca   1440
aaagttactg ccactgcagt tgagatctat gatttcacag attttggtgt gttcttttggc   1500
actggcagct tccttggcga aggtggcatt cacacaggga agactctgat ctattccctg   1560
atgtctggtc aagacccaaa accctggctg gcggcaaacc agtcaggaac aacctggtac   1620
cttccttctt gggttggttt tcccacacca ggtgcgggtg actacttcct gcaaatgcag   1680
gacacaacag acacgacaac tcacacaaca tcagtgaatg tctactttct ggttgcctac   1740
cgtcaatcac gtaggctgat cgctttcttt aacacagggg gcacagcaag accagcgcca   1800
acatcaatgc tctgcatgta caacgtcgac tgtgggcgtg ctcctgcaac acctatcccc   1860
acataccagt cggctctgca atcaaaagtt gaggtggcta attctgaaac ccttgactcc   1920
gacgacgaca tctcactggc ggggtcatgc attggcgacg agttgaaag tgtggatcaa   1980
ctcgaacgcg aaagagaaga tctaatgagg aggctcagag atctcgacct ccggcgcttt   2040
cacatc                                                              2046
```

<210> SEQ ID NO 23
<211> LENGTH: 679
<212> TYPE: PRT
<213> ORGANISM: Avian Nephritis Virus <400>

```
His Gln Val Asn Ala Leu Lys Lys Thr Asn Gly Pro Lys Met Asn
    50                  55                  60
Asp Met Met Lys Thr Thr Val Thr Ile Gly Val Ile Gln Gly Gln Thr
 65              70                  75                  80
Gln Ser Gly Leu Ser Arg Gln Leu Arg Val Pro Leu Asn Pro Leu Leu
                 85                  90                  95
Met Lys Ser Thr Glu Gly Leu Ala Ala Thr Pro Leu Ser Ile Arg Ser
             100                 105                 110
Ser Cys Tyr Glu Leu Trp Lys Ala Leu His Val Glu Leu Phe Ala Thr
             115                 120                 125
Pro Leu Thr Gly Phe Ser Asn Val Val Gly Ser Val Gly Phe Met Ala
     130                 135                 140
Leu Thr Leu Asn Gly Leu Glu Ala Thr Ala Asp Ser Ile Asp Ser Ile
 145             150                 155                 160
Lys Ala Arg Lys His Tyr Gln Met Ala Leu Gly Arg Pro Ala Arg Leu
                 165                 170                 175
Lys Leu Thr Ala Arg Glu Leu Ala Gly Pro Arg Glu Gly Trp Trp Leu
             180                 185                 190
Thr Asp Thr Ser Glu Ser Pro Ala Asp Ala Tyr Gly Pro Ala Ile Asp
             195                 200                 205
Leu Met Ile Ala Tyr Lys Thr Glu Asn Leu Leu Asn Thr Thr Gly Ser
 210             215                 220
Thr Thr Ser Thr His Thr Gly Pro Leu Trp Gln Ile Glu Ala Arg Ala
 225                 230                 235                 240
Thr Tyr Gly Phe Ala Asn Tyr Asn Pro Lys Pro Gly Leu Gln Thr Leu
                 245                 250                 255
Val Ser Gln Thr Leu Thr Asn Gly Gln Thr Val Thr Ile Gln Pro Ser
             260                 265                 270
Pro Asn Asp Gly Ser Leu Ile Met Thr Thr Ser Leu Gln Val Arg
     275                 280                 285
Ser Leu Leu Ser Pro Arg Ala Gly Asp Pro Lys Lys Gly Lys Ser Gln
     290                 295                 300
Thr Ile Trp Ala Ile Ala Gly Ser Ala Val Asp Ala Ala Ala Thr Val
 305                 310                 315                 320
Leu Gly Pro Trp Gly Trp Leu Leu Lys Gly Gly Phe Trp Leu Val Arg
                 325                 330                 335
Gln Ile Phe Gly Gly Ser Ser Asn Ala Ala Gly Ser Ser Tyr Gln Ile
             340                 345                 350
Tyr Ser Ser Leu Glu Ser Ala Met Ala Asp Gln Pro Ile Phe Gly Ala
             355                 360                 365
Gln Thr Gly Thr Gln Ser Ile Thr Val Pro Val His Ile Ser Glu
     370                 375                 380
Val Leu Asn Pro Asn Pro Met Ser Asn Gln Val Pro Thr Pro Ser Ala
 385                 390                 395                 400
Gly Ser Ala Pro Ala Pro Pro Thr Pro Thr Pro Ile Gln Asp Ile
                 405                 410                 415
Ile Leu Pro Leu Ala Glu Leu Thr Gly Gln Asp Gly Val Pro Ala Asn
                 420                 425                 430
Tyr Thr Phe Asn Gly Asp Ser Tyr Thr Gly Gln Gly Asp Trp Arg Gly
                 435                 440                 445
Ser Thr Leu Val Leu Thr Gly Ile Pro Arg His Lys Arg Val Thr Gly
     450                 455                 460
Asn Leu Ser Asn Phe Gly Val Thr Val Asn Gln Met Ser Lys Val Thr
```

```
            465                 470                 475                 480
        Thr Thr Ala Leu Glu Ile Tyr Asp Phe Thr Asp Phe Gly Val Ser Phe
                        485                 490                 495
        Gly Gly Gly Tyr Gln Leu Gln Glu Gly Gly Val His Thr Gly Lys Thr
                        500                 505                 510
        Met Val His Ser Leu Met Thr Gly Ala Pro Ile Lys Pro Trp Leu Tyr
                        515                 520                 525
        Ala Thr Gln Ser Ser Thr Thr Trp Tyr Trp Pro Thr Trp Thr Gly Phe
                        530                 535                 540
        Pro Gln Pro Gly Pro Gly Asp Tyr Phe Leu Gln Met Gln Asp Thr Thr
        545                 550                 555                 560
        Asp Arg Thr Thr His Thr Thr Cys Val Ser Val Tyr Leu Leu Val Ala
                        565                 570                 575
        Tyr Gln Ala Ser Arg Arg Leu Ile Ala Phe Tyr Asn Asn Gly Gly Thr
                        580                 585                 590
        Ala Arg Ala Ala Pro Thr Thr Met Leu Cys Leu Tyr Asn Val Asp Ala
                        595                 600                 605
        Gly Arg Ala Pro Gln Thr Pro Tyr Asn Thr Phe Gln Leu Thr Leu Gln
                        610                 615                 620
        Ser Glu Val Ala Asp Pro Asn Ser Pro Ser Glu Asp Glu Asp Asp Asp
        625                 630                 635                 640
        Ile Ser Leu Ala Gly Ser Cys Leu Gln Asp Glu Phe Asp Cys Val Asp
                        645                 650                 655
        Gln Leu Glu Lys Glu Arg Glu Asp Leu Met Arg Arg Leu Arg Asp Leu
                        660                 665                 670
        Asp Leu Arg Arg Phe Gln Ile
                        675

<210> SEQ ID NO 24
<211> LENGTH: 679
<212> TYPE: PRT
<213> ORGANISM: Avian Nephritis Virus

<400> SEQUENCE: 24

Met Ala Gly Gly Ala Thr Ala Pro Ala Gly Ala Lys Pro Lys Gln Ser
        1               5                   10                  15
        Lys Gln Lys Gln Lys Thr Pro Ser Gln Arg Lys Leu Lys Ser Thr Gln
                        20                  25                  30
        Lys Ala Lys Gln Gln Lys Pro Pro Val Lys Thr Val Arg Arg Leu Glu
                        35                  40                  45
        Arg Gln Val Asn Ala Leu Lys Lys Thr Asn Gly Pro Lys Met Asn
                        50                  55                  60
        Asp Met Met Lys Thr Thr Val Thr Ile Gly Val Ile Gln Gly Gln Thr
        65                  70                  75                  80
        Gln Ser Gly Leu Ser Arg Gln Leu Arg Val Pro Leu Asn Pro Leu Leu
                        85                  90                  95
        Met Lys Ser Thr Glu Gly Leu Ala Ala Thr Pro Leu Ser Ile Arg Ser
                        100                 105                 110
        Ser Cys Tyr Glu Leu Trp Lys Ala Leu His Val Glu Leu Phe Ala Thr
                        115                 120                 125
        Pro Leu Thr Gly Phe Ser Asn Val Val Gly Ser Val Gly Phe Met Ala
                        130                 135                 140
        Leu Thr Leu Asn Gly Leu Glu Ala Thr Ala Asp Ser Ile Asp Ser Ile
        145                 150                 155                 160
```

```
Lys Ala Arg Lys His Tyr Gln Met Ala Leu Gly Arg Pro Ala Arg Leu
            165                 170                 175

Lys Leu Thr Ala Arg Glu Leu Ala Gly Pro Arg Glu Gly Trp Trp Leu
            180                 185                 190

Thr Asp Thr Ser Glu Ser Pro Ala Asp Ala Tyr Gly Pro Ala Ile Asp
            195                 200                 205

Leu Met Ile Ala Tyr Lys Thr Glu Asn Leu Leu Asn Thr Thr Gly Ser
            210                 215                 220

Thr Thr Ser Thr Tyr Thr Gly Pro Leu Trp Gln Ile Glu Ala Arg Val
225                 230                 235                 240

Thr Tyr Gly Phe Ala Thr Tyr Asn Pro Lys Pro Gly Leu Gln Thr Leu
            245                 250                 255

Val Ser Gln Thr Leu Thr Asn Gly Gln Thr Val Thr Ile Gln Pro Ser
            260                 265                 270

Pro Thr Asp Gly Ser Leu Ile Met Thr Thr Asn Ser Leu Gln Ile Arg
            275                 280                 285

Thr Leu Leu Ser Pro Arg Ala Gly Asp Pro Lys Lys Gly Lys Ser Gln
            290                 295                 300

Thr Ile Trp Ala Ile Ala Gly Ser Ala Val Asp Ala Ala Thr Val
305                 310                 315                 320

Leu Gly Pro Trp Gly Trp Leu Leu Lys Gly Gly Phe Trp Leu Val Arg
            325                 330                 335

Leu Ile Phe Gly Gly Ser Thr Asn Ala Thr Thr Ser Ser Tyr Gln Ile
            340                 345                 350

Tyr Ser Ser Leu Glu Ser Ala Met Ala Asp Gln Pro Ile Tyr Gly Ala
            355                 360                 365

Gln Thr Gly Thr Gln Ser Ile Thr Val Pro Val Val His Val Ser Glu
            370                 375                 380

Val Leu Asn Pro Asn Pro Val Ser Asn Gln Val Pro Thr Pro Ser Thr
385                 390                 395                 400

Gly Ser Ala Pro Ala Pro Pro Thr Pro Ala Pro Ser Glu Asp Pro
            405                 410                 415

Ile Leu Pro Leu Ala Glu Leu Thr Gly Gln Pro Gly Val Pro Pro Leu
            420                 425                 430

Tyr Thr Phe Asp Gly Ser Thr Tyr Thr Pro Pro Thr Asn Trp Leu Gly
            435                 440                 445

Ser Thr Leu Leu Leu Thr Gly Ile Pro Ala His Lys Arg Val Thr Gly
            450                 455                 460

Asn Leu Ala Asn Phe Gly Val Thr Asn Leu Gln Met Ser Lys Val Thr
465                 470                 475                 480

Ala Thr Ala Ile Glu Val Tyr Asp Phe Thr Asp Phe Gly Val Phe Phe
            485                 490                 495

Gly Thr Gly Thr Tyr Leu Gly Glu Gly Gly Ile His Thr Gly Lys Thr
            500                 505                 510

Leu Val Tyr Ser Leu Met Ser Gly Gln Thr Pro Asn Pro Trp Leu Ala
            515                 520                 525

Ala Asn Gln Ser Gly Thr Thr Trp Tyr Leu Pro Ser Trp Val Gly Phe
            530                 535                 540

Pro Thr Pro Gly Ala Gly Asp Tyr Phe Leu Gln Met Gln Asp Val Thr
545                 550                 555                 560

Asp Thr Thr Thr His Thr Thr Ser Val Asn Val Tyr Phe Leu Val Ala
            565                 570                 575

Tyr Arg Glu Ser Arg Arg Leu Ile Ala Phe Phe Asn Thr Gly Gly Thr
```

```
                     580                 585                 590
Ala Arg Pro Ala Pro Ala Ser Met Ile Cys Met Tyr Asn Val Asp Cys
                595                 600                 605

Gly Arg Ala Pro Gln Thr Pro Tyr Pro Thr Phe Gln Ser Thr Leu Gln
            610                 615                 620

Pro Lys Asp Glu Val Asp Asn Ser Gln Thr Pro Asp Asp Asp Asp Asp
625                 630                 635                 640

Ile Ser Leu Ala Gly Ser Phe Ile Gly Asp Glu Phe Asp Ser Val Asp
                645                 650                 655

Gln Leu Glu Arg Glu Arg Glu Asp Leu Met Arg Arg Leu Arg Asp Leu
            660                 665                 670

Asp Leu Arg Arg Phe His Ile
        675

<210> SEQ ID NO 25
<211> LENGTH: 678
<212> TYPE: PRT
<213> ORGANISM: Avian Nephritis Virus

<400> SEQUENCE: 25

Met Ala Gly Gly Ala Thr Ala Pro Ala Gly Ala Lys Pro Lys Gln Pro
1               5                   10                  15

Lys Gln Lys Gln Lys Thr Ser Cys Gln Arg Lys Ser Lys Pro Thr Gln
            20                  25                  30

Lys Val Lys Gln Gln Lys Pro Pro Val Lys Thr Val Arg Arg Leu Glu
        35                  40                  45

Arg Gln Val Asn Ala Leu Lys Lys Thr Asn Gly Pro Lys Met Asn
    50                  55                  60

Asp Ile Met Lys Thr Thr Val Thr Leu Gly Val Ile Gln Gly Gln Thr
65                  70                  75                  80

Gln Ser Gly Leu Ser Arg Gln Leu Arg Val Pro Leu Asn Pro Leu Leu
                85                  90                  95

Met Lys Ser Thr Glu Gly Leu Ala Ala Thr Pro Leu Ser Ile Arg Ser
            100                 105                 110

Ser Cys Tyr Glu Leu Trp Lys Ala Leu His Val Glu Leu Phe Ala Thr
        115                 120                 125

Pro Leu Thr Gly Phe Ser Asn Val Val Gly Ser Val Gly Phe Met Ala
    130                 135                 140

Leu Thr Leu Asn Gly Leu Glu Ala Thr Ala Asp Ser Ile Asp Ser Ile
145                 150                 155                 160

Lys Ala Arg Lys His Tyr Gln Met Ala Leu Gly Arg Pro Ala Arg Leu
                165                 170                 175

Lys Leu Thr Ala Arg Glu Leu Ala Gly Pro Arg Glu Gly Trp Trp Leu
            180                 185                 190

Thr Asp Thr Ser Glu Ser Pro Ala Asp Ala Tyr Gly Pro Ala Ile Asp
        195                 200                 205

Leu Met Ile Ala Tyr Lys Thr Glu Asn Leu Leu Asn Thr Ser Gly Ser
    210                 215                 220

Thr Thr Ser Thr Tyr Thr Gly Pro Leu Trp Gln Ile Glu Ala Arg Val
225                 230                 235                 240

Thr Tyr Gly Phe Ala Thr Tyr Asn Pro Lys Pro Gly Leu Gln Thr Leu
                245                 250                 255

Val Ser Gln Ser Leu Thr Asn Gly Gln Thr Val Thr Ile Gln Pro Ser
            260                 265                 270
```

```
Pro Thr Asp Gly Ser Leu Ile Met Thr Thr Asn Ser Leu Gln Ile Gln
            275                 280                 285

Ser Leu Leu Ser Pro Arg Val Asp Gly Pro Gln Lys Gly Lys Ser Gln
    290                 295                 300

Thr Ile Trp Ala Ile Ala Gly Ser Ala Val Asp Ala Ala Ala Thr Val
305                 310                 315                 320

Leu Gly Pro Trp Gly Trp Leu Leu Lys Gly Gly Phe Trp Leu Val Arg
                325                 330                 335

Leu Ile Phe Gly Gly Ser Ser Asn Ala Ala Gly Ser Ser Tyr Gln Leu
            340                 345                 350

Tyr Ser Ser Leu Glu Ser Ala Met Ala Asp Gln Pro Ile Tyr Gly Ala
    355                 360                 365

Gln Thr Gly Thr Gln Ser Ile Thr Val Pro Val Val His Ile Ser Glu
    370                 375                 380

Val Leu Asn Pro Ser Pro Met Phe Asn Gln Val Ser Val Pro Thr Thr
385                 390                 395                 400

Gly Ser Ala Pro Ala Pro Pro Thr Pro Ala Pro Ser Glu Asp Pro
                405                 410                 415

Ile Leu Pro Leu Ala Glu Leu Thr Gly Gln Pro Gly Val Pro Pro Leu
                420                 425                 430

Tyr Thr Phe Asp Gly Ser Thr Tyr Thr Pro Pro Thr Asn Trp Leu Gly
            435                 440                 445

Ser Thr Leu Leu Leu Thr Gly Ile Pro Ala His Lys Arg Val Thr Gly
    450                 455                 460

Asn Ser Ala Asn Phe Gly Val Thr Asn Leu Gln Met Ser Lys Val Thr
465                 470                 475                 480

Ala Thr Ala Ile Glu Val Tyr Asp Phe Thr Asp Phe Gly Val Phe Phe
                485                 490                 495

Gly Thr Gly Thr Tyr Leu Gly Glu Gly Gly Ile His Thr Gly Lys Thr
            500                 505                 510

Leu Val Tyr Ser Leu Met Ser Gly Gln Thr Pro Lys Pro Trp Leu Ala
    515                 520                 525

Ala Asn Gln Ser Gly Thr Thr Trp Tyr Leu Pro Ser Trp Val Gly Phe
530                 535                 540

Pro Thr Pro Gly Ala Gly Asp Tyr Phe Leu Gln Met Gln Asp Val Thr
545                 550                 555                 560

Asp Thr Thr Thr His Thr Thr Ser Val Asn Val Tyr Phe Leu Val Ala
                565                 570                 575

Tyr Arg Glu Ser Arg Arg Leu Ile Ala Phe Phe Asn Thr Gly Gly Thr
            580                 585                 590

Ala Arg Pro Ala Pro Thr Ser Met Ile Cys Met Tyr Asn Val Asp Cys
    595                 600                 605

Gly Arg Ala Pro Gln Thr Pro Tyr Pro Thr Phe Gln Ser Thr Leu Gln
    610                 615                 620

Ser Lys Asp Glu Val Asp Asn Ser Gln Thr Pro Asp Asp Asp Ile
625                 630                 635                 640

Ser Leu Ala Gly Ser Phe Ile Gly Asp Glu Phe Asp Ser Val Asp Gln
                645                 650                 655

Leu Glu Arg Glu Arg Glu Asp Leu Met Arg Arg Leu Arg Asp Leu Asp
            660                 665                 670

Leu Arg Arg Phe His Ile
            675
```

<210> SEQ ID NO 26
<211> LENGTH: 679
<212> TYPE: PRT
<213> ORGANISM: Avian Nephritis Virus

<400> SEQUENCE: 26

```
Met Pro Gly Pro Ala Gly Pro Val Asn Gly Gly Ala Arg Pro Lys Thr
1               5                   10                  15

Gln Met Ala Lys Pro Lys Lys Ala Lys Lys Ser Pro Ser Gln Lys Lys
            20                  25                  30

Pro Ser Gln Gln Lys Pro Leu Arg Arg Glu Ile Lys Lys Val Glu Lys
        35                  40                  45

Gln Val Arg Val Leu Lys Lys Arg Thr Asn Gly Pro Lys Gln Asn Asp
    50                  55                  60

Leu Phe Thr Thr Thr Val Thr Leu Gly Thr Ile Ser Gly Gln Ser Asp
65                  70                  75                  80

Asn Gly Leu Thr Arg Gln Ile Arg Leu Pro Leu Asn Pro Leu Leu Leu
                85                  90                  95

Lys Ser Ser Asp Gly Gly Ser Thr Thr Pro Leu Ser Ile Arg Gly Ser
            100                 105                 110

Met Tyr Glu Met Trp Lys Val Ile Arg Ala Glu Leu Ile Ala Thr Pro
        115                 120                 125

Leu Thr Gly Gly Ala Asn Ile Val Gly Ser Val Gly Phe Met Val Leu
    130                 135                 140

Thr Leu Asn Gly Leu Glu Ala Thr Ala Asp Ser Ile Asp Ser Ile Lys
145                 150                 155                 160

Ala Arg Lys His Val Gln Ile Pro Leu Gly Arg Leu Ala Arg Leu Arg
                165                 170                 175

Leu Thr Ala Arg Glu Cys Ala Gly Pro Arg Glu Gly Trp Trp Leu Thr
            180                 185                 190

Asp Thr Ser Gln Ser Pro Ala Asp Ser Tyr Gly Pro Ala Val Asp Leu
        195                 200                 205

Met Ile Ala Tyr Ala Thr Thr Asn Leu Leu Asn Thr Ser Gly Gly Ala
    210                 215                 220

Ser Ala Thr Phe Leu Gly Thr Leu Trp Gln Val Glu Ile Arg Val Thr
225                 230                 235                 240

Tyr Ala Phe Ser Thr Tyr Asn Pro Lys Pro Gly Leu Gln Thr Met Val
                245                 250                 255

Ser Gln Thr Leu Ala Gly Ser Asn His Gln Val Thr Ile Arg Gln Ser
            260                 265                 270

Thr Thr Asp Gly Ser Leu Ile Met Thr Thr Asn Asp Thr Asn Leu Leu
        275                 280                 285

Ser Ile Leu Thr Pro Arg Val Ala Gly Gln Arg Ser Gly Lys Ser Gln
    290                 295                 300

Thr Val Trp Ala Ile Ala Gly Ala Ala Val Glu Ala Ala Ala Pro Leu
305                 310                 315                 320

Leu Gly Pro Trp Gly Trp Leu Leu Lys Gly Gly Phe Trp Leu Val Arg
                325                 330                 335

Lys Ile Phe Gly Ala Ser Ala Arg Asp Thr Thr Ser Gln Tyr Gln Ile
            340                 345                 350

Tyr Pro Ser Ile Glu Ala Ala Met Ser Asp Gln Pro Ile Phe Gly Gln
        355                 360                 365

Thr Gly Thr Ser Thr Thr Val Thr Leu Pro Ile Val His Ile Ser Glu
    370                 375                 380
```

```
Val Met Asn Pro Asn Pro Glu Asn Asn Asp Leu Ser Asn Pro Thr Ser
385                 390                 395                 400

Arg Ser Phe Pro Thr Pro Thr Pro Ser Thr Asp Pro Ile Leu
            405                 410                 415

Pro Leu Ala Glu Leu Thr Gly Gln Pro Gly Val Pro Pro Leu Tyr Thr
            420                 425                 430

Phe Asp Gly Ser Thr Tyr Thr Pro Pro Thr Asn Trp Leu Gly Ser Thr
            435                 440                 445

Thr Leu Leu Thr Gly Ile Pro Ala His Lys Arg Val Thr Gly Asn Leu
            450                 455                 460

Ser Asn Phe Gly Val Thr Asn Leu Gln Met Ser Lys Val Thr Ala Thr
465                 470                 475                 480

Ala Ile Glu Ile Tyr Asp Phe Thr Asp Phe Gly Val Phe Gly Thr
                485                 490                 495

Gly Ser Tyr Leu Gly Glu Gly Gly Ile His Thr Gly Lys Thr Leu Ile
                500                 505                 510

His Ser Leu Met Ser Gly Gln Thr Pro Asn Pro Trp Leu Ala Ala Asn
            515                 520                 525

Gln Ser Gly Thr Thr Trp Tyr Leu Pro Thr Trp Val Gly Phe Pro Thr
            530                 535                 540

Pro Gly Ala Gly Asp Tyr Phe Leu Gln Met Gln Asp Val Thr Asp Thr
545                 550                 555                 560

Thr Thr His Thr Thr Ser Val Asn Val Tyr Phe Leu Val Ala Tyr His
                565                 570                 575

Gln Ser Arg Arg Leu Ile Ala Phe Phe Asn Thr Gly Thr Ala Arg
            580                 585                 590

Pro Ala Pro Thr Ser Met Leu Cys Leu Tyr Asn Val Asp Cys Gly Arg
            595                 600                 605

Ala Pro Gln Thr Pro Tyr Pro Thr Phe Gln Ser Thr Leu Gln Ser Leu
            610                 615                 620

Thr Gln Ser Glu Val Asp Ala Lys Thr Asp Pro Asp Ser Asp Asp Asp
625                 630                 635                 640

Ile Ser Leu Ala Gly Ser Val Ile Gly Asp Glu Phe Asp Ser Val Asp
                645                 650                 655

His Leu Glu Arg Glu Arg Glu Asp Leu Met Arg Arg Leu Arg Asp Leu
                660                 665                 670

Asp Leu Arg Arg Phe Gln Ile
            675
```

<210> SEQ ID NO 27
<211> LENGTH: 677
<212> TYPE: PRT
<213> ORGANISM: Avian Nephritis Virus

<400> SEQUENCE: 27

```
Met Pro Gly Pro Ala Gly Pro Ala Asn Gly Gly Val Arg Pro Lys Thr
1               5                   10                  15

Gln Met Ala Lys Pro Lys Lys Ala Lys Lys Pro Pro Ser Gln Lys Lys
            20                  25                  30

Pro Ser Gln Lys Pro Leu Arg Lys Glu Val Lys Val Glu Arg Gln
        35                  40                  45

Val Lys Val Leu Lys Lys Arg Thr Asn Gly Pro Lys Gln Asn Asp Val
    50                  55                  60

Phe Thr Thr Thr Val Thr Leu Gly Thr Ile Ser Gly Gln Asn Asp Asn
65                  70                  75                  80
```

```
Gly Leu Thr Arg Gln Ile Arg Val Pro Phe Asn Pro Leu Leu Cys Lys
                85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
        115                 120                 125

Thr Gly Gly Ala Asn Val Val Gly Ser Val Gly Phe Met Val Leu Thr
    130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
                165                 170                 175

Leu Ala Arg Asp Cys Ala Gly Pro Arg Glu Gly Trp Trp Leu Thr Asp
            180                 185                 190

Thr Ser Ser Ser Pro Ala Asp Ala His Gly Pro Ala Val Asp Leu Met
            195                 200                 205

Ile Ala Tyr Lys Thr Ser Asn Leu Leu Asn Val Ser Ser Thr Thr Gly
        210                 215                 220

Pro Gln Pro Phe Thr Gly Thr Leu Trp Gln Ala Glu Leu Lys Val Thr
225                 230                 235                 240

Tyr Ala Phe Ser Thr Tyr Asp Pro Lys Pro Gly Leu Gln Thr Leu Val
                245                 250                 255

Ser Glu Thr Leu Ser Gly Ser His Gln Val Thr Ile Gln Thr Ser Ala
            260                 265                 270

Asp Asp Gly Ser Leu Ile Met Thr Thr Thr Asp Thr Gln Leu Leu Ser
            275                 280                 285

Leu Leu Thr Pro Arg Thr Gly Asp Gln Lys Lys Gly Lys Ser Pro Thr
290                 295                 300

Val Trp Ala Val Ala Gly Ala Val Asp Ala Val Ala Pro Val Leu
305                 310                 315                 320

Gly Pro Trp Gly Trp Leu Leu Lys Gly Gly Phe Leu Val Arg Lys
                325                 330                 335

Ile Phe Gly Ala Ser Thr Arg Asn Ala Gly Ala Ser Tyr Gln Ile Tyr
            340                 345                 350

Pro Ser Ile Glu Gln Ala Met Ser Asp Gln Pro Ile Phe Gly Gln Gln
        355                 360                 365

Ser Gly Thr Thr Gln Val Thr Leu Pro Leu Val His Val Ser Glu Val
    370                 375                 380

Met Asn Pro Asn Ser Glu Ser Asn Asp Leu Asn Pro Thr Ser Arg Ser
385                 390                 395                 400

Leu Pro Pro Thr Pro Pro Thr Pro Ser Thr Asp Pro Ile Leu Pro Leu
                405                 410                 415

Ala Glu Leu Thr Gly Gln Pro Gly Val Pro Pro Leu Tyr Thr Phe Asp
            420                 425                 430

Gly Ser Ser Tyr Thr Pro Ser Thr Asn Trp Leu Gly Ser Thr Ile Leu
        435                 440                 445

Leu Thr Gly Ile Pro Ala His Lys Arg Val Thr Gly Asn Leu Ser Asn
    450                 455                 460

Phe Gly Val Thr Asn Leu Gln Met Ser Lys Val Thr Ala Thr Ala Leu
465                 470                 475                 480

Glu Ile Tyr Asp Phe Thr Asp Phe Gly Val Phe Phe Gly Thr Gly Ser
                485                 490                 495
```

Tyr Leu Gly Glu Gly Gly Ile His Thr Gly Lys Thr Leu Ile His Ser
            500                 505                 510

Leu Met Ser Gly Gln Thr Pro Asn Pro Trp Leu Ala Ala Asn Gln Ser
        515                 520                 525

Gly Thr Thr Trp Tyr Leu Pro Ser Trp Ala Gly Phe Pro Gln Pro Gly
    530                 535                 540

Gln Gly Asp Tyr Phe Leu Gln Met Gln Asp Val Thr Asp Thr Thr Thr
545                 550                 555                 560

His Thr Thr Ser Val Asn Val Tyr Phe Leu Val Ala Tyr Arg Gln Ser
            565                 570                 575

Arg Arg Leu Ile Ala Phe Phe Asn Thr Gly Gly Thr Ala Arg Pro Ala
        580                 585                 590

Pro Thr Ser Met Leu Cys Leu Tyr Asn Val Asp Cys Gly Arg Ala Pro
    595                 600                 605

Gln Thr Pro Tyr Pro Thr Phe Gln Ser Thr Leu Gln Ser Leu Asn Gln
    610                 615                 620

Ile Gly Val Asp Ala Lys Pro Asp Ser Asp Ser Asp Asp Ile Ser
625                 630                 635                 640

Leu Ala Gly Ser Cys Ile Gly Asp Glu Phe Glu Ser Val Asp Gln Leu
            645                 650                 655

Glu Arg Glu Arg Glu Asp Leu Met Arg Arg Leu Arg Asp Leu Asp Leu
        660                 665                 670

Arg Arg Phe Gln Ile
        675

<210> SEQ ID NO 28
<211> LENGTH: 675
<212> TYPE: PRT
<213> ORGANISM: Avian Nephritis Virus

<400> SEQUENCE: 28

Met Ala Gly Pro Ala Gly Ser Ser Asn Gly Gly Ala Arg Pro Lys Thr
1               5                   10                  15

Gln Met Ala Lys Ser Lys Lys Ala Lys Lys Pro Pro Ser Gln Lys Lys
            20                  25                  30

Pro Ser Gln Lys Pro Leu Arg Lys Glu Val Lys Lys Val Glu Arg Gln
        35                  40                  45

Val Lys Val Leu Lys Lys Arg Thr Asn Gly Pro Lys Gln Asn Asp Val
    50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
            85                  90                  95

Ser Ser Asp Gly Gly Ser Thr Thr Pro Leu Ser Ile Arg Gly Ser Met
        100                 105                 110

Tyr Gln Met Trp Lys Val Leu Lys Ala Glu Leu Arg Ala Thr Pro Leu
    115                 120                 125

Thr Gly Gly Ala Asn Ile Val Gly Ser Val Gly Phe Met Val Leu Thr
130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
            165                 170                 175

Leu Ala Arg Asp Cys Ala Gly Pro Arg Glu Gly Trp Trp Leu Thr Asp
        180                 185                 190

```
Thr Ser Ser Ser Pro Ala Asp Ala Tyr Gly Pro Ala Val Asp Leu Met
        195                 200                 205

Val Ala Tyr Arg Thr Ser Asn Leu Leu Asn Val Ser Ser Ala Ser Thr
    210                 215                 220

Gln Pro Gln Ser Phe Thr Gly Thr Leu Trp Gln Ala Glu Leu Lys Val
225                 230                 235                 240

Thr Tyr Ala Phe Ser Thr Tyr Asp Pro Lys Pro Gly Leu Gln Thr Leu
                245                 250                 255

Val Ser Glu Thr Leu Ser Gly Ser His Gln Val Thr Ile Gln Ala Ser
                260                 265                 270

Ala Asp Asp Gly Ser Leu Ile Met Thr Thr Asp Thr Gln Leu Leu
            275                 280                 285

Ser Leu Leu Thr Pro Arg Thr Gly Asp Gln Lys Lys Gly Lys Ser Pro
            290                 295                 300

Thr Val Trp Ala Val Ala Gly Ala Val Val Asp Ala Val Ala Pro Val
305                 310                 315                 320

Leu Gly Pro Trp Gly Trp Leu Leu Lys Gly Phe Phe Leu Val Arg
                    325                 330                 335

Lys Ile Phe Gly Val Ser Ser Arg Asn Ala Gly Ala Ser Tyr Gln Ile
                340                 345                 350

Tyr Pro Ser Ile Glu Gln Ala Met Ser Asp Gln Pro Ile Phe Gly Gln
                355                 360                 365

Gln Ser Gly Thr Gly Thr Gln Ile Thr Leu Pro Leu Val His Val Ser
        370                 375                 380

Glu Val Met Asn Pro Asn Ser Glu Ser Asn Asp Leu Ser Ala Pro Thr
385                 390                 395                 400

Ser Arg Ala Leu Pro Pro Ala Pro Glu Pro Glu Pro Glu Leu Pro Leu
                405                 410                 415

Ala Leu Leu Val Gly Gln Ser Asn Val Pro Ala Val Tyr Glu Tyr Thr
                420                 425                 430

Gly Asp Ala Tyr Thr Pro Gln Pro Arg Trp Thr Gly Ser Thr Ile Phe
            435                 440                 445

Leu Thr Gly Ile Pro Tyr His Thr Arg Ala Thr Gly Ala Thr Gln Ser
    450                 455                 460

Phe Gly Val Arg Thr Asn Asn Met Ser Pro Ser Asn Cys Thr Thr Leu
465                 470                 475                 480

Asp Ile Tyr Asp Phe Thr Asn Phe Gly Val Phe Phe Gly Ser Asn Gly
                485                 490                 495

Tyr Leu Ser Gln Gly Ala Ile His Thr Ser Arg Thr Met Ile His Ser
                500                 505                 510

Leu Lys Thr Asn Pro Asn Ile Asn Pro Trp Leu Ala Ala Asn Gln Ser
            515                 520                 525

Ser Thr Thr Trp Ser Met Pro Thr Trp Ser Gly Tyr Pro Thr Pro Gly
    530                 535                 540

Gln Gly Asp Tyr Phe Leu Gln Met Gln Asp Thr Thr Asp Ser Thr Thr
545                 550                 555                 560

His Thr Thr Ser Val Gly Cys Tyr Phe Leu Val Met Tyr Gly Glu Ser
                565                 570                 575

Arg Lys Leu Ile Ala Phe Phe Asn Thr Gly Thr Gly Thr Ala Arg Pro
                580                 585                 590

Ala Leu Ser Ser Met Met Cys Leu Tyr Asn Val Asp Ala Gly Arg Ala
            595                 600                 605
```

-continued

```
Pro Val Arg Ile Gln Gly Phe Leu Leu Ser Pro Ser Gln Asn Phe Val
610                 615                 620

Glu Thr Asp Asn Gln Asp Pro Glu Asp Asp Asp Ile Ser Ile Ala
625                 630                 635                 640

Gly Ser Cys Leu Gln Asp Glu Phe Asp Cys Val Gly Gln Leu Glu Lys
                645                 650                 655

Glu Arg Glu Asp Leu Met Arg Arg Leu Arg Asp Leu Asp Leu Arg Arg
                660                 665                 670

Phe Gln Ile
        675

<210> SEQ ID NO 29
<211> LENGTH: 680
<212> TYPE: PRT
<213> ORGANISM: Avian Nephritis Virus

<400> SEQUENCE: 29

Met Pro Gly Pro Ala Gly Pro Ala Asn Gly Gly Ala Arg Pro Lys Thr
1               5                   10                  15

Gln Met Val Lys Pro Lys Ala Lys Lys Pro Pro Gln Lys Lys
                20                  25                  30

Pro Ser Gln Lys Pro Leu Arg Lys Glu Val Lys Val Glu Arg Gln
            35                  40                  45

Val Lys Val Leu Lys Lys Arg Thr Asn Gly Pro Lys Gln Asn Asp Val
50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
                85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
            115                 120                 125

Thr Gly Gly Ala Asn Val Val Gly Ser Val Gly Phe Met Val Leu Thr
130                 135                 140

Leu Asn Gly Leu Glu Ala Thr Ala Asp Ser Ile Asp Thr Ile Lys Ala
145                 150                 155                 160

Arg Lys His Val Gln Ile Ala Leu Gly Arg Ser Ala Ala Leu Arg Ile
                165                 170                 175

Leu Ala Arg Asp Cys Ala Gly Pro Arg Glu Gly Trp Trp Leu Thr Asp
            180                 185                 190

Thr Ser Ser Ser Pro Ala Asp Ser Tyr Gly Pro Ala Val Asp Leu Met
        195                 200                 205

Ile Ala Tyr Lys Thr Ser Asn Leu Leu Asn Val Ser Thr Ala Gly Ile
210                 215                 220

Pro Gln Ser Phe Thr Gly Thr Leu Trp Gln Val Glu Leu Lys Val Thr
225                 230                 235                 240

Tyr Ala Phe Ser Thr Tyr Asp Pro Lys Pro Gly Leu Gln Thr Leu Val
                245                 250                 255

Ser Gln Thr Leu Asp Gly Ser His Gln Val Thr Leu Gln Ser Thr
            260                 265                 270

Thr Asp Gly Ser Leu Ile Met Thr Thr Thr Asp Ala Thr Leu Leu Ser
        275                 280                 285

Ile Leu Thr Pro Arg Val Gly Gly Gln Arg Ser Gly Lys Ser Gln Thr
290                 295                 300
```

Val Trp Ser Ile Ala Gly Ala Ala Val Glu Ala Ala Pro Leu Leu
305                 310                 315                 320

Gly Pro Trp Gly Trp Leu Leu Lys Gly Gly Phe Trp Leu Val Arg Lys
            325                 330                 335

Ile Phe Gly Ala Ser Ala Arg Asp Thr Thr Ser Gln Tyr Gln Ile Tyr
            340                 345                 350

Pro Ser Ile Glu Ser Ala Met Ser Asp Gln Pro Ile Phe Gly Gln Thr
            355                 360                 365

Gly Ile Ser Thr Val Thr Leu Pro Ile Val His Ile Ser Glu Val Met
370                 375                 380

Asn Pro Asn Pro Glu Asn Asn Asp Leu Ser Asn Pro Thr Ser Arg Ser
385                 390                 395                 400

Leu Pro Pro Thr Pro Pro Thr Pro Pro Ala Gln Glu Lys Ile Leu Pro
            405                 410                 415

Leu Thr Leu Leu Glu Gly Gln Pro Gly Val Pro Ala Leu Tyr Thr Phe
            420                 425                 430

Asn Pro Ser Thr Glu Ala Tyr Thr Ala Ala Thr Gly Trp Thr Gly Gly
            435                 440                 445

Thr Leu Leu Leu Thr Gly Val Pro Glu Tyr Glu Leu Arg Ser Gly Ser
450                 455                 460

Ser Gln Gln Phe Gly Val Arg Val Thr Thr Ser Pro Gly Leu Pro Pro
465                 470                 475                 480

Ala Ala Ala Thr Ser Ile Gln Ile Tyr Asp Phe Thr Lys Phe Gly Ile
            485                 490                 495

Phe Phe Gly Ala Gly Ala Phe Leu Gly Gln Gly Gly Val His Thr Ala
            500                 505                 510

Lys Thr Leu Leu Thr Ala Ile Thr Ser Ser Ser Asn Pro Pro Trp Leu
            515                 520                 525

Ala Cys His Arg Tyr Thr Trp Ser Trp Pro Asp Trp Leu Val Thr Ala
530                 535                 540

Gly Tyr Pro Lys Pro Val Glu Gly Gly Trp Trp Leu Gln Met Gln Lys
545                 550                 555                 560

Ile Gly Asp Thr Thr Ser His Thr Thr Pro Val Gly Ile Tyr Phe Leu
            565                 570                 575

Val Ala Tyr Lys Glu Met Gln Gln Leu Val Ala Phe Trp His Thr Gly
            580                 585                 590

Ser Gly Ala Gln Ala Glu Pro Thr Ser Leu Met Cys Leu Tyr Asn Val
            595                 600                 605

Asp Ala Gly Arg Ala Pro Val Arg Val Pro His Phe Ile Leu Thr Thr
610                 615                 620

Thr Ala Arg Asn Glu Val Glu Val Asp Gly Gly Asp Asp Ser Asp Asp
625                 630                 635                 640

Asp Ile Ser Leu Ala Gly Ser Cys Val Gly Asp Glu Phe Glu Gly Val
            645                 650                 655

Asp Gln Leu Glu Arg Glu Arg Ala Glu Leu Met Ser Arg Leu Arg Asp
            660                 665                 670

Leu Asp Leu Arg Arg Phe Gln Ile
            675                 680

<210> SEQ ID NO 30
<211> LENGTH: 682
<212> TYPE: PRT
<213> ORGANISM: Avian Nephritis Virus -continued

```
<400> SEQUENCE: 30

Met Ala Gly Gly Ala Thr Ala Pro Ala Gly Ala Lys Pro Lys Gln Pro
1               5                   10                  15

Lys Gln Lys Gln Gln Lys Pro Cys Ser Gln Arg Lys Lys Lys Ile Pro
            20                  25                  30

Gln Lys Gln Lys Ser Met Lys Pro Val Lys Gln Glu Leu Arg Lys Val
        35                  40                  45

Glu Lys Gln Val Lys Val Leu Lys Ala Arg Thr Asn Gly Pro Lys Val
    50                  55                  60

Asn Asp Thr Met Lys Thr Thr Val Thr Val Gly Thr Leu Val Gly Gln
65                  70                  75                  80

Thr Gln Ser Gly Leu Asn Arg Gln Leu Arg Val Ser Phe Asn Pro Leu
                85                  90                  95

Leu Met Lys Ser Thr Asp Gly Gly Asn Thr Thr Pro Leu Ser Ile Arg
            100                 105                 110

Ala Ser Met Tyr Glu Met Trp Lys Pro Leu Ser Val Glu Ile Tyr Ala
        115                 120                 125

Thr Pro Leu Ser Gly Phe Ser Ser Val Val Gly Ser Val Gly Phe Met
    130                 135                 140

Val Leu Thr Leu Asn Gly Leu Glu Ala Ser Ala Asp Ser Ile Asp Thr
145                 150                 155                 160

Ile Lys Ala Arg Lys His Val Gln Met Ala Leu Gly Arg Pro Tyr Arg
                165                 170                 175

Leu Lys Leu Ser Ala Arg Glu Leu Ala Gly Pro Arg Glu Gly Trp Trp
            180                 185                 190

Leu Val Asp Thr Ser Glu Ser Pro Ala Asp Ala Tyr Gly Pro Ala Val
        195                 200                 205

Asp Leu Met Leu Ala Tyr Ala Thr Glu Asn Leu Leu Gly Thr Ser Ser
    210                 215                 220

Gly Ser Thr Thr Ser Tyr Thr Gly Thr Leu Trp Gln Val Glu Met Arg
225                 230                 235                 240

Val Ser Tyr Ala Phe Ser Thr Tyr Asn Pro Lys Pro Gly Leu Gln Thr
                245                 250                 255

Leu Ile Ser Gln Ser Ile Thr Gly Gly Gln Thr Val Thr Val Gln Pro
            260                 265                 270

Ser Pro Asp Asp Gly Ser Leu Ile Met Thr Thr Thr Ser Gln Gln Val
        275                 280                 285

Leu Ala Leu Leu Thr Pro Arg Val Ala Gly Gln Lys Lys Gly Lys Ser
    290                 295                 300

Gln Thr Ile Trp Ala Ile Ala Gly Ser Ala Ile Asp Ala Ala Ala Thr
305                 310                 315                 320

Val Leu Gly Pro Trp Gly Tyr Leu Leu Lys Gly Gly Phe Trp Leu Val
                325                 330                 335

Arg Leu Ile Phe Gly Gly Thr Ser Ala Arg Asn Pro Thr Thr Arg Gln
            340                 345                 350

Tyr Gln Ile Tyr Pro Ser Val Glu Ser Ala Leu Thr Asp Gln Pro Ile
        355                 360                 365

Phe Gly Asn Ala Thr Gly Thr Gln Ser Val Thr Val Pro Ile Cys His
    370                 375                 380

Ile Thr Glu Val Val Asn Pro Asn Ala Gly Lys Gln Gln Phe His Trp
385                 390                 395                 400

Ser Asn Asn Gln Val His Gln His His Arg Cys Pro Pro Thr Pro Ile
                405                 410                 415
```

```
Gln Asp Val Ile Leu Pro Leu Ala Glu Leu Thr Gly Gln Asp Gly Val
            420                 425                 430

Pro Ala Asn Tyr Thr Phe Asn Gly Asp Ser Tyr Thr Ala Gln Ser Asp
            435                 440                 445

Trp Arg Gly Ser Thr Leu Val Leu Thr Gly Ile Pro Arg His Lys Arg
450                 455                 460

Val Ala Gly Asn Leu Ser Asn Phe Gly Val Val Thr Asn Gln Met Ser
465                 470                 475                 480

Lys Val Thr Thr Thr Ala Leu Glu Ile Tyr Asp Phe Thr Asp Phe Gly
                485                 490                 495

Ile Phe Phe Gly Gly Tyr Gln Leu Gln Glu Gly Ile His Thr
            500                 505                 510

Gly Lys Thr Leu Val His Ser Leu Met Thr Gly Ala Pro Ile Lys Pro
            515                 520                 525

Trp Leu Tyr Ala Thr Gln Ser Ser Thr Thr Trp Tyr Trp Pro Asp Trp
            530                 535                 540

Thr Gly Phe Pro Lys Pro Gly Glu Gly Asp Tyr Phe Leu Gln Val Gln
545                 550                 555                 560

Asp Thr Thr Asp Arg Thr Thr His Thr Thr Cys Val Gly Ile Tyr Ile
                565                 570                 575

Val Val Ala Tyr Arg Gln Ser Arg Arg Leu Ile Ala Phe Phe Asn Asn
            580                 585                 590

Ala Gly Pro Val Arg Ala Ala Pro Thr Thr Met Leu Cys Leu Tyr Asn
            595                 600                 605

Val Asp Ala Gly Arg Ala Pro Ala Thr Pro Tyr Asn Thr Phe Gln Leu
            610                 615                 620

Thr Leu Gln Ser Glu Asn Ser Asp Pro Asn Ser Pro Ser Asp Asp Glu
625                 630                 635                 640

Asp Asp Asp Ile Ser Ile Ala Gly Ser Cys Leu Gln Asp Glu Phe Asp
                645                 650                 655

Cys Val Asp Gln Leu Glu Lys Glu Arg Glu Asp Leu Met Arg Arg Leu
            660                 665                 670

Arg Asp Leu Asp Leu Arg Arg Phe Gln Ser
            675                 680

<210> SEQ ID NO 31
<211> LENGTH: 682
<212> TYPE: PRT
<213> ORGANISM: Avian Nephritis Virus

<400> SEQUENCE: 31

Met Ala Gly Gly Ala Thr Ala Leu Ala Gly Ala Lys Pro Lys Gln Pro
1               5                   10                  15

Lys Gln Lys Gln Gln Lys Pro Gly Ser Gln Arg Lys Lys Lys Pro Pro
            20                  25                  30

Gln Lys Gln Lys Cys Met Lys Pro Val Lys Gln Glu Leu Arg Lys Val
            35                  40                  45

Glu Lys Gln Val Lys Val Leu Lys Ala Arg Thr Asn Gly Pro Lys Val
        50                  55                  60

Asn Asp Thr Met Lys Thr Thr Val Thr Val Gly Thr Leu Val Gly Gln
65                  70                  75                  80

Thr Gln Ser Gly Leu Asn Arg Gln Leu Arg Val Ser Phe Asn Pro Leu
                85                  90                  95

Leu Met Lys Ser Thr Asp Gly Gly Asn Thr Thr Pro Leu Ser Ile Arg
```

-continued

```
               100                 105                 110
Ala Ser Met Tyr Glu Met Trp Lys Ala Leu Ser Val Glu Ile Tyr Ala
        115                 120                 125

Thr Pro Leu Ser Gly Phe Ser Ser Val Val Gly Ser Val Gly Phe Met
    130                 135                 140

Val Leu Thr Leu Asn Gly Leu Glu Ala Ser Ala Asp Ser Ile Asp Thr
145                 150                 155                 160

Ile Lys Ala Arg Arg His Val Gln Met Ala Leu Gly Arg Pro Tyr Arg
                165                 170                 175

Leu Lys Leu Asn Ala Arg Glu Leu Ala Gly Pro Arg Glu Gly Trp Trp
            180                 185                 190

Leu Val Asp Thr Ser Glu Thr Pro Ala Glu Ala Tyr Gly Pro Ala Val
        195                 200                 205

Asp Leu Met Leu Ala Tyr Ala Thr Glu Asn Leu Leu Gly Thr Ser Ser
    210                 215                 220

Gly Ser Thr Thr Ser Tyr Thr Gly Thr Leu Trp Gln Val Glu Met Arg
225                 230                 235                 240

Val Ser Tyr Ala Phe Ser Thr Tyr Asn Pro Lys Pro Gly Leu Gln Thr
                245                 250                 255

Leu Ile Ser Gln Pro Ile Thr Gly Gly Gln Thr Val Thr Ile Gln Pro
            260                 265                 270

Ser Pro Asp Asp Gly Ser Leu Ile Met Thr Thr Thr Ser Gln Gln Val
        275                 280                 285

Leu Ala Leu Leu Thr Pro Arg Val Ala Ala Gly Gln Lys Lys Gly Lys
    290                 295                 300

Ser Gln Thr Ile Trp Ala Ile Ala Gly Ser Ala Val Asp Ala Ala Ala
305                 310                 315                 320

Thr Val Leu Gly Pro Trp Gly Tyr Leu Leu Lys Gly Gly Phe Trp Leu
                325                 330                 335

Val Arg Leu Ile Phe Gly Gly Gly Ser Ala Arg Asn Thr Thr Thr Arg
            340                 345                 350

Gln Phe Gln Ile Tyr Pro Ser Val Glu Ser Ala Leu Ala Asp Gln Pro
        355                 360                 365

Ile Tyr Gly Asn Ser Thr Gly Thr Gln Ser Val Thr Val Pro Ile Cys
    370                 375                 380

His Ile Thr Glu Val Val Asn Pro Asn Ala Glu Ser Asn Asn Leu Thr
385                 390                 395                 400

Leu Pro Thr Thr Ser Ala Pro Ala Pro Pro Thr Pro Ser Pro Ser
                405                 410                 415

Glu Asp Pro Ile Leu Pro Leu Ala Glu Leu Thr Gly Gln Pro Gly Val
            420                 425                 430

Pro Pro Leu Tyr Thr Phe Asp Gly Ser Ser Tyr Thr Pro Ala Pro Asn
        435                 440                 445

Trp Leu Gly Ser Thr Leu Leu Leu Thr Gly Ile Pro Ala His Lys Arg
    450                 455                 460

Val Thr Gly Asn Leu Ala Asn Phe Gly Val Thr Asn Leu Gln Met Ser
465                 470                 475                 480

Lys Val Thr Ala Thr Ala Val Glu Ile Tyr Asp Phe Thr Asp Phe Gly
                485                 490                 495

Val Phe Phe Gly Thr Gly Ser Phe Leu Gly Glu Gly Gly Ile His Thr
            500                 505                 510

Gly Lys Thr Leu Ile Tyr Ser Leu Met Ser Gly Gln Asp Pro Lys Pro
        515                 520                 525
```

Trp Leu Ala Ala Asn Gln Ser Gly Thr Thr Trp Tyr Leu Pro Ser Trp
            530                 535                 540

Val Gly Phe Pro Thr Pro Gly Ala Gly Asp Tyr Phe Leu Gln Met Gln
545                 550                 555                 560

Asp Thr Thr Asp Thr Thr Thr His Thr Thr Ser Val Asn Val Tyr Phe
                565                 570                 575

Leu Val Ala Tyr Arg Gln Ser Arg Arg Leu Ile Ala Phe Phe Asn Thr
            580                 585                 590

Gly Gly Thr Ala Arg Pro Ala Pro Thr Ser Met Leu Cys Met Tyr Asn
        595                 600                 605

Val Asp Cys Gly Arg Ala Pro Ala Thr Pro Tyr Pro Thr Tyr Gln Ser
    610                 615                 620

Ala Leu Gln Ser Lys Val Glu Val Ala Asn Ser Glu Thr Leu Asp Ser
625                 630                 635                 640

Asp Asp Asp Ile Ser Leu Ala Gly Ser Cys Ile Gly Asp Glu Phe Glu
                645                 650                 655

Ser Val Asp Gln Leu Glu Arg Glu Arg Glu Asp Leu Met Arg Arg Leu
            660                 665                 670

Arg Asp Leu Asp Leu Arg Arg Phe His Ile
        675                 680

<210> SEQ ID NO 32
<211> LENGTH: 182
<212> TYPE: DNA
<213> ORGANISM: Artificial
<220> FEATURE:
<223> OTHER INFORMATION: synthesised nucleic acid sequence

<400> SEQUENCE: 32
aatgaaaagc ccactttcgg gagaaccaac tttagcgcac aggagcgtag gttttagcag      60
gctccaagtt gcgtgagtgg cggtttgatt gacctaccac cccattggtc cccctagcac     120
agccaaatta gttgactatg caatggtccc agctttcctg taccctcgat gctactcgcc     180
gt                                                                    182

<210> SEQ ID NO 33
<211> LENGTH: 56
<212> TYPE: DNA
<213> ORGANISM: Artificial
<220> FEATURE:
<223> OTHER INFORMATION: synthesised nucleic acid sequence

<400> SEQUENCE: 33
tactcgccgt ggcctcggga aagtcagttg ctgtagtcag ccaaccagtg gtttac          56

<210> SEQ ID NO 34
<211> LENGTH: 20
<212> TYPE: DNA
<213> ORGANISM: Artificial
<220> FEATURE:
<223> OTHER INFORMATION: synthesised nucleic acid sequence

<400> SEQUENCE: 34
aatgaaaagc ccactttcgg                                                  20

<210> SEQ ID NO 35
<211> LENGTH: 17
<212> TYPE: DNA
<213> ORGANISM: Artificial
<220> FEATURE:

<223> OTHER INFORMATION: synthesised nucleic acid sequence

<400> SEQUENCE: 35
tactcgccgt ggcctcg                17

<210> SEQ ID NO 36
<211> LENGTH: 683
<212> TYPE: PRT
<213> ORGANISM: Avian Nephritis Virus

<400> SEQUENCE: 36

```
Met Ala Gly Gly Ala Thr Ala Pro Ala Gly Ala Lys Pro Lys Gln Pro
1               5                   10                  15

Lys Gln Lys Gln Lys Lys Pro Ser Ser Gln Ala Arg Lys Lys Pro Ser
            20                  25                  30

Gln Lys Gln Lys Ala Met Lys Pro Val Lys Gln Glu Leu Arg Lys Val
        35                  40                  45

Glu Lys Gln Val Arg Val Leu Lys Ala Arg Thr Asn Gly Pro Lys Val
    50                  55                  60

Asn Asp Thr Met Lys Thr Thr Val Thr Val Gly Thr Leu Val Gly Gln
65                  70                  75                  80

Thr Gln Ser Gly Leu Asn Arg Gln Leu Arg Val Ser Phe Asn Pro Leu
                85                  90                  95

Leu Met Lys Ser Thr Glu Gly Gly Ser Thr Thr Pro Leu Ser Ile Arg
            100                 105                 110

Ala Ser Met Tyr Glu Met Trp Lys Pro Leu Ser Val Glu Ile Phe Ala
        115                 120                 125

Thr Pro Leu Ser Gly Phe Ser Ser Val Val Gly Ser Val Gly Phe Met
    130                 135                 140

Val Ile Thr Leu Asn Gly Leu Glu Ala Ser Ala Asp Ser Ile Asp Thr
145                 150                 155                 160

Ile Lys Ala Arg Arg His Val Gln Met Ala Leu Gly Arg Pro Tyr Arg
                165                 170                 175

Leu Lys Leu Ser Ala Arg Glu Leu Ala Gly Pro Arg Glu Gly Trp Trp
            180                 185                 190

Leu Val Asp Thr Ser Glu Ala Pro Ala Asp Ala Tyr Gly Pro Ala Val
        195                 200                 205

Asp Leu Met Leu Ala Tyr Ala Thr Glu Asn Leu Gly Thr Ser Ser
    210                 215                 220

Gly Ser Thr Thr Ser Tyr Thr Gly Thr Leu Trp Gln Val Glu Met Arg
225                 230                 235                 240

Val Thr Tyr Ala Phe Ser Thr Tyr Asn Pro Lys Pro Gly Leu Gln Thr
                245                 250                 255

Leu Val Ser Gln Ser Ile Thr Gly Gly Thr Val Thr Ile Gln Pro
            260                 265                 270

Ser Pro Asp Asp Gly Ser Leu Ile Met Thr Thr Asn Ser Gln Gln Val
        275                 280                 285

Leu Ala Leu Leu Thr Pro Arg Val Ala Gly Gln Arg Lys Gly Lys Ser
    290                 295                 300

Gln Thr Ile Trp Ala Ile Ala Gly Ser Ala Val Asp Ala Ala Ala Thr
305                 310                 315                 320

Val Leu Gly Pro Trp Gly Tyr Leu Leu Lys Gly Gly Phe Trp Leu Val
                325                 330                 335

Arg Leu Ile Phe Gly Gly Ser Ser Ala Arg Asn Thr Thr Thr Arg Gln
            340                 345                 350
```

```
Tyr Gln Ile Tyr Pro Ser Val Glu Ser Ala Leu Thr Asp Gln Pro Ile
            355                 360                 365

Phe Gly Asn Ser Thr Gly Thr Gln Ser Val Thr Val Pro Ile Cys His
        370                 375                 380

Ile Thr Glu Val Val Asn Pro Asn Ala Glu Ser Asn Asn Leu Pro Pro
385                 390                 395                 400

Pro Thr Thr Gly Ala Gln Pro Gln Pro Gln Pro Pro Ala Pro Ile Glu
                405                 410                 415

Glu Ile Leu Leu Pro Leu Ala Glu Leu Thr Gly Gln Pro Gly Val Pro
            420                 425                 430

Pro Leu Tyr Thr Phe Asp Gly Ser Ser Tyr Thr Pro Thr Asn Trp
        435                 440                 445

Leu Gly Ser Thr Ile Leu Leu Thr Gly Ile Pro Ala His Lys Arg Val
        450                 455                 460

Thr Gly Asn Leu Ala Lys Phe Gly Val Thr Asn Leu Gln Met Ser Lys
465                 470                 475                 480

Val Ala Ala Thr Ala Leu Glu Ile Tyr Asp Phe Thr Asp Phe Gly Val
                485                 490                 495

Phe Phe Gly Thr Gly Ser Tyr Leu Ser Glu Gly Gly Ile His Thr Gly
            500                 505                 510

Lys Thr Leu Ile Tyr Ser Leu Met Ser Gly Gln Thr Pro Asn Pro Trp
        515                 520                 525

Leu Ala Ala Asn Gln Ser Gly Thr Thr Trp Tyr Met Pro Ser Trp Ala
        530                 535                 540

Gly Phe Pro Gln Pro Gly Gln Gly Asp Tyr Phe Leu Gln Met Gln Asp
545                 550                 555                 560

Val Thr Asp Thr Thr Thr His Thr Thr Ser Val Asn Val Tyr Phe Leu
                565                 570                 575

Val Ala Tyr Arg Gln Ser Arg Arg Leu Ile Ala Phe Phe Asn Thr Gly
            580                 585                 590

Gly Thr Ala Arg Pro Ala Pro Thr Ser Met Leu Cys Leu Tyr Asn Val
        595                 600                 605

Asp Cys Gly Arg Ala Pro Gln Thr Pro Tyr Pro Thr Phe Gln Ser Thr
        610                 615                 620

Leu Gln Ser Leu Asn Gln Ile Gly Val Asp Ala Lys Ser Asp Pro Asp
625                 630                 635                 640

Ser Asp Asp Asp Ile Ser Leu Ala Gly Ser Val Ile Gly Asp Glu Phe
                645                 650                 655

Asp Ser Val Asp His Leu Glu Arg Glu Arg Glu Asp Leu Met Arg Arg
            660                 665                 670

Leu Arg Asp Leu Asp Leu Arg Arg Phe Gln Ile
        675                 680

<210> SEQ ID NO 37
<211> LENGTH: 679
<212> TYPE: PRT
<213> ORGANISM: Avian Nephritis Virus

<400> SEQUENCE: 37

Met Ala Gly Gly Ala Thr Ala Pro Ala Gly Ala Lys Pro Lys Gln Ser
1               5                   10                  15

Lys Gln Lys Gln Lys Asn Ser Ser Gln Arg Lys Ser Lys Ile Thr Gln
            20                  25                  30

Lys Ala Lys Gln Gln Lys Pro Pro Val Lys Thr Val Arg Arg Leu Glu
```

```
                35                  40                  45
Arg Gln Val Asn Ala Leu Lys Lys Thr Asn Gly Pro Lys Met Asn
 50                  55                  60
Asp Met Met Lys Thr Thr Val Thr Ile Gly Val Ile Gln Gly Gln Thr
 65                  70                  75                  80
Gln Ser Gly Leu Ser Arg Gln Ile Arg Val Pro Leu Asn Pro Leu Leu
                     85                  90                  95
Met Lys Ser Thr Glu Gly Leu Ala Ala Thr Pro Leu Ser Ile Arg Ser
                100                 105                 110
Ser Cys Tyr Glu Leu Trp Lys Ala Leu His Val Glu Leu Phe Ala Thr
                115                 120                 125
Pro Leu Thr Gly Phe Ser Asn Val Val Gly Ser Val Gly Phe Met Ala
130                 135                 140
Leu Thr Leu Asn Gly Leu Glu Ala Thr Ala Asp Ser Ile Asp Ser Ile
145                 150                 155                 160
Lys Ala Arg Lys His Tyr Gln Met Ala Leu Gly Arg Pro Ala Arg Leu
                165                 170                 175
Lys Leu Thr Ala Arg Glu Leu Ala Gly Pro Arg Glu Gly Trp Trp Leu
                180                 185                 190
Thr Asp Thr Ser Glu Ser Pro Val Asp Ala Tyr Gly Pro Ala Ile Asp
                195                 200                 205
Leu Met Ile Ala Tyr Lys Thr Glu Asn Leu Leu Asn Thr Thr Gly Ser
210                 215                 220
Tyr Ile His Leu Tyr Trp Thr Thr Val Ala Asp Arg Lys Arg Arg Val
225                 230                 235                 240
Thr Tyr Gly Phe Ala Asn Tyr Asn Pro Lys Pro Gly Leu Gln Thr Leu
                245                 250                 255
Val Ser Gln Thr Leu Thr Asn Gly Gln Thr Val Thr Ile Gln Pro Ser
                260                 265                 270
Pro Asn Asp Gly Ser Leu Ile Met Thr Thr Thr Ser Leu Gln Ile Arg
                275                 280                 285
Ser Leu Leu Ser Pro Arg Val Gly Asp Pro Lys Lys Gly Lys Ser Gln
290                 295                 300
Thr Ile Trp Ala Ile Ala Gly Ser Ala Val Asp Ala Ala Thr Val
305                 310                 315                 320
Leu Gly Pro Trp Gly Trp Leu Leu Lys Gly Gly Phe Trp Leu Val Arg
                325                 330                 335
Gln Ile Ser Gly Gly Ser Ser Asn Ala Pro Gly Ser Ser Tyr Gln Ile
                340                 345                 350
Tyr Ser Ser Leu Glu Ser Ala Met Ala Asp Gln Pro Ile Phe Gly Ala
                355                 360                 365
Gln Thr Gly Thr Gln Ser Ile Thr Val Pro Val His Ile Ser Glu
                370                 375                 380
Val Leu Asn Pro Asn Pro Met Ser Asn Gln Val Pro Thr Pro Ser Thr
385                 390                 395                 400
Gly Ser Ala Pro Ala Pro Pro Thr Pro Pro Thr Pro Ile Gln Asp Ile
                405                 410                 415
Ile Leu Pro Leu Ala Glu Leu Thr Gly Gln Asp Gly Val Pro Ala Asn
                420                 425                 430
Tyr Thr Phe Asn Gly Asp Ser Tyr Thr Ala Gln Ala Asp Trp Arg Gly
                435                 440                 445
Ser Thr Leu Val Leu Thr Gly Ile Pro Lys His Lys Arg Val Ala Gly
450                 455                 460
```

```
Asn Leu Ser Asn Phe Gly Val Val Thr Asn Gln Met Ser Lys Val Thr
465                 470                 475                 480

Thr Thr Ala Leu Glu Ile Tyr Asp Phe Thr Asp Phe Gly Ile Val Phe
            485                 490                 495

Gly Gly Gly Tyr Gln Leu Gln Glu Gly Gly Ile His Thr Gly Lys Thr
                500                 505                 510

Leu Val His Ser Leu Met Thr Gly Ala Pro Ile Lys Pro Trp Leu Tyr
            515                 520                 525

Ala Thr Gln Ser Ser Thr Thr Trp Tyr Trp Pro Asp Trp Thr Gly Phe
530                 535                 540

Pro Lys Pro Gly Glu Gly Asp Tyr Phe Leu Gln Met Gln Asp Thr Thr
545                 550                 555                 560

Asp Arg Thr Thr His Thr Thr Cys Val Gly Ile Tyr Ile Val Val Ala
                565                 570                 575

Tyr His Gln Ser Arg Arg Leu Ile Ala Phe Phe Asn Asn Ala Gly Pro
                580                 585                 590

Val Arg Ala Ala Pro Thr Thr Met Leu Cys Leu Tyr Asn Val Asp Ala
            595                 600                 605

Gly Arg Ala Pro Ala Thr Pro Tyr Asn Thr Phe Gln Leu Thr Leu Gln
            610                 615                 620

Ser Glu Gly Thr Asp Pro Asn Ser Pro Ser Glu Asp Glu Asp Asp
625                 630                 635                 640

Ile Ser Leu Ala Gly Ser Cys Leu Gln Asp Glu Phe Asp Cys Val Asp
                645                 650                 655

Gln Leu Glu Lys Glu Arg Glu Asp Leu Met Arg Arg Leu Arg Asp Leu
                660                 665                 670

Asp Leu Arg Arg Phe Gln Ile
            675
```

<210> SEQ ID NO 38
<211> LENGTH: 677
<212> TYPE: PRT
<213> ORGANISM: Avian Nephritis Virus

<400> SEQUENCE: 38

```
Met Pro Gly Pro Ala Gly Pro Ala Asn Gly Gly Ala Arg Pro Lys Thr
1               5                   10                  15

Gln Met Ala Lys Pro Lys Ala Lys Lys Pro Pro Ser Gln Lys Lys
                20                  25                  30

Pro Ser Gln Gln Lys Pro Leu Arg Arg Glu Ile Lys Lys Val Glu Lys
            35                  40                  45

Gln Val Arg Val Leu Lys Lys Arg Thr Asn Gly Pro Lys Gln Asn Asp
        50                  55                  60

Leu Phe Thr Thr Thr Val Thr Leu Gly Thr Ile Ser Gly Gln Ser Asp
65                  70                  75                  80

Asn Gly Leu Thr Arg Gln Ile Arg Leu Pro Leu Asn Pro Leu Leu
                85                  90                  95

Lys Ser Ser Asp Gly Gly Ser Thr Thr Pro Leu Ser Ile Arg Gly Ser
                100                 105                 110

Met Tyr Glu Met Trp Lys Val Ile Arg Ala Glu Leu Ile Ala Thr Pro
            115                 120                 125

Leu Thr Gly Gly Ala Asn Ile Val Gly Ser Val Gly Phe Met Val Leu
    130                 135                 140

Thr Leu Asn Glu Leu Glu Ala Thr Ala Asp Ser Ile Asp Ser Ile Lys
```

-continued

```
          145                 150                 155                 160
Ala Arg Lys His Val Gln Ile Pro Leu Gly Arg Leu Ala Arg Leu Arg
                    165                 170                 175
Leu Thr Ala Arg Glu Cys Ala Gly Pro Arg Glu Gly Trp Trp Leu Thr
                180                 185                 190
Asp Thr Ser Gln Ser Pro Ala Asp Ser Tyr Gly Pro Ala Val Asp Leu
            195                 200                 205
Met Ile Ala Tyr Ala Thr Thr Asn Leu Leu Asn Thr Ser Gly Gly Ala
210                 215                 220
Ser Ala Thr Phe Leu Gly Thr Leu Trp Gln Val Glu Ile Arg Val Thr
225                 230                 235                 240
Tyr Ala Phe Ser Thr Tyr Asn Pro Lys Pro Gly Leu Gln Thr Met Val
                245                 250                 255
Ser Gln Thr Leu Ala Gly Ser Asn His Gln Val Thr Ile Gln Gln Ser
                260                 265                 270
Thr Thr Asp Gly Ser Leu Ile Met Thr Thr Asn Asp Ala Asn Leu Leu
            275                 280                 285
Ser Ile Leu Thr Pro Arg Val Ala Gly Gln Arg Ser Gly Lys Ser Gln
        290                 295                 300
Thr Val Trp Ala Ile Ala Gly Ala Ala Val Glu Ala Ala Pro Leu
305                 310                 315                 320
Leu Gly Pro Trp Gly Trp Leu Leu Lys Gly Gly Phe Trp Leu Val Arg
                325                 330                 335
Lys Ile Phe Gly Ala Ser Ala Arg Asp Thr Thr Ser Gln Tyr Gln Ile
                340                 345                 350
Tyr Pro Ser Ile Glu Ala Ala Met Ser Asp Gln Pro Ile Phe Gly Gln
            355                 360                 365
Thr Gly Thr Ser Thr Thr Val Thr Leu Pro Ile Val His Ile Ser Glu
        370                 375                 380
Val Met Asn Pro Asn Pro Glu Asn Asn Asp Leu Thr Asn Pro Thr Ala
385                 390                 395                 400
Arg Ser Leu Pro Pro Val Pro Pro Ala Pro Ser Glu Asp Pro Ile Leu
                405                 410                 415
Pro Leu Ala Glu Leu Thr Gly Gln Asp Gly Val Pro Ala Asn Tyr Thr
                420                 425                 430
Phe Asn Gly Asp Ser Tyr Thr Gly Gln Ala Asp Trp Arg Gly Ser Thr
            435                 440                 445
Leu Val Leu Thr Gly Ile Pro Lys His Lys Arg Val Ala Gly Ser Leu
        450                 455                 460
Ala Asn Phe Gly Val Val Thr Asn Gln Met Ser Lys Val Thr Thr Thr
465                 470                 475                 480
Ala Leu Glu Ile Tyr Asp Phe Thr Asp Phe Gly Ile Phe Phe Gly Gly
                485                 490                 495
Gly Tyr Gln Leu Gln Glu Gly Gly Val His Thr Gly Lys Thr Met Val
                500                 505                 510
His Ser Leu Met Thr Gly Ala Pro Ile Lys Pro Trp Leu Tyr Ala Thr
            515                 520                 525
Gln Ser Ser Thr Thr Trp Tyr Trp Pro Thr Trp Thr Gly Phe Pro Gln
        530                 535                 540
Pro Gly Glu Gly Asp Tyr Phe Leu Gln Met Gln Asp Thr Thr Asp Arg
545                 550                 555                 560
Thr Thr His Thr Thr Cys Val Ser Val Tyr Leu Leu Val Ala Tyr Arg
                565                 570                 575
```

```
Ala Ser Arg Arg Leu Ile Ala Phe Tyr Asn Asn Gly Gly Pro Val Arg
            580                 585                 590

Ala Ala Pro Thr Thr Met Leu Cys Leu Tyr Asn Val Asp Ala Gly Arg
            595                 600                 605

Ala Pro Ala Thr Pro Tyr Asn Thr Phe Gln Leu Thr Leu Gln Ser Glu
            610                 615                 620

Gly Ala Asp Pro Asn Ser Pro Ser Glu Asp Glu Asp Asp Ile Ser
625                 630                 635                 640

Leu Ala Gly Ser Cys Leu Gln Asp Glu Phe Asp Cys Val Asp Gln Leu
            645                 650                 655

Glu Lys Glu Arg Glu Asp Leu Met Arg Arg Leu Arg Asp Leu Asp Leu
            660                 665                 670

Arg Arg Phe Gln Ile
        675
```

<210> SEQ ID NO 39
<211> LENGTH: 677
<212> TYPE: PRT
<213> ORGANISM: Avian Nephritis Virus

<400> SEQUENCE: 39

```
Met Ala Gly Pro Ala Gly Ser Ser Asn Arg Gly Ala Arg Pro Lys Thr
1               5                   10                  15

Gln Met Ala Lys Pro Lys Ala Lys Pro Pro Ser Gln Lys Lys
            20                  25                  30

Pro Ser Gln Lys Pro Leu Arg Lys Glu Val Lys Val Glu Arg Gln
            35                  40                  45

Val Lys Val Leu Lys Lys Arg Thr Asn Gly Pro Lys Gln Asn Asp Val
50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
            85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
            115                 120                 125

Thr Gly Gly Ala Asn Val Val Gly Ser Val Gly Phe Met Val Leu Thr
            130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
            165                 170                 175

Leu Ala Arg Asp Cys Ala Gly Pro Arg Glu Gly Trp Trp Leu Thr Asp
            180                 185                 190

Thr Ser Ser Ser Pro Ala Asp Ala Tyr Gly Pro Ala Val Asp Leu Met
            195                 200                 205

Ile Ala Tyr Lys Thr Ser Asn Leu Leu Asn Val Ser Ser Thr Thr Gly
            210                 215                 220

Pro Gln Pro Phe Thr Gly Thr Leu Trp Gln Ala Glu Leu Lys Val Thr
225                 230                 235                 240

Tyr Ala Phe Ser Thr Tyr Asp Pro Lys Pro Gly Leu Gln Thr Leu Val
            245                 250                 255

Ser Glu Thr Leu Ser Gly Ser His Gln Val Thr Ile Gln Thr Ser Ala
```

-continued

Asp Asp Gly Ser Leu Ile Met Thr Thr Thr Asp Thr Gln Leu Leu Ser
         260                 265                 270
                 275                 280                 285

Leu Leu Thr Pro Arg Thr Gly Asp Gln Lys Lys Gly Lys Ser Pro Thr
        290                 295                 300

Val Trp Ala Val Ala Gly Ala Val Val Asp Ala Val Ala Pro Val Leu
305                 310                 315                 320

Gly Pro Trp Gly Trp Leu Leu Lys Gly Gly Phe Phe Leu Val Arg Lys
                325                 330                 335

Ile Phe Gly Ala Ser Thr Arg Asn Ala Gly Ala Ser Tyr Gln Ile Tyr
        340                 345                 350

Pro Ser Ile Glu Gln Ala Met Ser Asp Gln Pro Ile Phe Gly Gln Gln
        355                 360                 365

Ser Gly Thr Thr Gln Val Thr Leu Pro Leu Val His Val Ser Glu Val
        370                 375                 380

Met Asn Pro Asn Ser Glu Ser Asn Asp Leu Asn Pro Thr Ala Arg Ser
385                 390                 395                 400

Leu Pro Pro Ile Pro Pro Ala Gln Glu Lys Ile Leu Pro Leu Thr Leu
                405                 410                 415

Leu Glu Gly Gln Ser Gly Val Pro Ala Leu Tyr Thr Phe Asn Ser Gly
        420                 425                 430

Thr Gly Ala Tyr Thr Pro Met Thr Arg Trp Thr Gly Thr Leu Leu
        435                 440                 445

Leu Thr Gly Val Pro Glu Tyr Glu Leu Arg Ser Gly Ser Ser Gln Gln
        450                 455                 460

Phe Gly Val Arg Val Gln Asn Ser Pro Gly Leu Ser Pro Ala Ala Ala
465                 470                 475                 480

Thr Ser Ile Gln Ile Tyr Asp Phe Thr Lys Phe Gly Ile Phe Gly
                485                 490                 495

Ala Gly Glu Phe Leu Gly Gln Gly Gly Val His Thr Ala Lys Thr Leu
                500                 505                 510

Leu Thr Ala Ile Thr Ala Ser Ser Asn Pro Pro Trp Leu Asp Cys Ser
        515                 520                 525

Arg Tyr Thr Trp Ser Trp Pro Asp Trp Leu Thr Ser Ala Gly Tyr Pro
        530                 535                 540

Lys Pro Ala Gln Gly Asp Trp Trp Leu Gln Met Gln Lys Val Gly Asp
545                 550                 555                 560

Thr Thr Ser His Thr Thr Pro Val Gly Ile Tyr Phe Leu Ile Ala Tyr
                565                 570                 575

Glu Glu Met Gln Gln Leu Val Ala Phe Trp His Thr Gly Ser Gly Ala
                580                 585                 590

Gln Ala Glu Pro Thr Ser Leu Leu Cys Leu Tyr Asn Val Asp Ala Gly
        595                 600                 605

Arg Ala Pro Val Arg Val Pro His Phe Ile Ile Thr Thr Thr Ala Arg
        610                 615                 620

Asn Glu Val Glu Val Asp Gly Gly Asp Asp Ser Asp Asp Ile Ser
625                 630                 635                 640

Leu Ala Gly Ser Cys Val Gly Asp Glu Phe Glu Gly Val Asp Gln Leu
                645                 650                 655

Glu Arg Glu Arg Ala Glu Leu Met Ser Arg Leu Arg Asp Leu Asp Leu
        660                 665                 670

Arg Arg Phe Gln Ile
        675

<210> SEQ ID NO 40
<211> LENGTH: 673
<212> TYPE: PRT
<213> ORGANISM: Avian Nephritis Virus

<400> SEQUENCE: 40

```
Met Pro Gly Pro Ala Gly Pro Ala Asn Gly Gly Ala Arg Pro Lys Thr
1               5                   10                  15

Gln Met Ala Lys Pro Lys Lys Ala Lys Lys Pro Pro Ser Gln Lys Lys
            20                  25                  30

Pro Pro Gln Lys Pro Pro Arg Lys Glu Val Lys Lys Val Glu Arg Gln
        35                  40                  45

Val Lys Val Leu Lys Lys Arg Thr Asn Gly Pro Lys Gln Asn Asp Val
    50                  55                  60

Phe Thr Thr Thr Val Thr Leu Gly Thr Ile Ser Gly Gln Asn Asp Asn
65                  70                  75                  80

Gly Leu Thr Arg Gln Ile Arg Val Pro Phe Asn Pro Leu Leu Cys Lys
                85                  90                  95

Ser Ser Asp Gly Gly Ser Thr Thr Pro Leu Ser Ile Arg Gly Ser Met
            100                 105                 110

Tyr Gln Met Trp Lys Val Leu Lys Ala Glu Leu Arg Ala Thr Pro Leu
        115                 120                 125

Thr Gly Gly Ala Asn Ile Val Gly Ser Val Gly Phe Met Val Leu Thr
    130                 135                 140

Leu Asn Gly Leu Glu Ala Thr Ala Asp Ser Ile Asp Thr Ile Lys Ala
145                 150                 155                 160

Arg Lys His Val Gln Ile Pro Ile Gly Arg Ser Ala Val Leu Arg Ile
                165                 170                 175

Leu Ala Arg Asp Cys Ala Gly Pro Arg Glu Gly Trp Trp Leu Thr Asp
            180                 185                 190

Thr Ser Ser Ser Pro Ala Asp Ala Tyr Gly Pro Ala Val Asp Leu Met
        195                 200                 205

Val Ala Tyr Arg Thr Ser Asn Leu Leu Asn Val Ser Ser Ala Ser Thr
    210                 215                 220

Gln Pro Gln Ser Phe Thr Gly Thr Leu Trp Gln Ala Glu Leu Lys Val
225                 230                 235                 240

Thr Tyr Ala Phe Ser Thr Tyr Asp Pro Lys Pro Gly Leu Gln Thr Leu
                245                 250                 255

Val Ser Glu Thr Leu Ser Gly Ser His Gln Val Thr Ile Gln Thr Ser
            260                 265                 270

Ala Asp Asp Gly Ser Leu Ile Met Thr Thr Thr Asp Thr Gln Leu Leu
        275                 280                 285

Ser Leu Leu Thr Pro Arg Thr Gly Asp Gln Lys Lys Gly Lys Ser Pro
    290                 295                 300

Thr Val Trp Ala Val Ala Gly Ala Val Val Asp Ala Val Ala Pro Val
305                 310                 315                 320

Leu Gly Pro Trp Gly Trp Leu Leu Lys Gly Gly Phe Phe Leu Val Arg
                325                 330                 335

Lys Ile Phe Gly Val Ser Ala Arg Asn Ala Gly Ala Ser Tyr Gln Ile
            340                 345                 350

Tyr Pro Ser Ile Glu Gln Ala Met Ser Asp Gln Pro Ile Phe Gly Gln
        355                 360                 365

Gln Ser Gly Thr Thr Gln Val Thr Leu Pro Leu Val His Val Ser Glu
```

```
             370                 375                 380
Val Met Asn Pro Asn Ser Glu Ser Asn Asp Leu Thr Pro Thr Ser Arg
385                 390                 395                 400

Ala Leu Pro Pro Ala Pro Glu Ser Glu Pro Glu Leu Pro Leu Ala Leu
                405                 410                 415

Leu Val Gly Gln Ala Gly Val Pro Ala Val Tyr Glu Tyr Thr Gly Asp
                420                 425                 430

Ala Tyr Thr Pro Gln Pro Arg Trp Thr Gly Ser Thr Ile Phe Leu Thr
                435                 440                 445

Gly Val Pro Tyr His Thr Arg Ala Thr Gly Ala Thr Gln Ser Phe Gly
                450                 455                 460

Val Arg Thr Asn Asn Met Ser Pro Ser Asn Cys Thr Thr Leu Asp Ile
465                 470                 475                 480

Tyr Asp Phe Thr Asp Phe Gly Val Phe Phe Gly Ser Asn Gly Tyr Leu
                485                 490                 495

Ser Gln Gly Ala Ile His Thr Ser Lys Thr Met Ile Tyr Ser Leu Lys
                500                 505                 510

Thr Asn Pro Asn Ile Asn Pro Trp Leu Ala Ala Asn Gln Ser Ser Thr
                515                 520                 525

Thr Trp Ser Met Pro Thr Trp Ser Gly Tyr Pro Ala Pro Gly Gln Gly
                530                 535                 540

Asp Tyr Phe Leu Gln Met Gln Asp Thr Thr Asp Thr Thr Thr His Thr
545                 550                 555                 560

Thr Ser Val Gly Cys Tyr Phe Leu Val Met Tyr Gly Glu Ser Arg Lys
                565                 570                 575

Leu Val Ala Phe Phe Asn Thr Gly Thr Gly Thr Ala Arg Pro Ala Leu
                580                 585                 590

Ser Ser Met Met Cys Leu Tyr Asn Val Asp Ala Gly Arg Ala Pro Val
                595                 600                 605

Arg Ile Gln Gly Phe Leu Leu Ser Pro Ser Gln Asn Phe Val Glu Thr
                610                 615                 620

Asp Asn Gln Asp Asn Asp Asp Asp Ile Ser Leu Ala Gly Ser
625                 630                 635                 640

Cys Leu Gln Asp Glu Phe Asp Cys Val Asp Gln Leu Glu Lys Glu Arg
                645                 650                 655

Glu Asp Leu Met Arg Arg Leu Arg Asp Leu Asp Leu Arg Arg Phe Gln
                660                 665                 670

Ile
```